(12) United States Patent
Cloos et al.

(10) Patent No.: US 8,420,335 B2
(45) Date of Patent: Apr. 16, 2013

(54) INHIBITION OF GASC1

(75) Inventors: Paul Cloos, Copenhagen (DK); Karl Agger, Copenhagen (DK); Jesper Christensen, Copenhagen (DK); Klaus H. Hansen, Copenhagen (DK); Kristian Helin, Copenhagen (DK)

(73) Assignee: Kobenhavns Universitet, Kobenhavn K (DK)

( * ) Notice: Subject to any disclaimer, the term of this patent is extended or adjusted under 35 U.S.C. 154(b) by 1083 days.

(21) Appl. No.: 12/282,485

(22) PCT Filed: Mar. 14, 2007

(86) PCT No.: PCT/DK2007/000128
§ 371 (c)(1),
(2), (4) Date: Oct. 30, 2008

(87) PCT Pub. No.: WO2007/104314
PCT Pub. Date: Sep. 20, 2007

(65) Prior Publication Data
US 2009/0162945 A1    Jun. 25, 2009

(30) Foreign Application Priority Data
Mar. 14, 2006 (DK) ................ 2006 00400

(51) Int. Cl.
*G01N 33/53* (2006.01)
*G01N 31/00* (2006.01)

(52) U.S. Cl.
USPC ............... 435/7.21; 435/7.1; 436/1; 436/8; 436/501; 436/518; 424/9.1; 424/520; 530/300; 530/350

(58) Field of Classification Search .......... None
See application file for complete search history.

(56) References Cited

FOREIGN PATENT DOCUMENTS

| EP | 1 291 424 A1 | 3/2003 |
|---|---|---|
| WO | WO 2004/043398 A2 | 5/2004 |
| WO | WO 2007/053480 A2 | 5/2007 |

OTHER PUBLICATIONS

Zhongzhou Chen et al., "Structural Insights into Histone Demethylation by JMJD2 Family Members", Cell 125, May 19, 2006, 691-702.
Paul A.C. Cloos et al., "The putative oncogene GASC1 demethylates tri- and dimethylated lysine 9 on histone H3", Nature, Jul. 20, 2006, United Kingdom, vol. 442, No. 7100, pp. 307-311.
Steven G. Gray et al., "Functional Characterization of JMJD2A, a Histone Deacetylase- and Retinoblastoma-binding Protein", The Journal of Biological Chemistry, vol. 280, No. 31, Issue of Aug. 5, 2005, pp. 28507-28518.
Ying Huang et al., "Recognition of Histone H3 Lysine-4 Methylation by the Double Tudor Domain of JMJD2A", Science, vol. 312, May 5, 2006, pp. 748-751.
Masuko Katoh et al., "Identification and characterization of JMJD2 family genes in silica", International Journal of Oncology 24: 1623-1628, 2004.
Jeesun Kim et al., "Tudor, MBT and chromo domains gauge the degree of lysine methylation", EMBO reports vol. 7, No. 4, 2006, pp. 397-403.
Sarah C. Trewick et al., "Methylation: lost in hydroxylation?", EMBO reports, vol. 6, No. 4, 2005, pp. 315-320.
Yu-ichi Tsukada et al., "Histone demethylation by a family of JmjC domain-containing proteins", Nature, vol. 439, Feb. 16, 2006, pp. 811-816.
Johnathan R. Whetstine et al., "Reversal of Histone Lysine Trimethylation by the JMJD2 Family of Histone Demethylases", Cell 125, 467-481, May 5, 2006.
Zeng-Quan Yang et al., "Identification of a Novel Gene, GASC1, within an Amplicon at 9p23-24 Frequently Detected in Esophageal Cancer Cell Lines", Cancer Research 60, 4735-4739, Sep. 1, 2000.

*Primary Examiner* — Lisa Cook
(74) *Attorney, Agent, or Firm* — Foley & Lardner LLP

(57) ABSTRACT

The present invention provides a method of testing the ability of a test compound to bind to and optionally modulate the activity of a protein of the JMJD2 subfamily of Jumonji proteins. The method comprises incubating a test compound with a protein of the JMJD2 subfamily of Jumonji proteins, a co-factor of said protein and, optionally, a substrate for demethylation. The method of the invention can be used for screening large numbers of compounds to identify a group of compounds that are candidate compounds for clinical use for treatment of certain cancers especially prostate cancers. Other compounds that do not have activity in the screening assays can be eliminated from further consideration as candidate compounds. The method of the invention therefore has utility in the pharmaceutical industry.

22 Claims, 33 Drawing Sheets

```
                β9              β10         β11
                ────▶          ────▶      ────▶
GASC1     GMWKTTFAWHTEDMDLYSINYLHFGEPKSWYAIPPEHG
JMJD2A    GMWKTSFAWHTEDMDLYSINYLHFGEPKSWYSVPPEHG
FBXL11    VRGCYT.DFHVDFGGT.SVWYHIHQGGKVFWLIPPTAH
FIH       MEGNVT.PAHYDEQ...QNFPAQIKGYKRCILFPPDQF
EPE1      AENSYT.EFHIEFGGS.SAYYINLDGCKIFYLIPGTSK
               o        * *                    o

β14          β15
              ────▶        ────▶
GASC1     PYGYHAGFNHG.FNCAESTNFATVRWIDYGKVAKLCTC
JMJD2A    PYGYHAGFNHG.FNCAESTNFATRRWIEYGKQAVLCSC
FBXL11    SGWIHAVYTPT.DTLVFGGNFLHSFNIPMQLKIYNIED
FIH       MYWWHHIESLLNGGITITVNFWYKGAPT.PKRIEYPLK
EPE1      SGWIYAVVTPC.DTISIAGNFLTFLHIYPQLSIYNLEL
```

Fig. 5

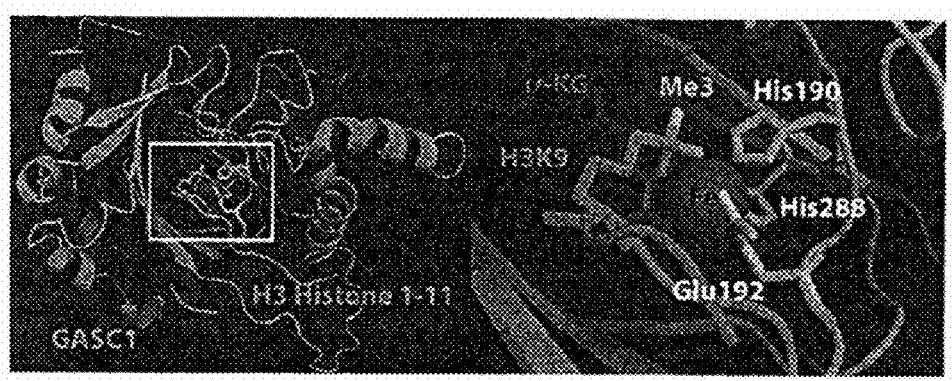
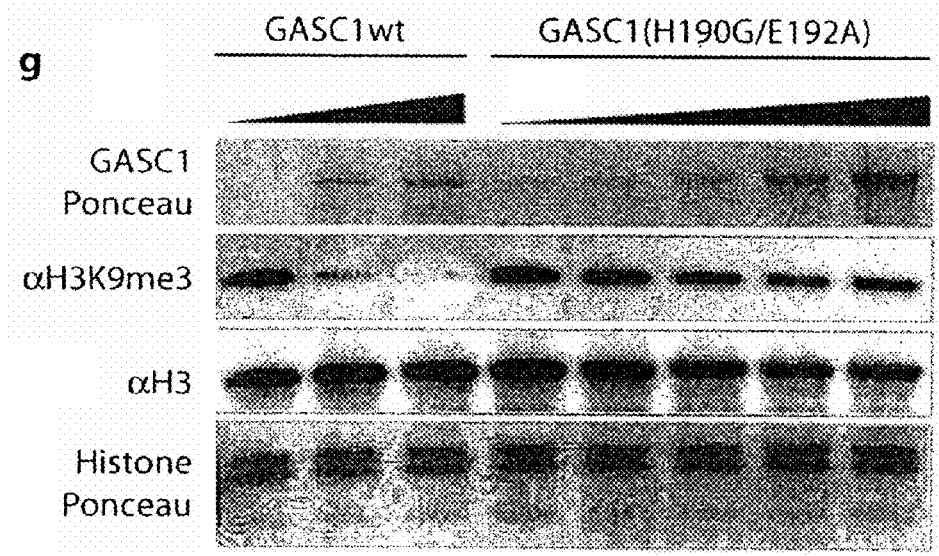
Fig. 6 a

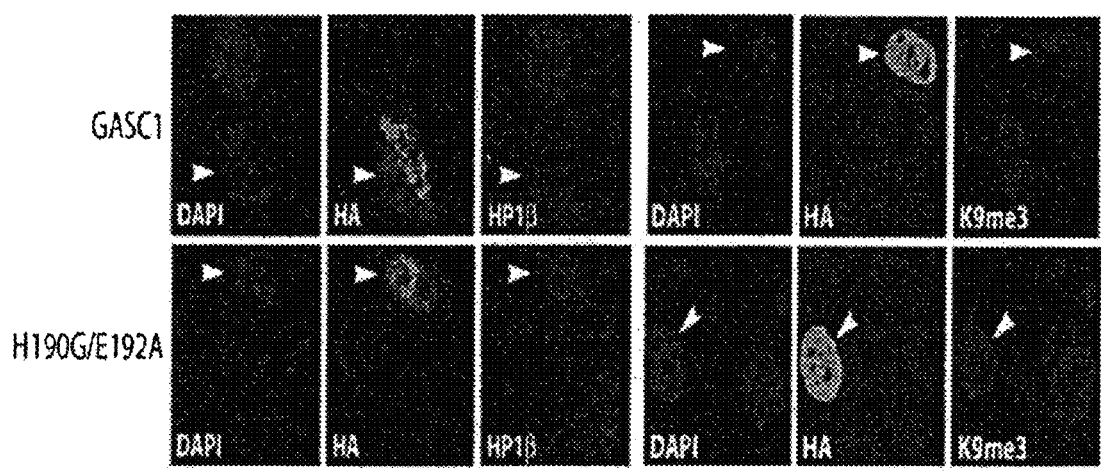
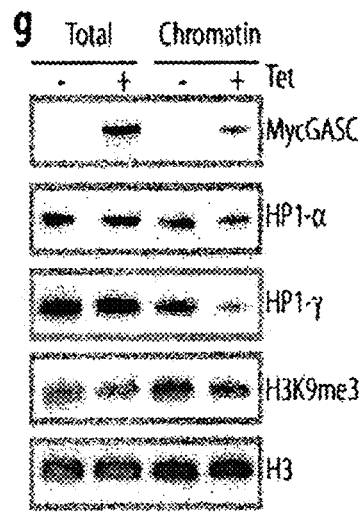
Fig. 11

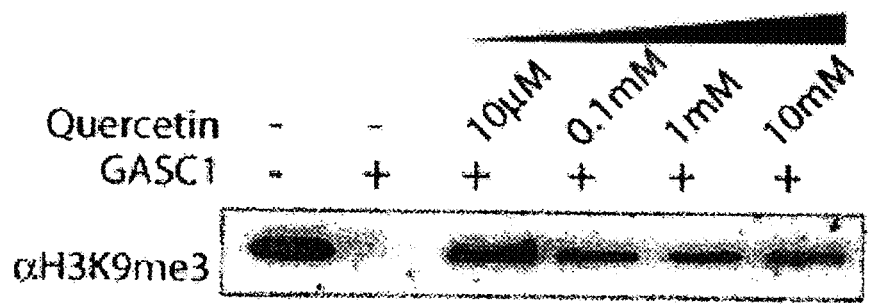
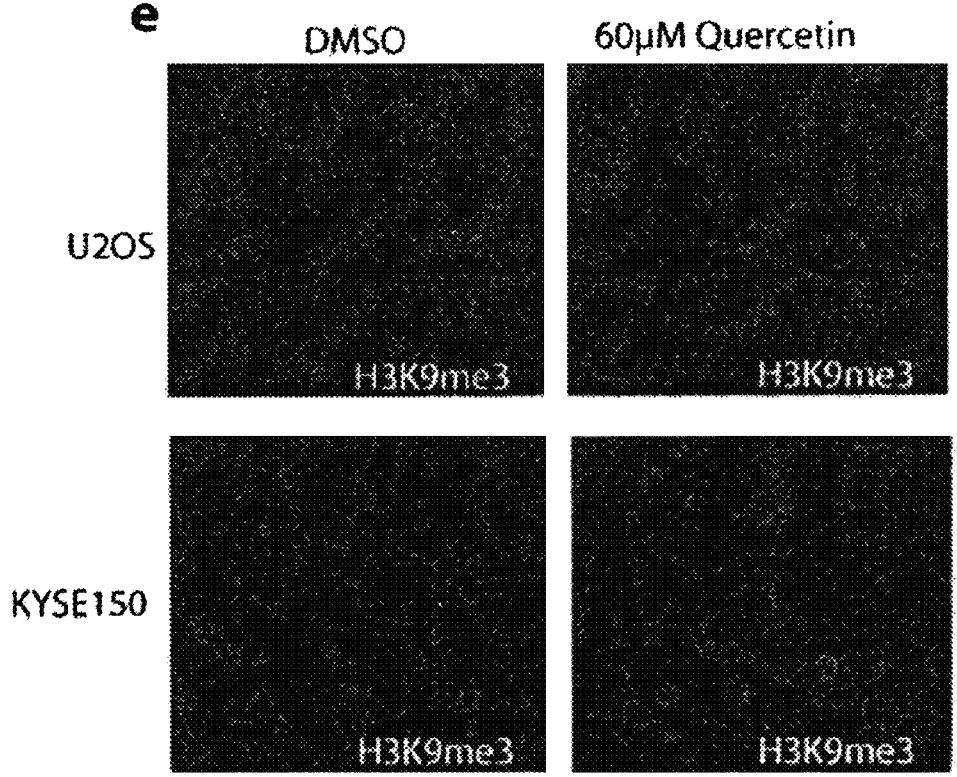
Fig. 13

| | 1 10 20 |
|---|---|
| GASC1/JMJD 2C (144-310) | ------------------------ |
| JMJD 2A (142-308) | ------------------------ |
| JMJD 2B (143-309) | ------------------------ |
| JMJD 2D (146-312) | ------------------------ |
| JARID 1B (489-655) | ------------------------ |
| JARID 1C (468-634) | ------------------------ |
| JARID 1A (437-603) | ------------------------ |
| JARID 1D (458-624) | ------------------------ |
| JMJD3 (1341-1504) | ------------------------ |
| UTX (729-892) | ------------------------ |
| Tetratricopeptide repeat protein isoform 3 (1042-1205) | ------------------------ |
| UTY (1019-1206) | LSLPNSWNYRHLPSCPTNFCIFVET |
| FBXL10 (178-346) | --------------------FSHT |
| FBXL11 (148-316) | --------------------FSHT |
| PHD finger protein 2 (197-353) | --------------------FSDT |
| PHD finger protein 8 (255-411) | --------------------FSDT |
| Similar to PHD finger protein 8 (476-632) | --------------------FSDT |
| PTDSR (143-307) | -----------------------P |
| PH (146-313) | -------------------LYLQQ |
| Hairless protein isoform b (946-1102) | -------------DTSRVENLAASL |
| JMJD1B (1524-1747) | -------------MPTRFEDLMENL |
| Thyroid hormone receptor interactor 8 (820-952) | -------------MPARYEDLLKSL |
| JMJD1A (942-1165) | -------------MPSRFDDLMANI |
| Cytosolic phospholipase a2 beta (128-308) | --------------VQKQCSNLPSE |
| JMJD1C (2037-2261) | --------------VQKQCSNLPSE |
| Mina53 (128-271) | -------------------FDQKR |
| PP14397 (95-234) | -------------------PTSLGN |
| JARID 2 (884-1048) | ------------------------ |
| Consensus | |

Fig. 16

```
                30         40         50         60         70         80
                |          |          |          |          |          |
         ---EGVDEWN AR NT LDV EE----------ECGISIEG NTP  Y G WK TFA
         ---KHVDEWN GR RT LDL EK----------ESGITIEG NTP  Y G WK SFA
         ---DDVAQWN GS RT LDM ER----------ECGTIIEG NTP  Y G WK TFA
         ---ENTKQWN GH GT QDL EK----------ECGVVIEG NTP  Y G WK TFA
         --- LDSGWN NN PV EQS LA----------HITADICG KLP  Y G CF SFC
         --- ATSGWN NV PV EQS LC----------HINADISG KVP  Y G VF AFC
         --- ALSGWN NN PV EQS LA----------HINVDISG KVP  Y G CF SFC
         --- ATSGWN NV PV DQS LC----------HINADISG KVP  Y G VF AFC
         --- KPQLQE LK PA MRV STGNMLS-----HVGHTILG NTVQ Y K PG RTP
         --- KLQLHE TK PA VRV SAGNLLS-----HVGHTILG NTVQ Y K PG RTP
         --- KLQLHE TK PA ARV SAGNLLT-----HVGHTILG NTVQ Y K PG RTP
         GFH VGQACLE LTSGG LAS SQSAGIT----GVSHHAR----LQ Y K PG RTP
         KLE VKRPTV DL DW DNMWPQHLKEKQTEATNAIAEMKYPKVKK C S KG FTD
         RLE MVQRPST DF DW DNMWPRHLKESQTESTNAILEMQYPKVQK C S RG YTD
         RMS VEPPDI KK SW ENYWPDDALLA---------KPKVTK C C KD YTD
         RLS VETPKI RK SW ENLWPEECVFE---------RPNVQK C S RD YTD
         KMS VEVPDI KK SW ENYWPDDSVFP---------KP VQK C G QD YTD
         KRR LEDYKVPKF TDDLFQYAGE----------KRRPPYR   GPPR GTG
         TLN TVGRKIV DF GFNWNW NKQQG---------KRGWGQ TSNL  G EG VTP
         PLP CALHGK NL SY PPG ALRPLEPQLWAAYG-VSPHRGHLGTKN CVEVA LVS
         PLP TKRDGR NL SR PSY VRPDLGPKMYNAYGLITAEDRRVGTTN HLDVS AVN
         PLP CNPEGK NL SH PGF VRPDLGPRLCSAYGVVAAKDHDIGTTN HIEVS VVN
         PLP TRRDGK NL SR PNY VRPDLGPKMYNAYGLITPEDRKYGTTN HLDVS AAN
         LPQL PDLESH PW SE LGK PDAVNFWLGEAAAVTSLHKDHYENL C SGE- HFL
         LPQ LPDLESH PW SE LGK PDAVNFWLGEAAAVTSLHKDHYENL C SGE- HFL
         ATI HQPQRFKDE WR QEK ECYFG----------SL GSNVY  PG-- SQG
         DTL FFGDNNF EW SL RHYSPPP----------FGPLGT PAY F IAGAG GVP
         ---P SRHGWN TV PNNTGS LR----------HLGAVPG TIP LN G VF STSC
            EY    L     L    L    V              M    YLLM M   S
```

Fig. 17

```
              90        100       110       120       130       140
       DMDLY IN  HF E---------------P S      PEHGKR ERLAQGFFP
       DMDLY IN  HF E---------------P S  SV  PEHGKR ERLAKGFFP
       DMDLY IN  HF E---------------P S      PEHGKR ERLAIGFFP
       DMDLY IN  HL E---------------P T      PEHGQR ERLARELFP
       DHWSY IN  HW E---------------P T  G   GYAAEQ ENVMKKLAP
       DHWSY IN  HW E---------------P T  G   SLAAEH EEVMKKLTP
       DHWSY IN  HW E---------------P T  G   SHAAEQ EEVMRELAP
       DHWSY IN  HW E---------------P T  G   SLAAEH EEVMKMLTP
    G  NNNFC VNINIGPG--------------DCE      HEHYWET SAFCDRHGV
    G  NNNFC VNINIGPG--------------DCE      EGYWGV NDFCEKNNL
    G  NNNFC VNINIGPG--------------DCE      EDYWGV NDFCEKNNL
    G  NNNFC VNINIGPG--------------DCE      EDYWGV NDFCEKNNL
       FGGTS WY  FR G---------------       PTLHNLALYEEWVLS-
       FGGTS WY  HQ G---------------       PTAHNLELYENWLLS-
       SGGAS WY  LK E---------------       RPASANISLYERWRSA-
       FGGTS WY  LK E---------------       RPTNANLTLFECWSSS-
       FGGTS WY  LW E---------------       KPTDENLARYESWSSS-
       PLGTS WNA VQ ---------------H R     TSTPRE IKVTRDEGG
    A  DEQQ--NFFAQIK ---------------Y RC   PDQFEC YPYPVHHPC
       ADTPL AW RAQKD-----------------      GLDGEG WSPGSQVS-
    VM YVGIPI EGAHDEE---------------VLK    DEGDADE TKQRIHDGK
       YVGIAK NGI SK G---------------ILKK   EEEDLDD LRKRLKDSS
    VM YVGIPK QC QEEE---------------VLK    QDGDSDE TIKRFIEGK
       PPSDRPFIPY  YTP---------------AT Q   EEGTFKV DEEAMEKA-
       PPSDRPFIPY  YTPGTYQPSDRPFIPYELYTPAT Q EEGTFKV DEEAMEKVP
       PP YDDVE FILQLE E---------------H R  YHPTVPLAREYSVEAEER
        W GPG---YS  IY R---------------     PEKTPE RPNKTTLA-
      R QNHLPYID HT ---------------DCI     AEEENK EDVVHTLLQ
    WHIE     S    YL  G               K    WYLIP      L
```

Fig. 18

```
                150        160       171
         SSSQGCDAFLRHKMTLISPSVLKKYGVPV
         GSAQSCEAFLRHKMTLISPLMLKKYGVPV
         GSSQGCDAFLRHKMTLISPIILKKYGVPV
         GSSRGCGAFLRHKVALISPTVLKENGVPV
         ELFVSQPDLIHQLVTIMNPNTLMTHEVPV
         ELFDSQPDLIHQLVTLMNPNTLMSHGVPV
         ELFESQPDLIHQLVTIMNPNVLMEHGVPV
         ELFDSQPDLIHQLVTLMNPNTLMSHGVPV
         DYLTG-------SWWPILDDIYASNVPV
         NFLMG-------SWWPNLEDIYEANVPV
         NFLMS-------SWWPNLEDIYEANVPV
         NFLMS-------SWWPNLEDIYEANVPV
         -------GKQSDIFLGDRVERCQRIELKQ
         -------GKQGDIFLGDRVSDCQRIELKQ
         -------SNHSEIFFADQVDKCYKCIVKQ
         -------SNQNEIFFGDQVDKCYKCSVKQ
         -------VTQSEIFFGDKVDKCYKCVVKQ
         NQQDEAITWLNVIYPRTQLPTWPPEFKDL
         DRQSQVDFDNPDYERFPNFQNVVGYELVV
         --------TLWHIFRAQDAQRIRRFLQMV
         EKP----GALWHIYAAKDAEKIRELLRKV
         EIP----GALWHIYAGKDVDKIREFL---
         EKP----GALWHIYAAKDTEKIREFLKKV
         EVSRTCLLTIRVIQAHRLPSKDLVTPSDC
         WIPLDPLAPDLARYPSYSQAQALRCMVRI
         ----------------IGRPIHEFMLKP
         ---------------WLRDTYPALPPSARI
         ANGTPG-LQILESNVMISPEVLCKEGIKV
                L    I     L    VPV
```

Fig. 19

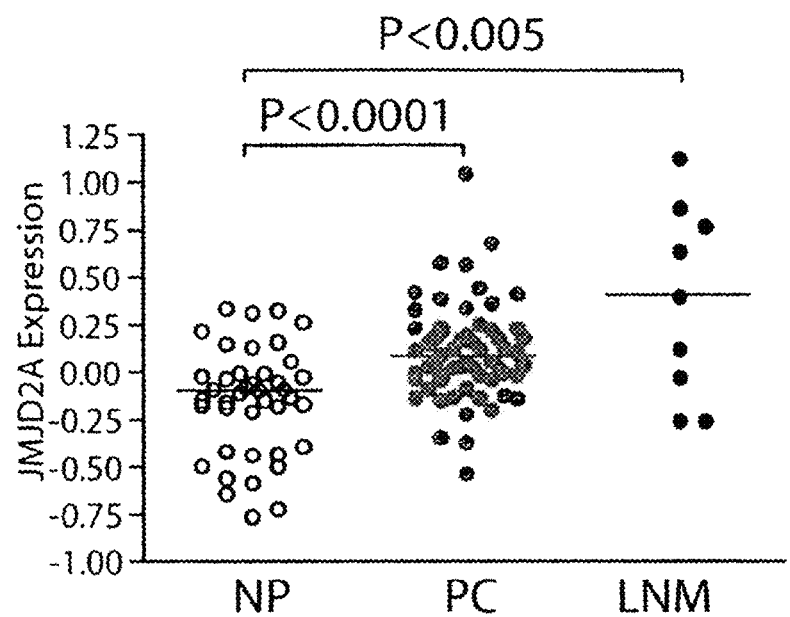
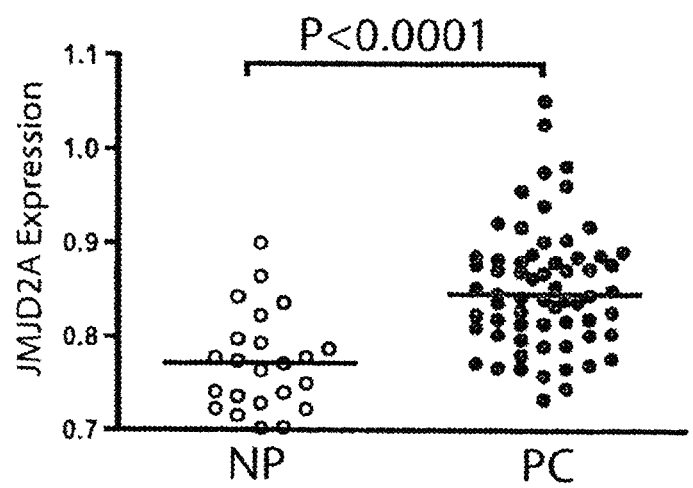
Fig. 32

INHIBITION OF GASC1

FIELD OF INVENTION

The present invention relates to a method for identifying compounds that are capable of acting as activity modulators of the JmjC domain containing proteins and which are useful for prevention and/or treatment of diseases in which genomic instability is involved in the pathogenesis.

BACKGROUND OF THE INVENTION

Methylation of lysine and arginine residues on histone tails constitutes important epigenetic marks delineating transcriptionally active and inactive chromatin. For instance, methylation of lysine 9 on histone H3 (H3-K9) is associated with epigenetically silenced chromatin[1-3]. In contrast to other histone modifications such as acetylation and phosphorylation, methylation has been regarded as irreversible because of the high thermodynamic stability of the N—CH3 bond. Recently however, Shi and coworkers[4] identified the protein LSD1, a nuclear amine oxidase homologue, as a histone demethylase highly specific for mono- and di-methylated H3-K4. This enzyme demethylates its substrates through an amine oxidase reaction. However, LSD1 is unable to demethylate tri-methylated lysine H3-K4, most likely due to the absence of a protonated nitrogen required for oxidation4. Just prior to the completion of the present study, Tsukada et al. demonstrated that the Jumonji protein FBXL11 (JHDM1a) can specifically demethylate di-methyl H3-K36 in a Fe(II) and α-ketoglutarate-dependent manner[5]. Although the reaction mechanism for FBXL11-mediated demethylation at least in theory could utilize tri-methyl H3-K36 as substrate, no such activity could be demonstrated[5]. Thus, although the identification of LSD1 and FBXL11 as histone demethylases constituted important milestones for epigenetic research demonstrating the dynamic regulation of methyl marks, they have not resolved the question of the reversibility of tri-methylated lysine marks.

As documented by studies of the SUV39H1 knockout mouse, loss of the tri-methyl variant of the H3-K9 mark results in chromosomal aberrations and predisposes to cancer. Hence enzymes capable of reversing this mark have long been sought, although their existence has been questioned. The latter view has been reinforced by the fact that tri-methylated H3-K9 is required for the establishment and maintenance of heterochromatin, a "very stable and heritable chromatin state". The identification of such enzymes and inhibitors of their activity would provide a novel approach to the prevention and treatment of cancers.

SUMMARY OF THE INVENTION

The present invention provides a method of testing the ability of a test compound to bind to and optionally modulate the activity of a protein of the JMJD2 subfamily of Jumonji proteins, said method comprising incubating a test compound with a protein of the JMJD2 subfamily of Jumonji proteins, a co-factor of said protein and, optionally, a substrate for demethylation.

In a presently preferred embodiment of the invention, the method comprises the steps of:
i) preparing a suspension of a substrate for demethylation in a solution containing iron and alpha-ketoglutarate;
ii) adding said test compound to the suspension;
iii) adding to said suspension in ii) a protein of the JMJD2 subfamily of Jumonji proteins
iv) incubating said suspension and; and
v) determining the extent of demethylation of said substrate.

DEFINITIONS

The term 'nucleic acid molecule' refers to an oligomer or polymer of ribonucleic acid (RNA) or deoxyribonucleic acid (DNA) or mimetics thereof. This term includes molecules composed of naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids are often preferred over native forms because of desirable properties such as, for example, enhanced cellular uptake, enhanced affinity for nucleic acid target and increased stability in the presence of nucleases and other enzymes, and are in the present context described by the terms "nucleic acid analogues" or "nucleic acid mimics". Preferred examples of nucleic acid mimetics are peptide nucleic acid (PNA-), Locked Nucleic Acid (LNA-), xylo-LNA-, phosphorothioate-, 2'-methoxy-, 2'-methoxyethoxy-, morpholino- and phosphoramidate-containing molecules or the like.

A "polynucleotide sequence" (e.g. a nucleic acid, polynucleotide, oligonucleotide, etc.) is a polymer of nucleotides comprising nucleotides A, C, T, U, G, or other naturally occurring nucleotides or artificial nucleotide analogues, or a character string representing a nucleic acid, depending on context. Either the given nucleic acid or the complementary nucleic acid can be determined from any specified polynucleotide sequence.

With respect to the present invention the term 'polypeptide' refers to an amino acid chain of any length, including a full-length protein, oligopeptides, short peptides and fragments thereof, wherein the amino acid residues are linked by covalent bonds. All polypeptide sequences in the present specification and claims are, also when not explicitly stated, written from the N-terminal to the C-terminal end in the conventional format.

Numbering of a given amino acid polymer or nucleotide polymer "corresponds to" or is "relative to" the numbering of a selected amino acid polymer or nucleic acid polymer when the position of any given polymer component (e.g. amino acid, nucleotide, also referred to generically as a "residue") is designated by reference to the same or an equivalent position in the selected amino acid or nucleotide polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

A "variant" is a polypeptide comprising a sequence, which differs (by deletion of an amino acid, insertion of an amino acid, and/or substitution of an amino acid for a different amino acid) in one or more amino acid positions from that of a parent polypeptide sequence. The variant sequence may be a non-naturally occurring sequence, i.e. a sequence not found in nature.

In the present context, the term "synthetic peptide" refers to a peptide, including a short peptide that has been synthesized in vitro. The term further encompasses peptides or short peptides that have been modified by substitution with unusual or non-natural amino acids.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring. "Non-naturally occurring" as applied to an object means that the object is not naturally-occurring i.e. the object cannot be found in nature as distinct from being artificially produced by man.

A "fragment" or "subsequence" refers to any portion of a given sequence. It is to be understood that a fragment or subsequence of a sequence will be shorter than the sequence itself by at least one amino acid or one nucleic acid residue. Thus, a fragment or subsequence refers to a sequence of amino acids or nucleic acids that comprises a part of a longer sequence of amino acids (e.g. polypeptide) or nucleic acids (e.g. polynucleotide) respectively.

The term 'sequence identity' indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

In all polypeptide or amino acid based embodiments of the invention, the percentage of sequence identity between one or more sequences is based on alignment of the respective sequences as performed by clustalw software (http://www.e-bi.ac.uk/clustalW/index.html) using the default settings of the program. These settings are as follows: Alignment=3Dfull, Gap Open 10.00, Gap Ext. 0.20, Gap separation Dist. 4, Protein weight matrix: Gonnet. With respect to the nucleotide-based embodiments of the invention, the percentage of sequence identity between one or more sequences is also based on alignments using the clustalW software with default settings. For nucleotide sequence alignments these settings are: Alignment=3Dfull, Gap Open 10.00, Gap Ext. 0.20, Gap separation Dist. 4, DNA weight matrix: identity (IUB).

In the present context "complementary sequence" refers to nucleotide sequences which will hybridise to a nucleic acid molecule of the invention under stringent conditions. The term "stringent conditions" refers to general conditions of high stringency. The term "stringency" is well known in the art and is used in reference to the conditions (temperature, ionic strength and the presence of other compounds such as organic solvents) under which nucleic acid hybridisations are conducted. With "high stringency conditions", nucleic acid base pairing will occur only between nucleic acid fragments that have a high frequency of complementary base sequences, as compared to conditions of "weak" or "low" stringency.

As an example, high stringency hybridisation conditions comprise (1) low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) hybridisation in 50% (vol/vol) formamide with 5×Denhardt's solution (0.1% (wt/vol)) highly purified bovine serum albumin/0.1% (wt/vol) Ficoll/0.1% (wt/vol) polyvinylpyrrolidone), 50 mM sodium phosphate buffer at pH 6.5 and 5×SSC at 42° C.; or (3) hybridisation in 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC and 0.1% SDS.

The term "isolated nucleic acid" may refer to a nucleic acid (e.g. DNA or RNA) that is not immediately contiguous with both of the coding sequences with which it is immediately contiguous (i.e. one at the 5' and one at the 3' end) in the naturally occurring genome of the organism from which the nucleic acid of the invention is derived. Thus, this term includes e.g. a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including e.g. a virus, from which it was originally derived, linked to an additional coding sequence to form a hybrid gene encoding a chimeric polypeptide, or independent of any other DNA sequences. The DNA may be double-stranded or single-stranded, sense or anti-sense.

A "recombinant polynucleotide" or a "recombinant polypeptide" is a non-naturally occurring polynucleotide or polypeptide that includes nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is artificial or engineered, or derived from an artificial or engineered polypeptide or nucleic acid. A recombinant nucleic acid (e.g. DNA or RNA) can be made by the combination (e.g. artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" (or "recombinant protein") often refers to a polypeptide (or protein) which results from a cloned or recombinant nucleic acid or gene. The source polynucleotides or polypeptides from which the different nucleic acid or amino acid sequences are derived are sometimes homologous (i.e. have, or encode a polypeptide that encodes, the same or a similar structure and/or function), and are often derived from different isolates, serotypes, strains, species, of organism or from different disease states, for example.

The term "recombinant" when used with reference, e.g. to a cell, nucleotide, vector, protein, or polypeptide typically indicates that the cell, nucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences (e.g. genes) that are not found in the native (non-recombinant) form of the cell or express native nucleic acid sequences (e.g. genes) that would be abnormally expressed under-expressed, or not expressed at all. The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

The term "recombinantly produced" refers to an artificial combination usually accomplished by either chemical synthesis means, recursive sequence recombination of nucleic acid segments or other diversity generation methods (such as, e.g. shuffling) of nucleotides, or manipulation of isolated segments of nucleic acids, e.g. by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo, where it may be expressed or propagated.

"Conservative" as used herein means (i) that the alterations are as conformationally neutral as possible, that is, designed to produce minimal changes in the tertiary structure of the mutant peptide or polypeptides as compared to the native protein. Conformational neutrality is desirable for preserving biological activity. Rules exist which can guide those skilled in the art to make alterations that have high probabilities of being conformationally neutral, see e.g. (77) and (78). Some of the more important rules include (1) replacement of physicochemically similar, i.e. synonymous, residues is less likely to produce conformational changes because the replacing amino acid can play the same structural role as the replaced amino acid; and (2) alteration of evolutionarily conserved sequences is likely to produce deleterious conformational effects because evolutionary conservation suggests sequences may be functionally important.

Unless otherwise defined herein or below in the remainder of the specification, all technical and scientific terms used herein have the same meaning as commonly understood by those of ordinary skill in the art to which the invention belongs.

DETAILED DESCRIPTION OF THE INVENTION

The present invention is based on the discovery that compounds capable of acting as activity modulators of the JmjC domain containing proteins are useful for prevention and/or treatment of diseases in which genomic instability is involved in the pathogenesis. In particular, modulators of the JmjC domain containing proteins are useful for prevention and/or treatment of cancer. The present invention further pertains to the identification of the Jumonji protein; gene amplified in squamous cell carcinoma 1 (GASC1) as a protein capable of interacting with di-methylated and tri-methylated lysine 9 on histone H3 (H3-K9). GASC1 belongs to the JMJD2 subfamily of the Jumonji family. The inventors of the present invention have shown that the JMJD2 family of proteins are histone-demethylases demethylating tri- and di-methylated H3-K9. Furthermore, the inventors have demonstrated that ectopic expression of GASC1 and JMJD2 members dramatically decreases tri- and di-methylated H3-K9, increases mono-methylated H3-K9, delocalises HP1 and reduces heterochromatin in vivo. Thus, in addition to being the first identified histone tri-methyl demethylase, proteins of the JMJD subfamily of the Jumonji family are also involved in cancer development. Inhibitors of the catalytic activity of these enzymes are therefore important candidates for development of novel anti-cancer therapies.

The present invention thus pertains to a method of identifying, screening, characterising or designing a compound which is capable of modulating the activity of a protein of the JMJD2 subfamily of Jumonji proteins. The method of the invention can be used for screening large numbers of compounds to identify a group of compounds that are candidate compounds for clinical use for treatment of certain cancers especially prostate cancers. Other compounds that do not have activity in the screening assays can be eliminated from further consideration as candidate compounds. The method of the invention therefore has utility in the pharmaceutical industry.

According to the present invention a compound which inhibit the binding of a protein of the JMJD2 subfamily of Jumonji proteins to its substrates (histone peptides, histones or nucleosomes) or cofactors (a-ketoglutarate or iron) can be identified in competitive binding assays. Alternatively, the binding of a test compound to a protein of the JMJD2 subfamily of Jumonji proteins, or its substrates or cofactors can be measured directly. This latter type of assay is called a direct binding assay. Both direct binding assays and competitive binding assays can be used in a variety of different formats, similar to the formats used in immunoassays and receptor binding assays generally known in the art. For a description of different formats for binding assays, including competitive binding assays and direct binding assays, see Basic and Clinical Immunology 7th Edition (D. Stites and A. Terr ed.) 1991; Enzyme Immunoassay, E. T. Maggio, ed., CRC Press, Boca Raton, Fla. (1980); and "Practice and Theory of Enzyme Immunoassays," P. Tijssen, Laboratory Techniques in Biochemistry and Molecular Biology, Elsevier Science Publishers B. V. Amsterdam (1985), each of which is incorporated herein by reference.

In competitive binding assays, for example, a test compound compete with a labeled analyte for specific binding sites on a binding agent bound to a solid surface. In this type of format, the labeled analyte can be labeled histone peptides and the binding agent can be a protein of the JMJD2 subfamily of Jumonji proteins which is bound to a solid phase. Alternatively, the labeled analyte can be labeled JMJD2 protein and the binding agent can be a solid phase histone peptide. The concentration of labeled analyte bound to the capture agent is inversely proportional to the ability of a test compound to compete in the binding assay. The amount of inhibition of labeled analyte by the test compound depends on the binding assay conditions and on the concentrations of binding agent, labeled analyte, and test compound that are used. Under specified assay conditions, a test compound is said to be capable of inhibiting the binding of the substrate (i.e. histone peptides) or co-factor to a protein of the JMJD2 subfamily of Jumonji proteins in a competitive binding assay, if the amount of binding of the labeled analyte to the binding agent is decreased by 10% or more. When a direct binding assay format is used, a test compound is said to inhibit the binding the substrate (i.e. histone peptides) or co-factor (i.e. a-ketoglutarate) to JMJD2 enzyme when the signal measured is twice the background level or higher.

In a competitive binding assay, the sample compound competes with labeled protein for binding to a specific binding agent. As described above, the binding agent may be bound to a solid surface to effect separation of bound labelled protein from the unbound labelled protein. Alternately, the competitive binding assay may be conducted in liquid phase, and any of a variety of techniques known in the art may be used to separate the bound labeled protein from the unbound labeled protein. Following separation, the amount of bound labeled protein is determined. The amount of protein present in the sample is inversely proportional to the amount of labelled protein binding.

Alternatively, a homogenous binding assay may be performed in which a separation step is not needed. In these types of binding assays, the label on the protein is altered by the binding of the protein to its specific binding agent. This alteration in the labelled protein results in a decrease or increase in the signal emitted by label, so that measurement of the label at the end of the binding assay allows for detection or quantitation of the protein.

The binding assay formats described herein employ labeled assay components. The label can be in a variety of forms. The label may be coupled directly or indirectly to the desired component of the assay according to methods well known in the art. A wide variety of labels may be used. The component may be labeled by any one of several methods. Traditionally, a radioactive label incorporating 3 H, 125 I, 35 S, 14 C, or 32 P is used. Non-radioactive labels include ligands which bind to labeled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

The terms "histone peptides" and "substrate" refer to those fragments of histones that bind to JMJD2 protein. Methods of production of JMJD2 and histone proteins, for use in screening assays are known to those of skill in the art.

In particular, the method may be a method of testing the ability of a test compound to bind to and optionally modulate the activity of a protein of the JMJD2 subfamily of Jumonji proteins, said method comprising incubating a test compound with a protein of the JMJD2 subfamily of Jumonji proteins, a co-factor of said protein and, optionally, a substrate for demethylation. Particularly, it is within the scope of the present invention to identify a compound which is capable of inhibiting the activity of a protein of the LMJD2 subfamily of Jumonji proteins.

Typically, the method utilise polypeptides of the JMJD2 subfamily of Jumonji proteins and typically a GASC1 polypeptide. In particular, the method utilise a human GASC1 polypeptide or a fragment of this polypeptide, or variants of these. Accordingly, in an important embodiment the invention provides a method, wherein said protein of the JMJD2 subfamily of Jumonji proteins is selected from the group comprising:
 a) the amino acid sequence of SEQ ID NO: 1;
 b) a fragment of the amino acid sequence of SEQ ID NO: 1;
 c) an amino acid having at least 45% sequence identity to either the sequence in a) or the sequence in b), or both.

Cloned members of the JMJD2 subfamily of jumonji proteins include GASC1 (Swis prot accession number Q9H3R0, and its homologues JMJD2a and JMJD2b (Swis prot accession numbers O75164 and O94953, respectively).

An equally important embodiment of the invention pertains to a method, wherein said protein of the JMJD2 subfamily of Jumonji proteins is selected from the group comprising:
 a) the amino acid sequences of SEQ ID NO: 1 (GASC-1 (JM32Dc)), SEQ ID NO: 2 (JMJD2a), SEQ ID NO: 3 (JMJD2b).
 b) a fragment of any one of the amino acid sequences in a);
 c) an amino acid sequence having at least 45% sequence identity to any one of the sequences in a) and/or any one of the sequences in b).

The skilled person will realize that the presently known members of the JMJD2 subfamily of Jumonji proteins are approximately 45% identical by sequence when the amino acid sequences are aligned to a best fit. Therefore, for the present application the amino acid sequences used are at least 45% identical to the sequence of any of the members of the JMJD2 subfamily of Jumonji proteins. In particular, the sequence identity may be at least 45%, such as at least 46%, 47%, 48%, 49%, 50%, 52.5%, 55%, 57.5%, 60%, 62.5%, 65%, 67.5%, 70%, 72.5%, 75%, 77.5%, 80%, 82.5%, 85%, 87.5%, 90%, 92.5%, 95%, 97.5%, 98%, 98.5%, 99% or 99.5%.

In order to incorporate the functional features of the native polypeptide members of the JMJD2 subfamily of Jumonji proteins it is further preferred that the fragments are of at least 100 amino acids, such as at least 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 320, 340, 360, 380, 400, 420, 440, 460, 480, 500, 520, 540, 560, 580, 600, 620, 640, 660, 680, 700, 750, 800, 850, 900, 950, 1000, or at least 1050 amino acids.

Preferably, the fragments are of at least 150 amino acids, such as at least 151, 152, 153, 154, 155, 156, 157, 158, 159, 160, 162, 164, 166, 168, 170, 172, 174, 176, 178, 180, 182, 184, 186, 188, 190, 192, 194, 196, 198 or 200 amino acids.

The present invention further contemplates analogues of the amino acid sequences formed by conservative amino acid substitution. The principle behind conservative amino acid substitution is that certain amino acid pairs have compatible side chains such that, when one amino acid is substituted for the other, there will be only minimal changes in the tertiary structure of the peptide. Rules for conservative substitutions are explained in Bowie et al. Science 247 (1990) 1306-1310. It is an object of the present invention to utilise polypeptides, fragments and variants that retain the ability of the JMJD2 subfamily proteins to bind substrate. In some preferred embodiments it is also preferred that the polypeptides, fragments and variants retain the ability of the JMJD2 subfamily proteins to bind co-factors, including α-ketoglutarate.

Where required, each of the polypeptides, fragments and variants, where required, may be provided either in purified or un-purified form, for example as cellular extracts or by purification of the relevant component from such extracts. Alternatively, the polypeptides, fragments and variants can be recombinantly produced by recombinant expression techniques, and purified for use in the assay. Alternatively, the polypeptides, fragments and variants can be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail in the examples of the present application. Promoter sequences may be inducible or constitutive promoters depending on the selected assay format.

There are a number of common structural features found in the JMJD2 subfamily of Jumonji proteins. These include the JmjN, JmjC, PHD and Tdr sequences, one or more of which are preferred features of the JMJD2 jumonji proteins. These functional domains are characterised by the presence of certain particular amino acid residues located at key positions in the amino acid sequence. While not readily distinguishable when merely inspecting the amino acid sequence of a protein by eye, these domains may be determined using the SMART program (http:/smart.embl-heidelberg.de/smart). The algorithm on which the SMART program is based are described in further details in Letunic et al.[58] and Schultz et al.[59]

Accordingly, in a preferred embodiment of the invention the protein of the JMJD2 subfamily of jumonji proteins as well as the polypeptides, fragments and variants comprise one or more amino acid sequences selected from the group consisting of JmjN-, JmjC-, PHD and TUDOR domains from Jmjd2a:

JmjN (AA 13-55):
(SEQ ID NO: 4)
RIMTFYPTMEEFRNFSRYIAYIESQGAHRAGLAKVVPPKEWKP

JmjC (AA 142-308):
(SEQ ID NO: 5)
EKHVDEWNIGRLRTILDLVEKESGITIEGVNTPYLYFGMWKTSFAWHTED

MDLYSINYLHFGEPKSWYSVPPEHGKRLERLAKGFFPGSAQSCEAFLRHK

MTLISPLMLKKYGIPFDKVTQEAGEFMITFPYGYHAGFNHGFNCAESTNF

ATRRWIEYGKQAVLCSC

PHD (AA 709-767):
(SEQ ID NO: 6)
MCFTSTGCSTDINLSTPYLEEDGTSILVSCKKCSVRVHASCYGVPPAKAS

EDWMCSRCS

PHD (AA 829-885):
(SEQ ID NO: 7)
KCIFCKKRRKRTAGCCVQCSHGRCPTAFHVSCAQAAGVMMQPDDWPFVVF

ITCFRHK

TUDOR (AA 897-954):
(SEQ ID NO: 8)
QSITAGQKVISKHKNGRFYQCEVVRLTTETFYEVNFDDGSFSDNLYPEDI

VSQDCLQF

TUDOR (AA 955-1011):
(SEQ ID NO: 9)
GPPAEGEVVQVRWTDGQVYGAKFVASHPIQMYQVEFEDGSQLVVKRDDVY

TLDEELP

In an equally preferred embodiment of the invention the protein of the JMJD2 subfamily of jumonji proteins as well as the polypeptides, fragments and variants comprise one or more amino acid sequences selected from the group consisting of JmjN-, JmjC-, PHD and TUDOR domains from Jmjd2b:

JmjN (AA 14-56):
(SEQ ID NO: 10)
KIMTFRPTMEEFKDFNKYVAYIESQGAHRAGLAKIIPPKEWKP

JmjC (AA 143-309):
(SEQ ID NO: 11)
DDDVAQWNIGSLRTILDMVERECGTIIEGVNTPYLYFGMWKTTFAWHTED

MDLYSINYLHFGEPKSWYAIPPEHGKRLERLAIGFFPGSSQGCDAFLRHK

MTLISPIILKKYGIPFSRITQEAGEFMITFPYGYHAGFNHGFNCAESTNF

ATLRWIDYGKVATQCTC

PHD (AA 731-789):
(SEQ ID NO: 12)
MCFTSGGENTEPLPANSYIGDDGTSPLIACGKCCLQVHASCYGIRPELVN

EGWTCSRCA

PHD (AA 851-907):
(SEQ ID NO: 13)
KCVYCRKRMKKVSGACIQCSYEHCSTSFHVTCAHAAGVLMEPDDWPYVVS

ITCLKHK

TUDOR (AA 917-974):
(SEQ ID NO: 14)
RAVSLGQVVITKNRNGLYYRCRVIGAASQTCYEVNFDDGSYSDNLYPESI

TSRDCVQL

TUDOR (AA 975-1031):
(SEQ ID NO: 15)
GPPSEGELVELRWTDGNLYKAKFISSVTSHIYQVEFEDGSQLTVKRGDIF

TLEEELP

In embodiments of the invention which currently are the most preferred the protein of the JMJD2 subfamily of jumonji proteins as well as the polypeptides, fragments and variants comprise one or more amino acid sequences selected from the group consisting of JmjN-, JmjC, PHD and TUDOR domains from Jmjd2 (GASC1):

JmjN (AA 15-57):
(SEQ ID NO: 16)
KIMTFRPSMEEFREFNKYLAYMESKGAHRAGLAKVIPPKEWKP

JmjC (AA 144-310):
(SEQ ID NO: 17)
DEGVDEWNIARINTVLDVVEEECGISIEGVNTPYLYFGMWKTTFAWHTED

MDLYSINYLHFGEPKSWYAIPPEHGKRLERLAQGFFPSSSQGCDAFLRHK

MTLISPSVLKKYGIPFDKITQEAGEFMITFPYGYHAGFNHGFNCAESTNF

ATVRWIDYGKVAKLCTC

PHD (AA 689-747):
(SEQ ID NO: 18)
MCFIYSEENIEYSPPNAFLEEDGTSLLISCAKCCVRVHASCYGIPSHEIC

DGWLCARCK

PHD (AA 809-865):
(SEQ ID NO: 19)
KCIFCRHRVKRVSGACIQCSYGRCPASFHVTCAHAAGVLMEPDDWPYVVN

ITCFRHK

TUDOR (AA 877-934):
(SEQ ID NO: 20)
KVISVGQTVITKHRNTRYYSCRVMAVTSQTFYEVMFDDGSFSRDTFPEDI

VSRDCLKL

TUDOR (AA 935-991):
(SEQ ID NO: 21)
GPPAEGEVVQVKWPDGKLYGAKYFGSNIAHMYQVEFEDGSQIAMKREDIY

TLDEELP

It should be acknowledged that the amino acid sequences of these domains may be altered by substitution without loosing function. Comprised by the present invention therefore are protein of the JMJD2 subfamily of jumonji proteins as well as the polypeptides, fragments and variants comprise one or more amino acid sequences which are at least 75% identical to any one of the sequences above, such as at least 80%, 85%, 90%, 95%, 98%, 99%, or at least 99.5% identical to any of the above sequences.

It is to be understood that the protein of the JMJD2 sub-family of jumonji proteins and a potential modulator of the activity may be incubated together under conditions which in the absence of any inhibitor of the enzyme activity provide for de-methylation of lysine 9 on histone H3. Since GASC1 is a Fe(II)- and α-ketoglutarate dependent de-methylase, the protein of the JMJD2 subfamily of Jumonji proteins is typically contacted with a substrate in the presence of a co-substrate. Typically, α-ketoglutarate, Fe(II) and ascorbic acid are used as the co-substrate, but it is within the scope of the present invention to use other co-substrates.

Various approaches to determining the activity of a protein of the JMJD2 sub-family of jumonji proteins and of the polypeptides, fragments and variants described above are available to the skilled person, including measurements of substrate and/or co-substrate utilization as well as measurement of product and/or by-product formation. In particular embodiments of the invention, the method thus comprises the additional steps of:
 a) monitoring in a test sample any of the following parameters:
  i) the methylation state of the substrate;
  ii) the release of formaldehyde;
  iii) the carboxylation state of an α-ketoglutarate substrate co-factor;
  iv) the oxygen consumption
 b) comparing the values obtained for the test sample in step a) with values obtained for a control sample, thereby determining the ability of the test compound to modulate the activity of a protein of the JMJD2 subfamily of Jumonji proteins.

Additionally, the method of the invention may incorporate measurements of any downstream effects of the factors mentioned above. In particular, since GASC action may affect transcription of certain genes it is possible to envision the use of gene reporter assays for measuring GASC activity. Such assays may rely on the measurements of activation of transcription of genes that are naturally repressed by a protein of the JMJD2 subfamily of Jumonji proteins. In addition, one may contemplate in vitro assays relying on the use genetically engineered reporter constructs including a promoter that is subject to methylation and a transcriptionally linked reporter gene.

In particular embodiments these reporter assays may involve the use of a gene which encodes a fluorescent reporter; currently one of the most commonly used fluorescent reporters is Green Fluorescent Protein (GFP).

Determination may be quantitative or qualitative. Both quantitative and qualitative determinations may, as stipulated above, be carried out in the presence of a control. If a control is used it may, depending on which assay method is used, be provided by the following steps:
 a) Incubating a protein of the JMJD2 subfamily of Jumonji proteins and a substrate for demethylation under conditions allowing demethylation
 b) monitoring any of the following parameters in a test sample:
  i) the methylation state of the substrate;
  ii) the release of formaldehyde in a test sample;
  iii) the carboxylation state of an a-ketoglutarate substrate co-factor;
  iv) the oxygen consumption In some embodiments of the present invention the incubation time and methylation state of the substrate and/or the release of formaldehyde are used to determine a rate of demethylation, which is used for comparison.

As the natural substrate for GASC1 is histone H3 it will be understood that in some embodiments of the invention the substrate for demethylation comprises a methylated site corresponding to lysine 9 on histone H3. In a particular embodiment of the invention the substrate for demethylation is a peptide comprising the amino acid sequence of SEQ ID NO: 22 (TARKSTG).

The lysine residue in said amino acid sequence (SEQ ID NO: 22) corresponding to Lys9 in Histone H3 is methylated. In most embodiments of the invention it is preferred that the lysine residue is tri-methylated, but assays may also be performed wherein said lysine residue is di- or mono-methylated.

Currently, as a substrate it is preferred to use a peptide, such as a synthetic peptide, comprising N-terminal residues 6-12 of histone H3, such as residues 5-9, 4-10, 3-10, 2-11, 1-12, 1-13, 1-14, 1-15, 1-20, 1-25, 1-30, 1-35, 1-40, 1-45, 1-50, 1-55, 1-60, 1-65, 1-70, 1-75, 1-80, 1-85, 1-90, 1-95 or 1-100 of histone H3. In the present application the full sequence of Histone H3 is provided in SEQ ID NO.: 23

In accordance with the above description of the substrate for demethylation, it is preferred that said substrate is a peptide of at least 6 amino acid residues, such as at least 7, 8, 9, 10, 11, 12, 13, 14, 15, 16, 17, 18, 19, 20, 21, 22, 23, 24, 25, 26, 27, 28, 29, 30, 32, 34, 36, 38, 40, 45, 50, 60, 70, 80, 90, 100, 120, 140, 160, 180, 200, 250, 300 350, 400, 500, 600, 700, 800, 900 or such as least 1000 amino acid residues. A peptide of 80 amino acid residues or less is conveniently obtained through chemical synthesis using commercially available services or apparatus.

The skilled artisan will realize that peptides which are at least 75% identical to the N-terminal residues of histone H3 as specified above, such as at least 77.5%, 80%, 82.5%, 85%, 87.5%, 90%, 92.5%, 95%, 97.5%, 98%, 98.5%, 99% or 99.5% identical to the N-terminal residues of histone H3. The peptides may incorporate substitutions as explained in detail above for the protein of the JMJD2 subfamily of Jumonji proteins. In particular, conservative substitutions may be preferred, following the same principles as described above.

In further preferred embodiments of the invention, as a minimum, the substrate comprises an amino acid sequence selected from the group consisting of:

In a currently most preferred embodiment, a synthetic peptide 43 amino acids long mimicking the N-terminal tail (1-40) of histone H3, ARTKQTARKSTGGKAPRKQLAT-KAARKSAPATGGVKKPHR (SEQ ID NO: 24) is used as a substrate.

It may further be preferred to use a substrate selected from the group consisting of: bulk histones, synthetic peptides, and nucleosomes.

As mentioned above the method of the invention may be performed with a substrate, wherein the methylated site is mono-methylated, di-methylated or tri-methylated As mentioned above, α-ketoglutarate serves as a co-factor of GASC1 and is therefore be required in the method according to the invention. It is further within the scope of the invention to use as co-factor an analogue of a-ketoglutarate. Additionally, the GASC1 catalytic activity benefits from the presence of ascorbic acid, and in addition to α-ketoglutarate, Fe(II) ions may be important as a co-factor. Accordingly, in a preferred embodiment of the invention the compound and said protein of the JMJD2 subfamily of Jumonji proteins are also incubated with Fe(II) ions, and/or ascorbic acid. It is to be understood that the presence of ascorbic acid is not essential, but ascorbic acid may be needed in order to obtain the full catalytic activity since it converts the iron present in the reaction to the appropriate form, Fe(II).

A cell-free system may be applied when testing compounds acting directly on a protein of the JMJD2 subfamily of Jumonji proteins. The test system is contacted with the test compound and the ability of the test compound to regulate activity of said protein of the JMJD2 subfamily of Jumonji proteins is determined by measuring substrate (nucleosomes, histones or histone-peptides) conversion utilizing an immunoassay.

The peptide substrate of the protein of the JMJD2 subfamily of Jumonji proteins, or the product of its catalytic activity, may for instance be immobilised, e.g. on a plate or bead, and the methylation state or the de-methylation of the appropriate methylated site detected using an antibody or other binding molecule which binds the peptide with different affinity depending on the methylation state. Accordingly, immunological binding partners, which recognize either tri-, di- or mono-methylated histone H3-K9 constitute a part of the test system and will enable a fast determination of a compounds effect on the activity. Such binding partners, including substrate- and product-specific antibodies, are commercially available.

Assay methods of the present invention may also take the form of an in vivo assay. The in vivo assay may be performed using cell based, organ based or whole animal assays. Preferably, the in vivo assay is performed in a cell based system, for instance using a cell line in which the relevant polypeptides or peptides are expressed from one or more vectors introduced in the cell. The cell may, for example, be a yeast cell or a cell of mammalian origin.

In addition, the in vivo assays used in relation to the present invention may rely on isolated cells/primary cells or tissue sections. In a particular interesting embodiment the in vivo assay involves the use of the KYSE-150 cell line, which is a human esophageal squamous cell carcinoma established from the poorly differentiated esophageal squamous cell carcinoma resected from upper (cervical) esophagus of a 49-year-old Japanese woman after receiving radiotherapy (tumor was invading contiguous structures); described as carrying amplified oncogenes, c-erb-B (8×) and cyclin D1 (4×) and producing tumors in nude mice confirmed as human with IEF of AST, LDH, MDH Measurements of the methylation state may, as presently preferred, be combined with the release of formaldehyde-$^3$H by fluorography. A similar technique for measuring formaldehyde release by a formaldehyde-dehydrogenase coupled assay is also contemplated in the present invention.

In preferred embodiments of the invention the methylation state of the substrate and/or the release of formaldehyde and/or the carboxylation state of an α-ketoglutarate substrate co-factor and/or the oxygen consumption are measured by immunoassays (ELISA, RIA, IRMA, TRIFMA), immuno-precipitation, western blotting, BIAcore, x-ray crystallography, in solution NMR, mass-spectrometry, spectroscopic or fluorescence techniques.

In a currently preferred embodiment of the invention, the measurements of substrate utilization and/or product formation is performed by immunofluorescence analyses, preferably by confocal immunostainings. In the presently most preferred embodiments of the invention the peptide substrate is linked to biotin as explained in the examples.

When measuring the methylation state in assays relying on substrate specific antibodies a decreased level of binding of the immunological binding partner, as compared to suitable controls, means a decrease in tri- or di-methylated H3-K9 which correlate with an increase in the activity of a protein of the JMJD2 subfamily of Jumonji proteins. Binding of the immunological binding partner can be assessed by techniques generally know in the art, for example Western blot, ELISA, RIA, TRIFMA, immuno-precipitation or histology. Preferred techniques comprise high-throughput screening techniques as Fluorescence Polarisation, Time Resolved Fluorescence Resonance, energy Transfer Assay (TR-FRET), Scintillation Proximity Assay and "Fluorescence Quenching" Assay. The expression can be coupled to an easy detectable reporter protein, such as, but not limited to, β-galactosidase, chloramphenicol acetyltransferase (CAT), Green Fluorescent Protein, or luciferase.

For competition measurements a synthetic or natural occurring histone peptide might be supplied either in a labelled or unlabelled form. The antibodies may be used with or without modifications. The antibodies may be labelled by joining them, either covalently or non-covalently, with a reporter molecule. Suitable reporter molecules or labels, which may be used for ease of detection, include radionucleotides, enzymes, fluorescent molecules, chemiluminescent, or chromogenic agents as well as substrates, cofactors, inhibitors, magnetic particles, and the like. Antibodies or synthetic peptides of the kit might be immobilised, preferably on a solid surface like a micro-titter plate, possibly by conjugation to a suitable protein carrier like BSA, thyroglobulin, ovalbumin or keyhole limpet hemocyanine.

In a presently preferred embodiment of the invention, the method comprises the steps of:
i) preparing a suspension of a substrate for demethylation as defined in any of claims 8-13 in a solution containing iron and alpha-ketoglutarate;
ii) adding said test compound to the suspension;
iii) adding to said suspension in ii) a protein of the JMJD2 subfamily of Jumonji proteins as defined in any of claims 2-4;
iv) incubating said suspension, preferably at a temperature of 35-38° C. for 10 minutes or more; and
v) determining the extent of demethylation of said substrate.

It is further preferred that the extent of demethylation is assayed using an immunological binding partner specific for histone H3 methylated at lysine 9.

Also, it is preferred that said immunological binding partner is an anti trimethylated histone H3-K9 antibody. Equally preferred is the use of an anti dimethylated histone H3-K9 antibody as the immunological binding partner.

In a further preferred embodiment, the extent of demethylation is assayed using the release of formaldehyde. Further, the extent of demethylation may be assayed by measuring consumption of oxygen.

Alternatively, the extent of demethylation is assayed by measuring the carboxylation state of an α-ketoglutarate substrate co-factor.

As an example the buffer in i) comprises a final concentration of 50 mM Hepes pH 7.5, 50 mM KCl, 4 mM $MgCl_2$, 1 mM α-ketoglutarate, 40 μM $FeSO_4$, 2 mM ascorbic acid. For practical reasons it is further preferred that the suspension has a total volume of 10-50 μl.

Finally, in addition, in order to minimize degradation of the protein components of the reaction it may be advantageous to add one or more protease inhibitors to a final concentration of 1-5 μg/μl. As an example, aprotinine and leupeptine may be included as protease inhibitors.

With respect to the above description of the various aspects of the present invention and of the specific embodiments of these aspects it should be understood that any feature and characteristic described or mentioned above in connection with one aspect and/or one embodiment of an aspect of the invention also apply by analogy to any or all other aspects and/or embodiments of the invention described.

When an object according to the present invention or one of its features or characteristics is referred to in singular this also refers to the object or its features or characteristics in plural. As an example, when referring to "a polypeptide" it is to be understood as referring to one or more polypeptides.

Throughout the present specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The expression of the JMJD2 family of histone demethylases is increased in prostate carcinoma. For detail, please see: a. Data from Lapointe et al (2004) PNAS 101:811-816. The study includes 62 primary prostate tumors (PC, 61 adenocarcinomas and one adenoid cystic tumor), 41 matched normal prostate tissues (NP, from the noncancerous region of the prostate), and nine unmatched (i.e. different patient) pelvic lymph node metastases (LNM). Gene expression profiling was performed by using cDNA microarrays containing 26,260 different human genes (UniGene clusters). Additional details of the study including pathological and clinical data are available at Oncomine (www.oncomine.org) or on the PNAS web site (www.PNAS.org). Bars indicated medians. P-values Mann-Withney U-test (one-tailed) are provided. b. Data from Yu et al J Clin Oncol (2004) 22:2790-2799. The study comprises human samples from men of various ages, included prostate tumors (PC, completely free of normal prostate acinar cells) and normal prostate tissues (NP, adjacent to tumor free of tumor cells). Gene expression profiling was performed by using the Affymetrix (Santa Clara, CA) U95a, U95b, and U95c chip sets (37,777 genes and expression sequence tags). Additional details of the study are available at the Oncomine web site (www.oncomine.org). Bars indicated medians. P-values Mann-Withney U-test (one-tailed) are provided.

BRIEF DESCRIPTION OF THE DRAWINGS

FIG. 3-6: GASC1 demethylates tri- and di-methylated histone H3K9. a, Purification of recombinant GASC1 by size exclusion chromatography. 0.5 ml fractions were collected and 10 μl of the material was incubated with bulk histones for 30 min. at 37° C. Demethylation activity was assayed by blotting for tri-methylated H3K9. b, Demethylation assay using selected fractions (F4, F6, F8, F9, F10, F1, F12, F14, F16) from the size-exclusion chromatography of GASC1. Fractions were assayed for demethylating activity by immunoblotting as indicated. c, Mass spectrometric analysis of demethylation of a H3K9me3 peptide (ARTKQTARKSTG-GKAPRKQLATKAARKSAPATGGVKKPHRYC-Ttds-K(Biotin)-NH2) by purified GASC1. The peptide was analyzed by LC-MS on a LTQ-FT after treatment with GASC1 (+GASC1) and without GASC1 (−GASC1). The deviations of the measured, mono-isotopic masses from the calculated masses are given in brackets. The calculated neutral masses are H3K9me1: 5130.885 Da, H3K9me2: 5144.900 Da, H3K9me3: 5158.916 Da, mass difference as result of demethylation: 14.016 da H3K9 (unmethylated) was not observed. The multiplicity of the individual peaks is caused by the natural occurrence of different isotopes as simulated by IsoPro 3.0 (http://members.aol.com/msmssoft/) for our peptide (molecular formula $C_{223}H_{390}N_{75}O_{61}S_2$), charge state +10 and resolution 50,000 (simulated spectrum). d, Demethylation assay using recombinant GASC1 and synthetic tri-methylated H3K9 peptides as substrates. Peptides are incubated with 6 μg His-GASC1 in the presence of co-factors for 30 min. at 37° C., one third of the material was analyzed by western blotting, the rest was used for mass spectrometry analysis (FIG. 2e). e, Alignment of the JmjC domains of the human Jumonji proteins GASC1, JMJD2A, FIH and FBXL11 and the fission yeast Jumonji protein Epe1. Yellow highlighting indicates similar or identical amino acids. Black, red asterisks indicate residues predicted to be involved in iron binding and a-ketoglutarate, respectively. A green asterisks indicates residues mutated in GASC1 iron-binding mutants. Arrows indicate strands of the double-stranded β-helix numbered corresponding to β-strands 8-15 of FIH, as defined by the PDB sum entry for 1 h2k. f Predicted structure of GASC1 (blue) in complex with the tri-methylated H3 histone tail (1-11) (green) and its co-factors α-ketoglutarate (red) and iron (magenta), the lysine H3K9 methyl groups are marked in yellow. Left panel shows an overview, right panel shows a magnification of the iron-binding residues His190, His288, Glu192, (white sticks). g, Demethylation assay using varying amounts of wild-type and mutant (H190G/E192A) GASC1, using bulk histones as substrate.

FIG. 9-11: Ectopic expression of GASC1 leads to loss of H3K9 di- and tri-methylation in vivo. a, Confocal microscopy of Tig-3 cells transduced with pBabe-GASC1. Tri-methylated H3K9 is lost in Tig-3 cells over-expressing GASC1. White arrows indicate cells expressing HA-tagged GASC1. b, Loss of the ability to demethylate tri-methylated H3K9 in U2OS cells expressing the GASC1H190G/E192A mutants, evaluated by immunofluorescence. White arrows indicate cells expressing HA-tagged GASC1 or expressing the HA-tagged H190G/E192A GASC1 mutant. c, Loss of the ability to demethylate tri-methylated H3K9 in U2OS cells transfected with H190G/E192A GASC1 mutant, evaluated by western blotting. d, Loss of tri- and di-methylated H3K9 and increase of mono-methylated H3K9 in U2OS cells over-expressing JMJD2a. e, Loss of tri- and di-methylated H3K9 and increase of mono-methylated H3K9 in U2OS cells over-expressing JMJD2b. f, Confocal microscopy of 3T3 cells transfected with HA-tagged GASC1 or the HA-tagged H190G/E192A GASC1 mutant. White arrows indicate cells expressing HA-tagged proteins. HP1 is delocalized in cells over-expressing GASC1. g, Western blotting of total lysate and chromatin bound fraction from HEK 293 cells with tetracycline-(Tet) inducible GASC1-expression (Myc-tagged). Addition (+) or omission (−) of Tet as indicated.

FIG. 12-14: GASC1 expression induces growth and is positively correlated with tumourigenicity. a, Transfection of KYSE-150 and KYSE-450 with siRNA to GASC1 or scrambled siRNA control. The relative amount of GASC1 messenger RNA was determined by real-time quantitative RT-PCR. b, Transfection of KYSE-150 with LMP-GASC1 or empty LMP vector followed by selection for 3 days. The relative amount of GASC1 messenger RNA was determined by real-time quantitative RT-PCR. c, Binding mode of quercetin at the Fe(II) active site of GASC1. d, Demethylation assay using recombinant GASC1 and bulk histones as substrates. Histones were incubated with His-GASC1 in the presence of co-factors (FeSO$_4$ and α-ketoglutarate) for 30 min. at 37° C., in the presence or absence of varying amounts of quercetin. The methylation status was evaluated by western blotting. e, Effect of quercetin on the H3K9me3 methylation status of KYSE-150 and U2OS cells as evaluated by immunofluorescence. f, Model for the involvement of GASC1 in cancer development.

FIG. 16-19 (S2): Alignment of the JmjC domain human Jumonji proteins. Proteins were aligned using Vector NTI applying a Clustal W algorithm. Conserved residues, blocks of similar residues and identical residues are shaded in grey. Numbers in parenthesis indicates residue number within the protein.

FIG. 31-33 (S10): H3K9me3 demethylation activity of various GASC1 deletion mutants. a. Schematic representation of generated GASC1 deletion mutants used in the present study, numbers in parentheses indicate deleted residues b, Demethylation activity of wildtype GASC1 and GASC deletion mutants evaluated by immunofluorescence.

EXAMPLES

In an effort to identify proteins interacting with tri-methylated variants of H3K9, HeLa nuclear proteins were affinity purified using biotinylated H3 peptides immobilized on streptavidin-agarose. Synthetic 43-mers mimicking the whole N-terminal tail of histone $H3_{1-40}$, either un-methylated or tri-methylated at lysine 9, were used in the in vitro binding experiments. Bound proteins were eluted from the agarose-matrix, separated by SDS PAGE, silver stained and identified by mass spectrometry. Several proteins were specifically enriched on tri-methylated H3K9 as compared to un-methylated H3K9, supplementary figure S1.

Figure 1:
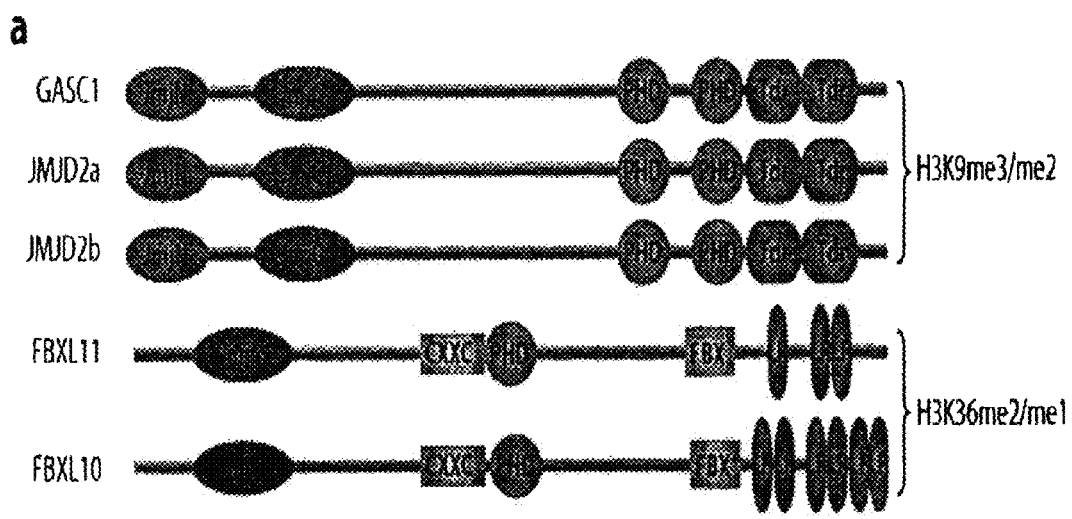
FIG. 1-2: Jumonji histone demethylases GASC1, FBXL11 and their human homologues. a, Diagram of the GASC1, FBXL11 and their human homologues with their domains: JmjC—Jumonji C domain, JmjN—Jumonji N domain, Tdr—Tudor domain, PHD—Plant homeodomain. CXXC—CxxC zinc finger domain, FBX—Fbox domain, LR—Leucine rich repeat. Functional domains are determined using the SMART program (http:/smart.embl-heidelberg.de/smart). b, Phylogenetic tree of the human JmjC-domain containing proteins. The phylogenetic tree is calculated based on the JmjC domains of the proteins using the Neighbour Joining (NJ) method. The sequences used for this calculation are provided in Supplementary Figure S2.

Among the proteins identified was the Jumonji protein GASC1 (FIG. 1a). Due to the presence of a Jumonji domain JmjN and a related JmjC domain the protein is also denoted JMJD2c[8, 9] (FIG. 1a). The Jumonji protein family comprises a diverse group of proteins that belong to the α-ketoglutarate-dependent oxygenase superfamily. These proteins regulate various cellular processes, comprising cell-cycle progression and transcriptional regulation[5, 10-14]. A widespread feature of this protein group is the ability to bind Fe(II) ions. In addition, many of these proteins have the capability to hydroxylate protein substrates using α-ketoglutarate as a co-factor[15]. Of special interest, JmjC domain proteins have recently been identified as possible candidates for histone demethylases[16].

Figure 3:
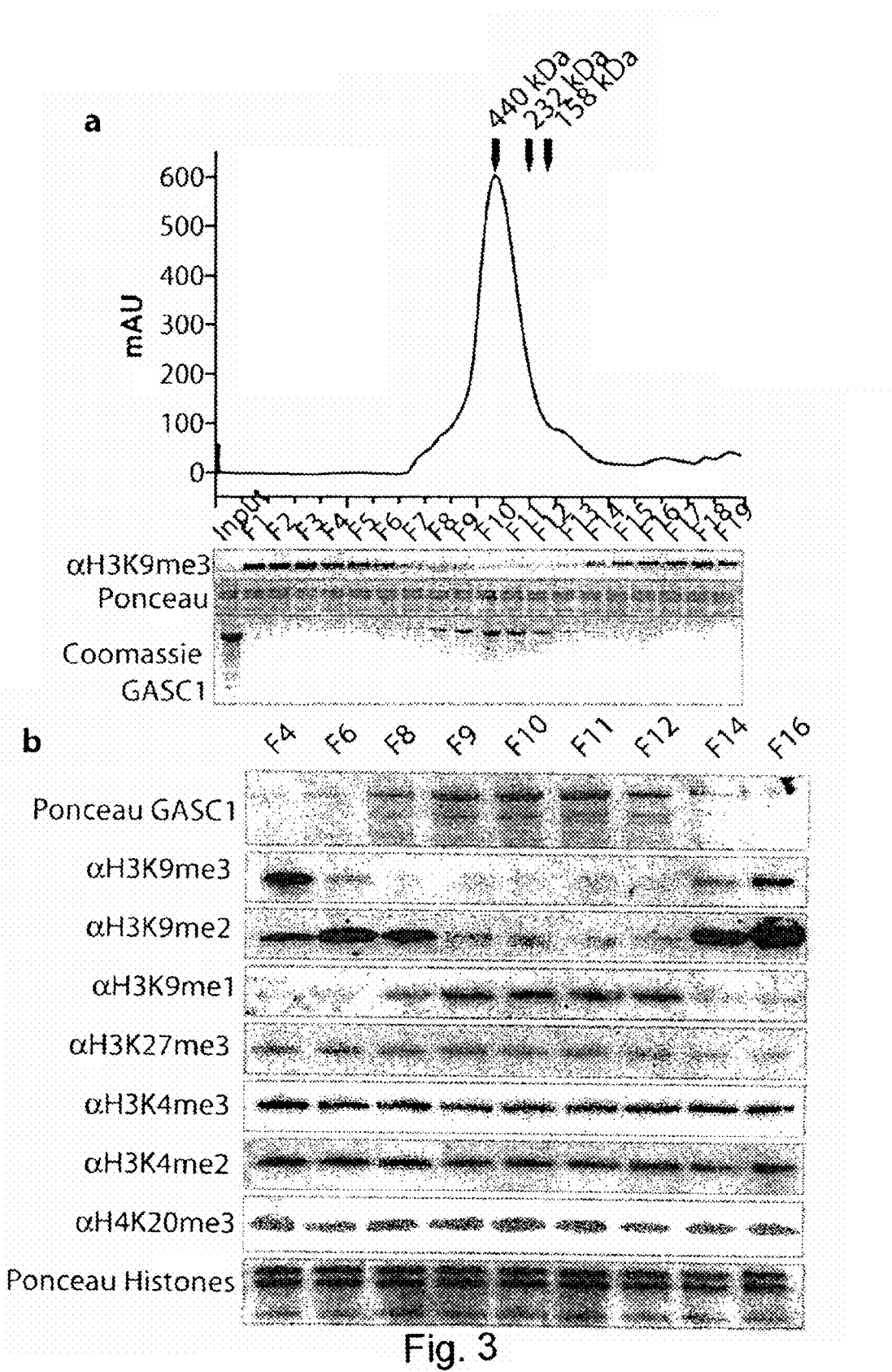
Figure 4:
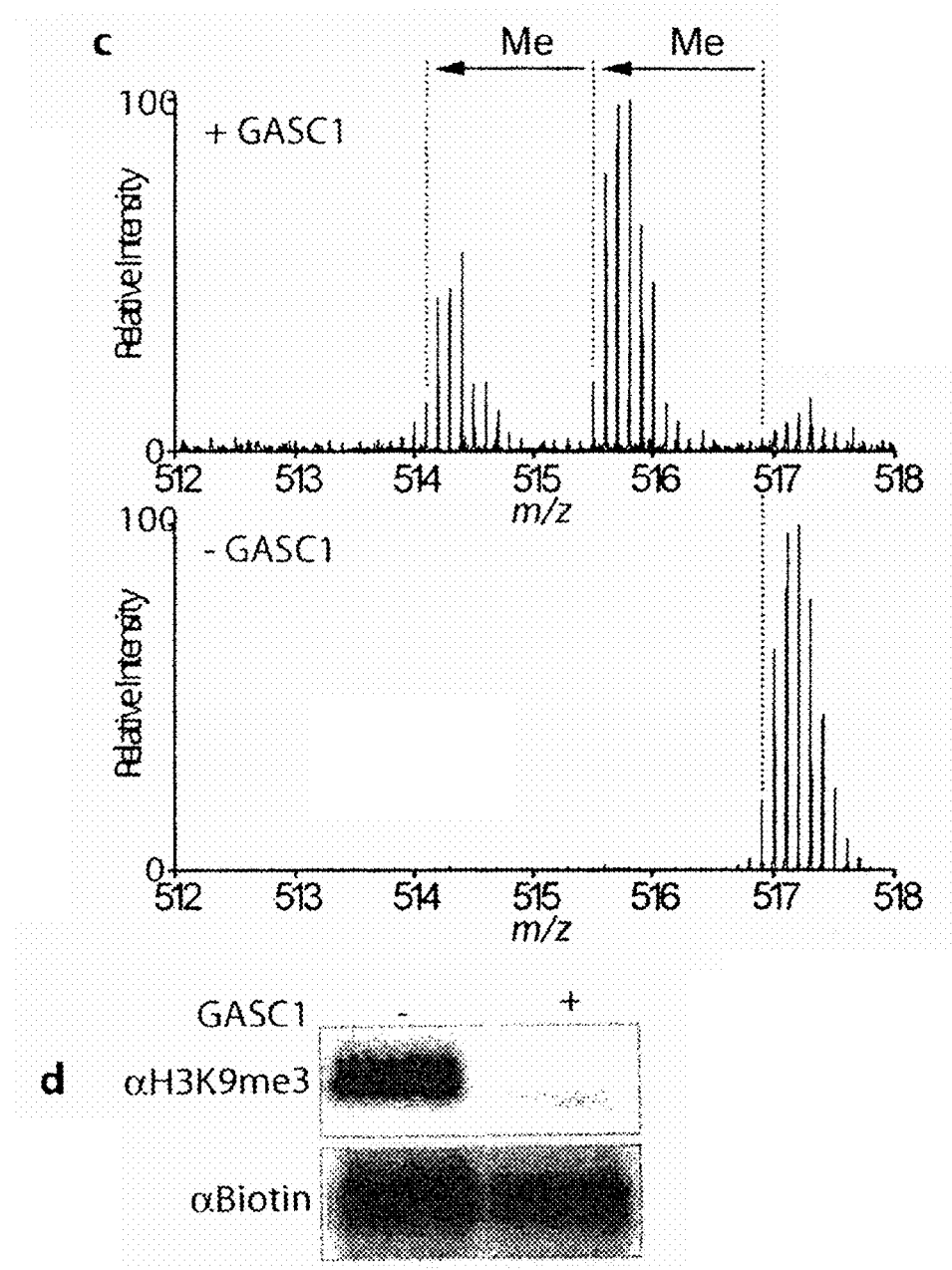

Since GASC1 was found to be associated with tri-methylated (me3) H3K9, the idea that GASC1 might be involved in demethylating this epigenetic mark was intriguing. To test this possibility, recombinant full-length His-tagged human GASC1 was generated ad purified from bacculovirus-infected insect cells (Supplementary Fig. S3). The affinity purified GASC1 was further purified by size exclusion chromatography, and the eluted highly pure GASC1 was tested for demethylation activity, by incubation with bulk histones. As shown in FIG. 3a, GASC1 very efficiently reduced tri-methylation at H3K9 as evaluated by immuno-blotting. It was also found that GASC1 could demethylate oligonucleosomes, the relevant physiological template (supplementary figure S4a).

To further analyse the specificity of the demethylating activity of GASC1, various fraction from the size-exclusion chromatography of GASC1 representing high to low amounts of GASC1 were incubated with bulk histones and synthetic H3-peptides methylated at lysine K9 or K27, and the methylation status of various epigenetic marks was evaluated by immunoblotting (FIGS. 3b and S4b). Here di- and tri-methylated H3K9 from histones was completely removed in the fractions with the highest concentrations of GASC1 (F9-12). A concomitant increase in mono-methylated (me1) H3K9 was also noted, consistent with GASC1 converting tri-methyl H3K9 to di-methyl (me2) and further to mono-methyl H3K9 (me1).

In contrast, the levels of other tested epigenetic marks including di-methylated H3K4, tri-methylated H3K4, tri-methylated H3K27 and tri-methylated H4K20 appeared to be unaffected by GASC1 treatment (FIGS. 3b and S4b).

Interestingly, di-methylated H3K9 appeared to be increased when histones were reacted with low to moderate amounts of GASC1 (F6, F8, F14 and F16). This indicates that the reason for the apparent increase in the di-methylated H3K9 mark could be due to a steady state level of this mark being reached in the initial phase of the demethylation reaction. Thus, it can be envisioned that although some di-methyl H3K9 is lost through GASC1 demethylation, additional di-methyl H3K9 will be added to the global pool by GASC1 demethylation of tri-methyl lysine, at least as long as significant levels of tri-methyl H3K9 are present.

Consistent with the results in FIGS. 3a and b, the demethylation activity of GASC1 vary in a concentration dependent manner and can be abolished by heat-denaturation of GASC1, Fig. S4 b,c, suggesting that the reaction is an enzyme-reaction. An additional in vitro demethylation study was performed, where pure synthetic tri-methylated H3K9 peptide was incubated with GASC1 Following 30 minutes incubation of pure tri-methylated H3K9 with GASC1 almost all tri-methyl H3K9 was converted to di- and mono-methyl H3K9 (Fig. S4 c,d).

To formally show that GASC1 does indeed demethylate tri- and di-methylated H3-K9, mass spectrometry was performed on synthetic peptides that had been incubated alone or in the presence of GASC1. This analysis showed that the majority of H3K9me3 peptide (approximately 80%) was converted to di- and mono-methylated H3-K9 after incubation of with GASC1 (FIG. 4c-6f).

Figure 2:
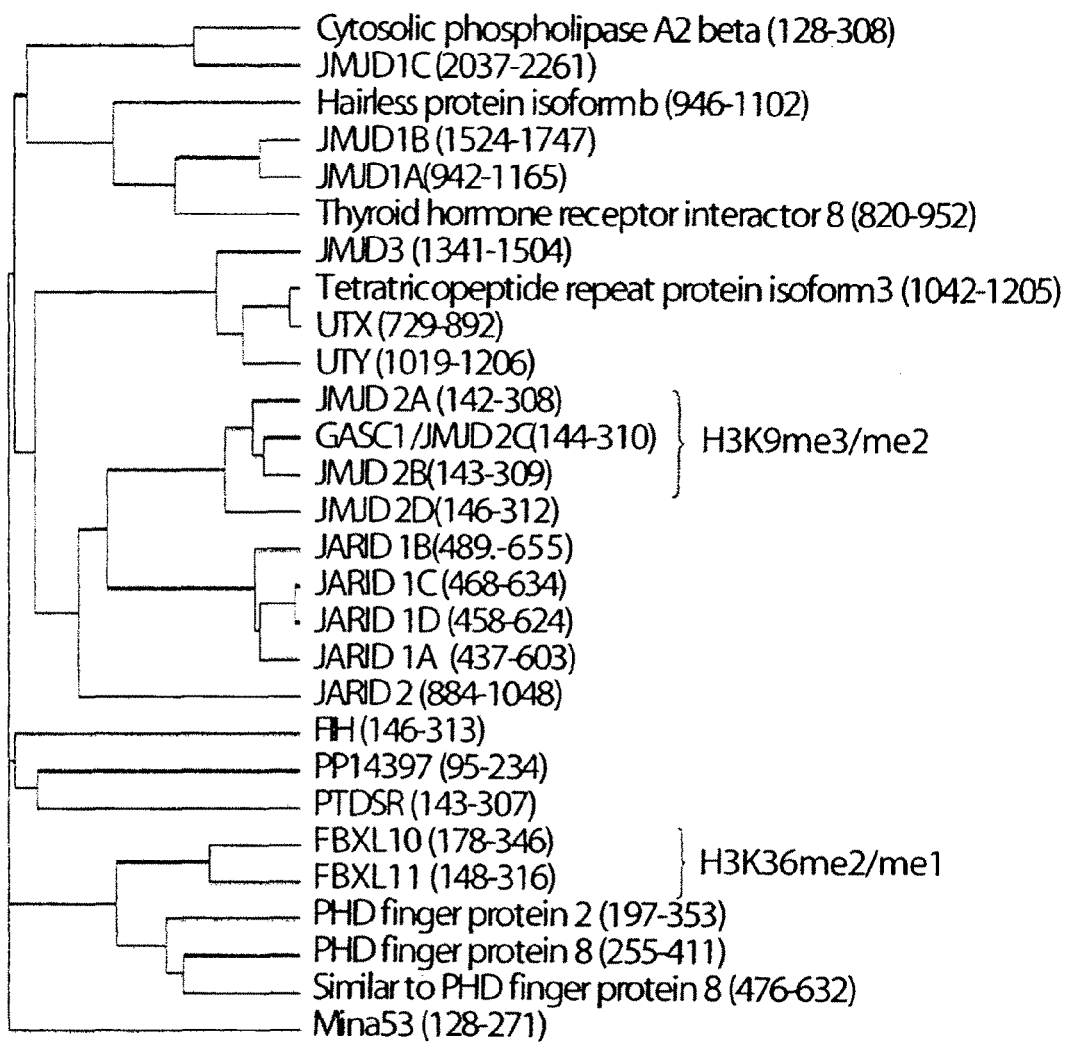

Next it was considered whether the close GASC1-homologues JMJD2a and JMJD2b (FIG. 1 a, FIG. 2 b) could also demethylate H3K9 in vivo. To investigate this full-length human JMJD2a, JMJD2b were cloned and recombinant proteins were produced from bacculovirus infected cells. Both homologues could demethylate H3K9me3 and H3K9me2 from bulk histones (supplementary figure S5). Likewise, GASC1 and its homolog JMJD2A appeared to have a comparable ability to demethylate synthetic H3K9 substrates (supplementary figure S4 d,e). Together, these results strongly suggest that both tri- and di-methylated H3K9 are substrates of GASC1 and its homologues in vitro.

To obtain insights into the specificity of the demethylation reaction in vivo, irst human GASC1 was modelled onto the structure of FIH, the only Jumonji protein for which the three-dimensional structure has been resolved[11, 15, 17-19]. In agreement with the alignment (FIG. 5 and supplementary Fig. S2), the modelling indicated that residues histidine H190, glutamic acid E192, and histidine H288 form an essential part of the iron-binding groove of GASC1 (FIG. 6h, i). Further, the in silico model also predicted that residues T187 and R208 are involved in binding of a-ketoglutarate and critical for the demethylation function of GASC1. Next, the tri-methylated H3 histone tail was modelled onto the predicted GASC1 structure. The H3 histone tail tri-methylated at K9 fitted well into the iron-binding groove of GASC1 and the K9 methyl groups could be placed in close vicinity to the reactive iron without causing any steric clashes between the methylated histone tail and the GASC1 structure (FIG. 6h). On the basis of this in silico model it was predicted that mutating H190 and E192 would be sufficient to abrogate the iron-binding ability of GASC1 and thus also to inhibit its demethylation activity.

To test this hypothesis, performed demethylation assays were performed by incubating bulk histones with wild-type and mutant GASC1 (H190G/E192A) in which histidine H190 and glutamic acid E192 had been replaced with glycine and alanine, respectively. While wild-type GASC1 had a robust demethylating activity, mutant GASC1 had no detectable demethylation activity, indicating that the putative iron-binding residues are crucial to the demethylating activity of GASC1. Size-exclusion chromatography profiles of wild-type and mutant GASC1 were almost identical indicating that the mutations did not compromise the overall structure of the protein (supplementary figure S6).

Figure 7:
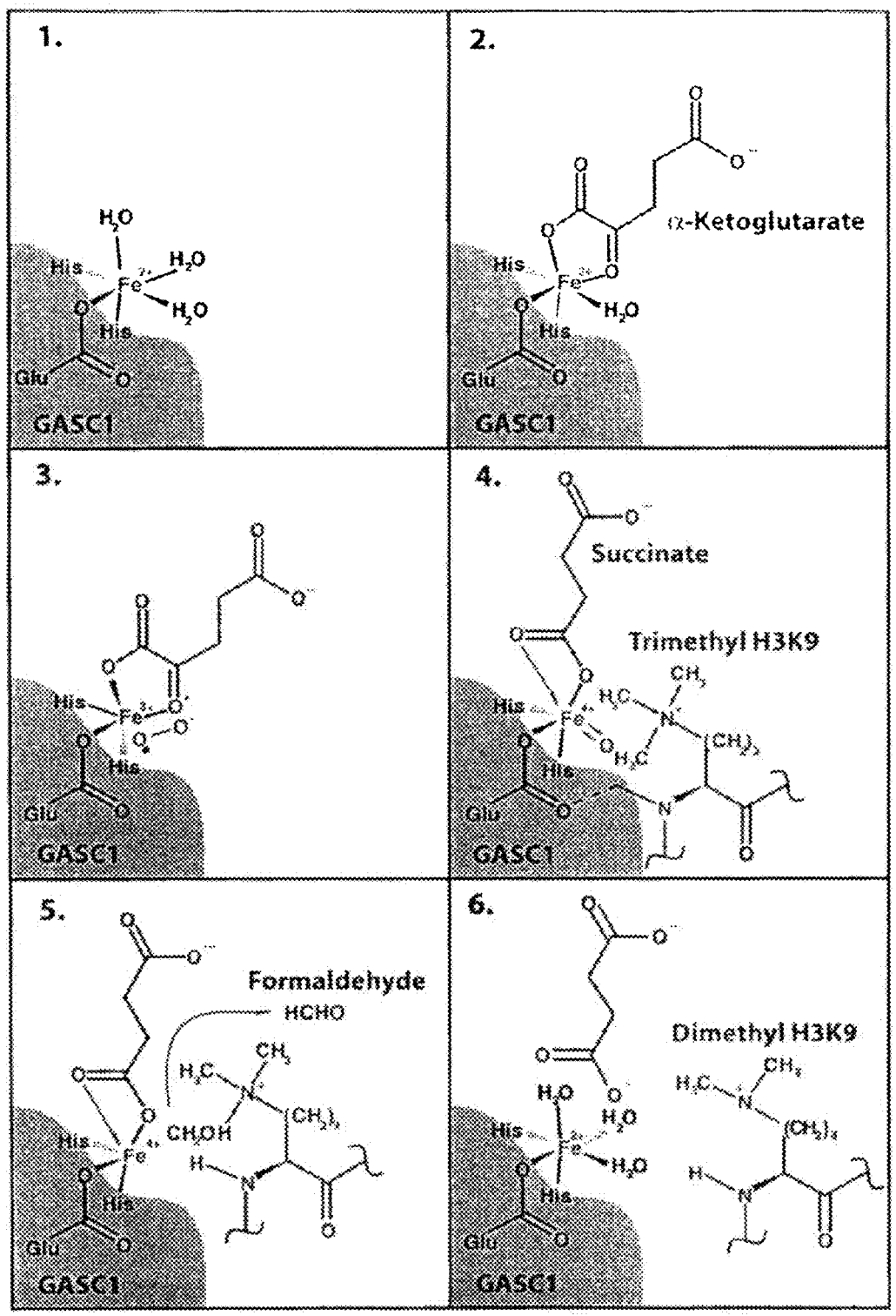
FIG. 7-8: GASC1 demethylation occurs through a hydroxylation reaction dependent on iron and α-ketoglutarate. a, Proposed reaction scheme for GASC1-mediated demethylation of tri- and di-methylated H3K9. 1. Fe(II) (magenta) is bound to GASC1 by the facial triad of metal binding residues His190, Glu192 and His288 (blue text). 2. α-ketoglutarate (red) is bound, probably through residues Thr186 and Lys208 3. Iron (magenta) subsequently binds molecular oxygen 4. Next oxidative decarboxylation of α-ketoglutarate (red) produces carbon dioxide, succinate (red) and ferryl (FeIV=O, magenta). 5. Ferryl (magenta) subsequently hydroxylates a methyl group of lysine H3K9 (green), releasing formaldehyde. 6. Finally the hydroxylated histone tail (green) and succinate (red) can leave the GASC1 molecule leading it vacant for new demethylation cycle. b, Demethylation assay using synthetic H3K9me3 peptide as substrates. Peptides were incubated with 20 μg His-GASC1 in the presence of, or absence of its co-factors ascorbic acid, α-ketoglutarate and Fe2SO4, and EDTA, for 30 min. at 37° C., and analyzed by western blotting. The relative demethylation activity of GASC1 was quantified using a Fujifilm darkbox LAS 3000 reader and normalized to the loading control (α-biotin). H3K9me3 peptide (lane1) was set to 100%. Lane 2-7; H3K9me3 peptide incubated in demethylation buffer in the presence or absence of EDTA or co-factors as indicated. c, Demethylation assay using recombinant GASC1 and bulk histones as substrates. Histones were incubated with His-GASC1 in the presence of co-factors ($FeSO_4$ and α-ketoglutarate) for 30 min. at 37° C., in the presence or absence of varying amounts of the α-ketoglutarate analog N-oxalylglycine. The methylation status was evaluated by western blotting. d, Binding mode of 2-ketoglutarate and N-oxalylglycine at the Fe(II) active site. e, Formaldehyde release by GASC1 mediated H3K9$_{me3}$ demethylation. Formaldehyde release was measured using a demethylation-FDH-coupled assay[4]. The demethylation-FDH-coupled assays were carried out using fixed amount of the enzyme GASC1 (40 μg) but varying amounts of the substrate H3K9$_{me3}$ peptide. Formaldehyde production was monitored by measuring NADH production at OD 340 nm. 50 μg H3K9 peptide (unmethylated) as substrate was used as negative controls.

Next, several experiments were performed to address the reaction mechanism for GASC1-mediated demethylation of the H3K9 tri and di-methyl marks. Various studies[11, 17-24] of α-ketoglutarate-dependent oxygenases including the Factor Inhibiting HIF1 (FIH) suggest the following reaction mechanism: first the enzyme binds iron through its metal-binding motif HXD/EX$_n$H the so-called facial triad[20] (HXEX$_n$H in GASC1). Then, the Fe(II)-enzyme complex binds the cofactor α-ketoglutarate (αKG), and subsequently the substrate and oxygen. The binding of oxygen is followed by the oxidative decarboxylation of αKG to produce succinate, carbon dioxide and ferryl. The latter, is a highly reactive group and can potentially oxidise a C—H bond in a lysine methyl-group, forming an unstable carbinolamine that rapidly would break down leading to the release of formaldehyde and loss of a methyl group from lysine (FIG. 7a).

Dioxygenases belonging to the cupin superfamily are dependent upon Fe(II) and α-ketoglutarate. In addition, some cupin dioxygenases, including FBXL11 have the additional requirement of ascorbate for full catalytic activity[5, 21, 23]. The mode of action of ascorbate is presently unclear but has been suggested to reduce Fe(III) to its active state Fe(II) or to function as a "surrogate reducing substrate" to 'rescue' the dioxygenase enzyme in the event of the uncoupled production of a ferryl (FeIV═O) intermediate[17, 22].

To test whether GASC-1 mediated demethylation would fit the reaction-mechanism described above and depicted on FIG. 7a, the importance of the putative co-factors for the demethylation reaction was tested.

Figure 8:
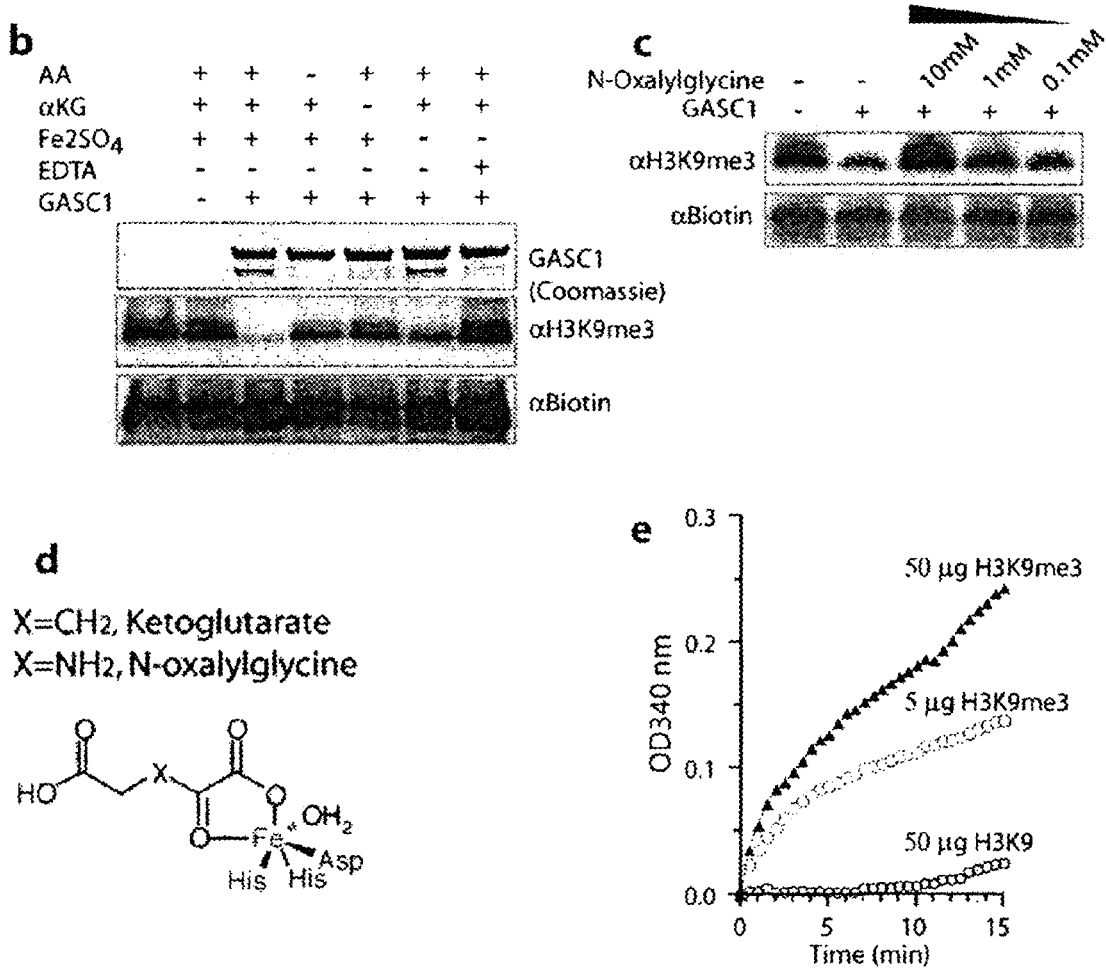

Purified His-tagged GASC1 was incubated with bulk histones as substrate in the presence or absence of its co-factors (FIG. 3b). In the presence of all its co-factors GASC1 demethylates H3K9me3 in vitro, whereas GASC1-incubations in the presence of EDTA (chelating iron) or GASC1 incubations in the absence of its co-factors was significantly reduced (FIG. 8b). The ability of the demethylation reaction to occur in spite of no addition of co-factors, is probably due to co-factors (iron and αKG) co-purifying with the recombinant GASC1. For this reason we further sought to confirm the importance of these co-factors by testing the ability of N-oxalylglycine, quercetine, $CoCl_2$ and $NiSO_4$ to inhibit GASC1-mediated demethylation of H3K9me3. All these compounds were all able to inhibit the demethylation reaction effectively (FIG. 8c and data not shown). N-oxalylglycine (FIG. 8d) and quercetine are αKG-analogues and presumably inhibit the activity of GASC1 by displacing αKG from the iron-binding residues of GASC1. Analogously the inhibition of GASC1 by $CoCl_2$ and $NiSO_4$ probably involves dislocation of Fe(II) from the iron-binding site of GASC1 by competing cobalt(II) or nickel(II) ions. The requirement of ascorbic acid, αKG and iron in the demethylation reaction and the inhibition of the reaction by nickel and cobalt salts and αKG analogues strongly suggest that GASC1 is indeed a dioxygenase.

Moreover, in the presence of its cofactors Fe(II) and αKG, recombinant His-tagged GASC1 released formaldehyde (FIG. 8e) consistent with the proposed reaction scheme on FIG. 3a. Taken together, these results demonstrate that GASC1 directly demethylates tri- and di-methylated lysine K9 on histone H3 in vitro through a hydroxylation reaction requiring iron and αKG and producing formaldehyde and mono-methylated H3K9.

Figure 9:
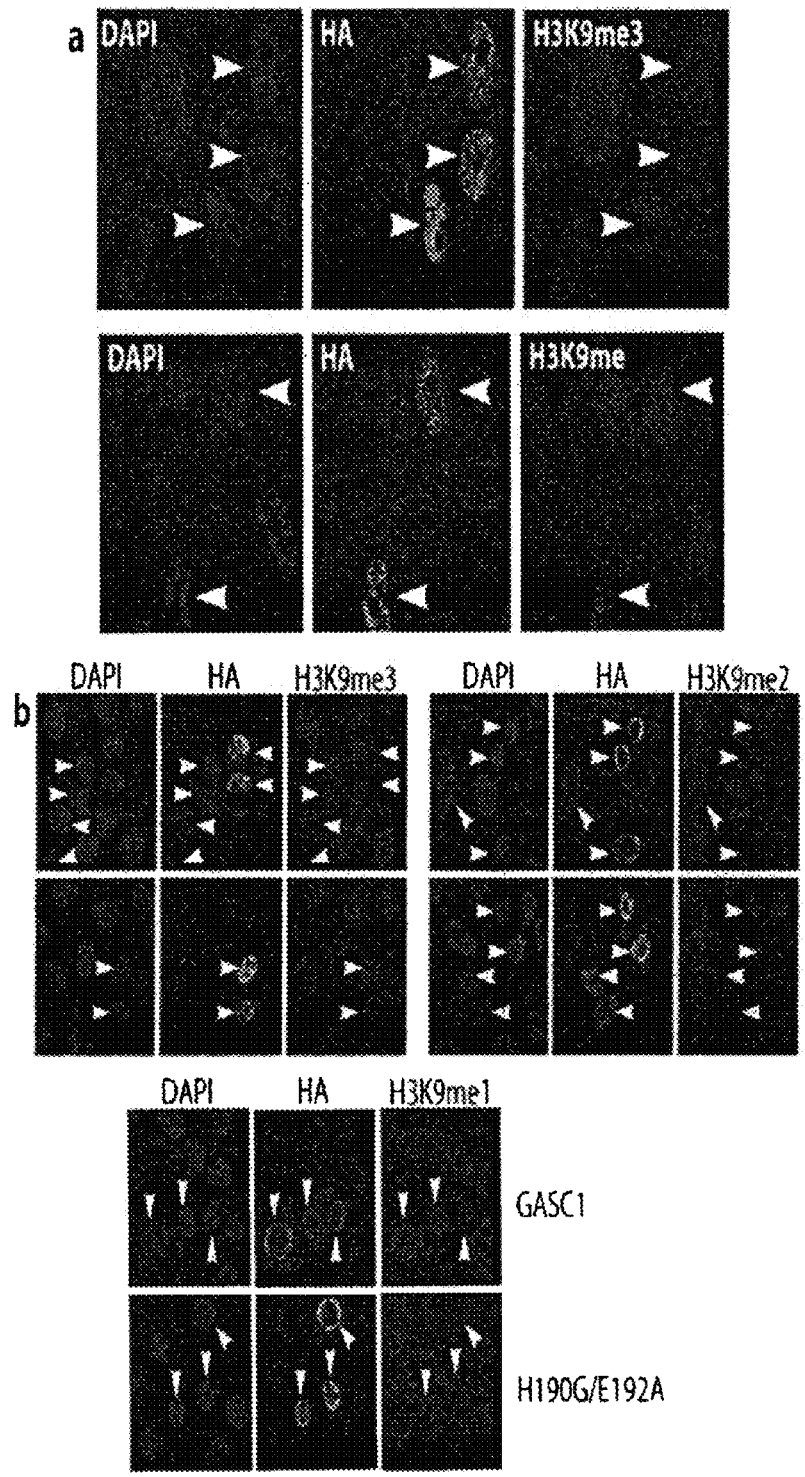

Having established that GASC1 can demethylate di- and tri-methylated H3K9 in vitro, it was considered whether GASC1 could modulate heterochromatin formation/maintenance in vivo. To address this question it was first investigated whether enforced expression of GASC1 could modulate H3K9 methylation in vivo. Human diploid fibroblasts were infected with a retrovirus expressing wild-type human GASC1 and the methylation status at H3K9 was tested using confocal microscopy. GASC1 localized to the nucleus, consistent with the presence of a putative nuclear localization signal in the protein. Infection with pBabe-HA-GASC1 caused an efficient decrease of H3K9 tri-methyl and an increase of mono-methylated H3K9 (FIG. 9a). In contrast, tri-methylated H3K4 and tri-methylated H3K27 were unaffected by GASC1 over-expression, (supplementary figure S7).

Next, the human osteosarcoma cell line U2OS was transfected with plasmids expressing wild-type and mutant GASC1 (H190G/E192A) in which histidine H190 and glutamic acid E192 had been replaced with glycine and alanine, respectively. While ectopic expression of wild type GASC1 efficiently abrogated the tri- and di-methylation of K9 on histone H3 in vivo, mutant GASC1 was unable to do so (FIG. 9b).

Interestingly, ectopic expression of GASC1 led to a significant increase in mono-methylated H3K9, suggesting that GASC1 demethylates both tri- and di-methylated H3K9 in vivo. The decrease in tri-methylated H3K9 was also apparent in GASC1 transfected U2OS cells, when evaluating the global levels of this mark by western blotting (FIG. 10c), further confirming the crucial importance of these predicted Fe(II)-coordinating residues.

Figure 10:
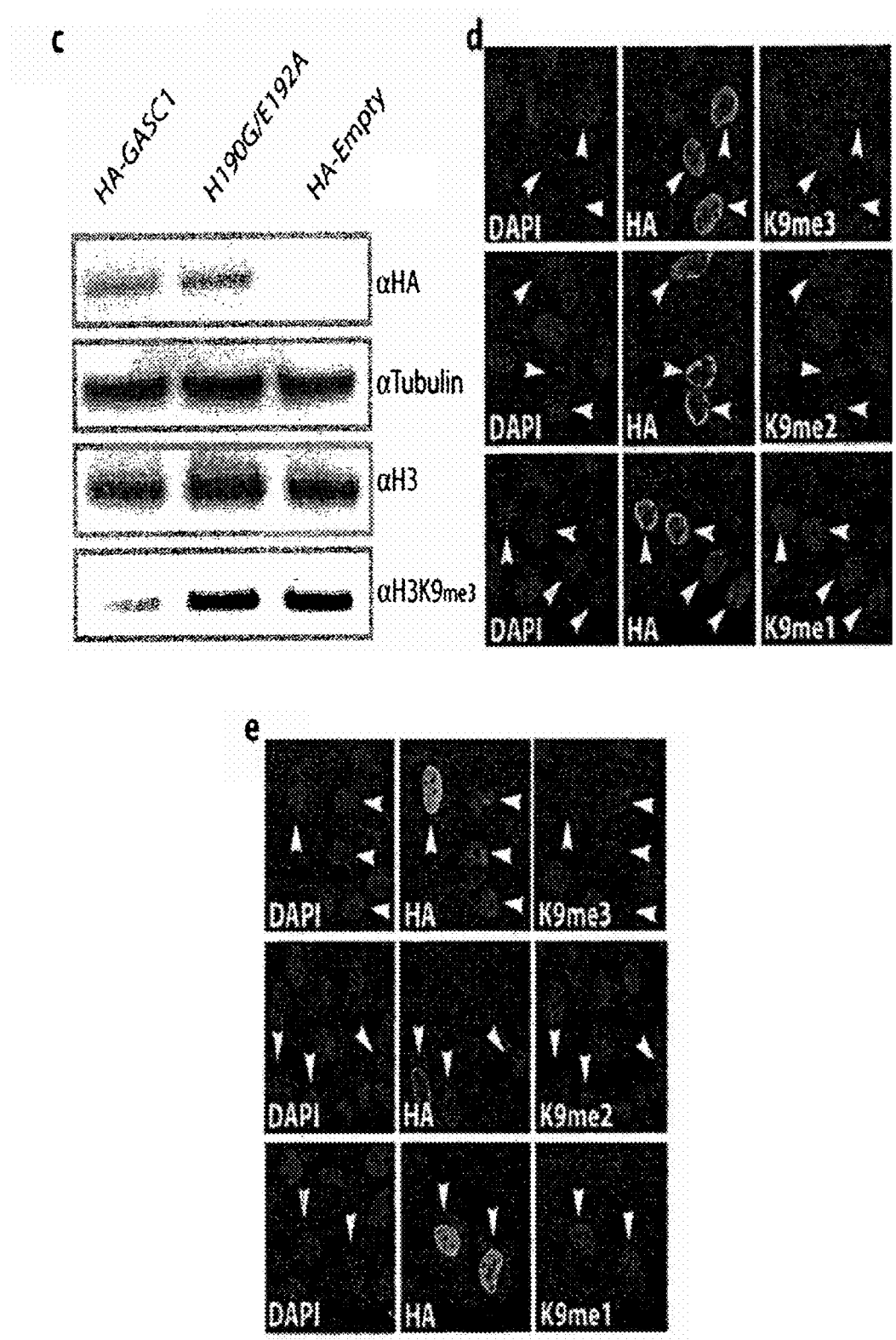

Next, it was tested whether the close GASC1-homologues JMJD2a and JMJD2b (FIG. 1a, FIG. 2b) also could demethylate H3K9 in vivo, by over-expressing the proteins in U2OS cells. As for GASC1, ectopic expression of JMJD2a and JMJD2b led to a significant reduction of tri- and di-methylated H3K9, with a concomitant increase in mono-methylated H3K9 (FIG. 10 d, e). These results suggest that GASC1 belongs to a family of histone H3K9 demethylases.

Heterochromatin formation and maintenance requires the presence of tri- and di-methylated H3K9 and HP1-binding[25-27]. Since the ectopic expression of GASC1 leads to a global reduction of H3K9 di- and tri-methylation, it was tested whether HP1-binding and localization was affected by increased levels of GASC1. NIH 3T3 cells were transfected with a plasmid expressing HA-tagged GASC1, and determined the endogenous HP1 distribution in pre-extracted cells by confocal microscopy. As anticipated, HP1p was delocalized in cells over-expressing GASC1, whereas no delocalization occurred when the H190G/E192A mutant was transfected (FIG. 11f). Likewise ectopic expression of the GASC1 homologues JMJD2a and JMJD2b led to de-localization of HP1 (supplementary figure S8). These results were further validated by demonstrating decreased levels of HP1α and HP1γ associated with chromatin in GASC1 over-expressing cells (FIG. 11g). For this purpose, HEK293 cells with tetracycline-regulated expression of Myc-tagged GASC1 were generated. Selected cells were incubated in the presence or absence of tetracycline overnight and as shown in FIG. 11g, the amount of chromatin-bound HP1α and HP1γ was reduced in GASC1 over-expressing cells. Taken together these results suggest that GASC1 could play a physiological important role in controlling heterochromatin formation and maintenance.

Until recently, tri-methylated lysine has been considered as an irreversible covalent histone modification[28] and the present report is the first to identify a histone tri-methyl demethylase. Our results show that GASC1 specifically demethylates methylated H3K9, but in contrast to LSD1 and FBXL11 that are specific for mono- or di-methylated substrates[4, 5], GASC1 has the ability to remove both the di- and tri-methyl species of H3K9 in vitro and in vivo.

GASC1 contains several domains, which potentially could serve to confer the protein with its exquisite specificity towards tri- and di-methylated H3K9 (FIG. 1a). In addition to a Jumonji C (JmjC) and Jumonji N domain (JmjN), the protein features two plant homeodomains (PHD) as well as a tandem Tudor domain (Tdr). The function of these domains is presently unclear but they have all been implicated in chromatin modulation[8, 10, 12, 29, 30]. For example, the Tudor domain of 53BP1 has been reported to bind to the tri-methylated form of lysine 79 on histone H3[31] and the PHD domain has been shown to collaborate with Bromo domains in binding to nucleosomes[30]. In order to gain insights into which domains are required for the demethylation function of GASC1 and to resolve which domains determine its substrate specificity, mutational studies of the GASC1 protein were performed. This was done by generating a series of GASC1 expression constructs carrying deletions of the JmJC, JmjN and PHD domains. These results showed that the JmjC and JmjN domains are indispensable for the demethylating activity of GASC1 (supplementary figure S9). In contrast the deletion of the PHD domains did not appear to affect the ability of GASC1 to demethylate H3K9me3 in vivo (Fig. S9).

In light of the similar reaction mechanism of GASC1 and FBXL11, it is pertinent to ask why GASC1 has the ability to demethylate the tri-methylated histone lysine substrate, whereas FBXL11 has not. A potential explanation could be that the iron/substrate-binding groove is smaller in FBXL11 than in GASC1. Although this explanation would require experimental testing, it is supported by in silico modelling. When comparing models of the two Jumonji proteins modelled with FIH as template, it was found that they both feature a loop region located at the edge of the iron-binding groove of the models. This loop region is significantly longer in the FBXL11 model opening the possibility that it could flip, making the iron/substrate binding groove of this protein smaller and consequently inhibiting the accommodation of a tri-methyl lysine substrate.

It is predicted that the demethylation pathway described in the present report and summarized on supplementary figure S8b is evolutionarily conserved. Of note in this context, the *Schizosaccharomyces pombe* Jumonji protein, Epe1 has been reported to antagonize heterochromatization[10]. Thus a recent report[10] has demonstrated that enforced expression of Epe1 causes a decrease in di-methylated H3K9 and antagonizes hetero-chromatin with a concomitant destabilization of centromers and mating type loci[10]. This Epe1-mediated phenotype was dependent of an intact JmjC domain and although it has not been shown that the capacity of Epe1 to antagonize heterochromatization is due to a demethylation activity, it is appealing to assume such a role in light of our present data.

The existence of several closely related human homologues (JMJD2a and JMJD2b, FIG. 2b), with similar enzymatic activity, as GASC1 is indicative of functional redundancy and the necessity for a tight control of H3K9 tri-methyl demethylase activity. This is to be expected as the strict control of heterochromatin formation and maintenance is critical for both proper biological function and genomic integrity. For instance centromeric heterochromatin formation is essential for the correct segregation of chromosomes during mitosis[32]. Similarly it has been demonstrated that the deletion of Suv39H1 and Suv39H2 genes in mice, whose products are responsible for di- and tri-methylation of H3K9 in heterochromatin, leads to chromosomal instability and collaborates with oncogenes in inducing mouse lymphomas[6]. Therefore aberrant activity of GASC1 or its homologues, could potentially lead to genomic instability and consequently cancer. Indeed, GASC1 was originally identified as a gene frequently amplified in oesophageal squamous cell (ESC) carcinoma[22] and GASC1 is over-expressed in various cancer types containing chromosomal abberations[33, 34].

To obtain further support for the involvement of GASC1 in cancer, the Oncomine database was searched for differential GASC1 expression in normal versus tumor tissue. The expression of GASC1 and its homologues JMJD2a and JMJD2b were found to be significantly increased in prostate cancers relative to normal tissue (supplementary figure S11). Previously GASC1 has been shown to be amplified in several cell lines derived from ESC carcinomas[33]. The methylation status of the H3K9 epigenetic mark was tested in an ESC cell line with GASC1 gene amplification (KYSE-150) as well as in one cell line with more moderate expression (KYSE-450). The human osteosarcoma cell-line U2OS was included as controls. To test the importance of GASC1 amplification we tested the effect of GASC1 knockdown on the H3K9 methylation status in cells transfected with siRNA oligos to GASC1 and/or to its homologues. Cells were transfected with LMP-GASC1 followed by three days selection with puromycin. The efficiency of GASC1 knockdown was assessed by RT-QPCR (FIG. 5a). H3K9me3 was significantly increased in KYSE-150 cells in response to GASC1 knockdown as evidenced by western blotting (data not shown).

Di- and tri-methylated H3K9 is required for HP1-binding, essential for heterochromatin formation and associated with transcriptional repression. Moreover these epigenetic marks are increased on specific genes in senescence, a key mechanism guarding cells against cancer[36-39]. It can therefore be speculated that amplification of GASC1 may reduce the ability of cells to become senescent, or lead to de-repression of otherwise silenced oncogenes (FIG. 6d). Accordingly, inhibition of GASC1-demethylating activity could thus potentially constitute a new anti-neoplastic therapeutic modality.

Figure 12:
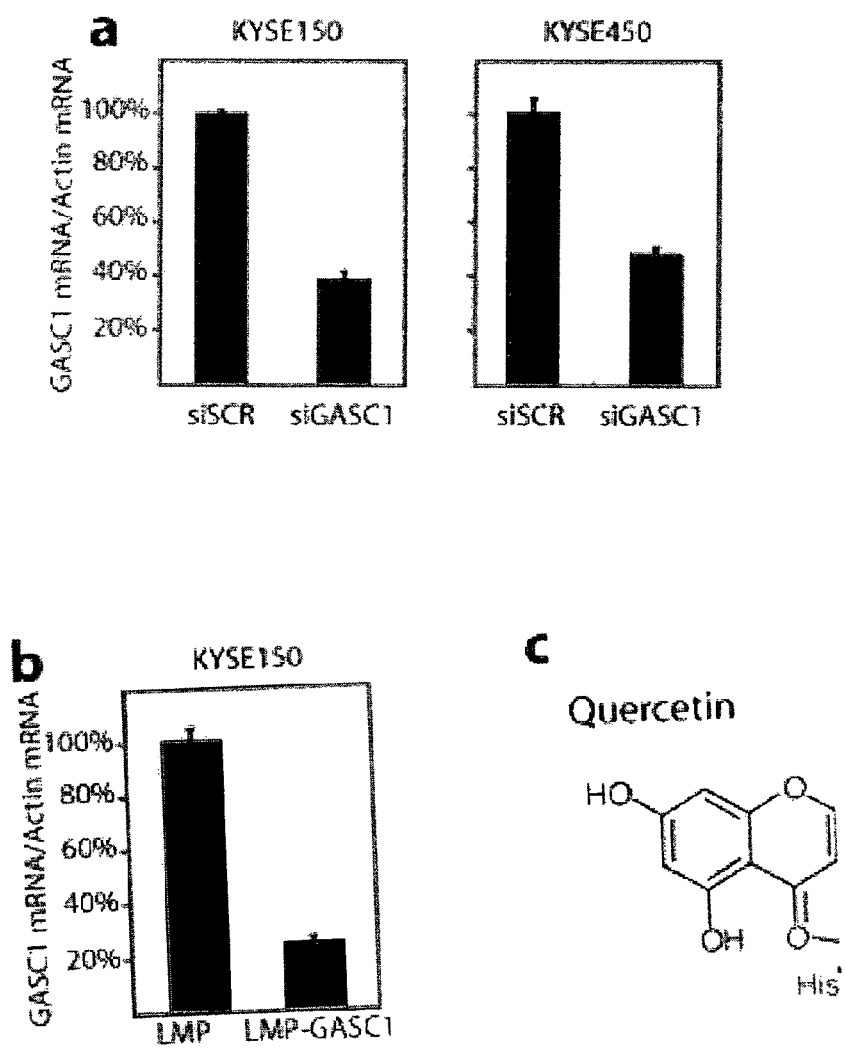
Figure 14:
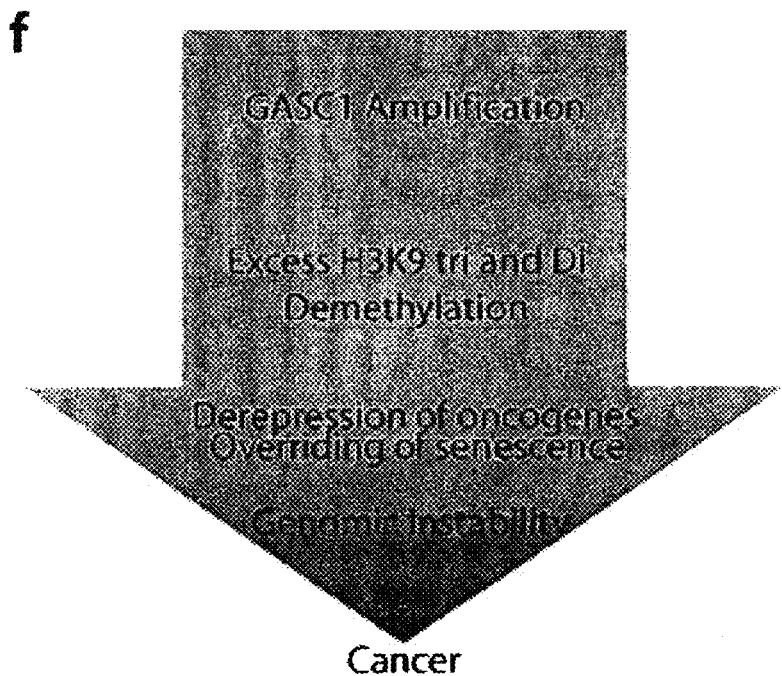
Figure 15:
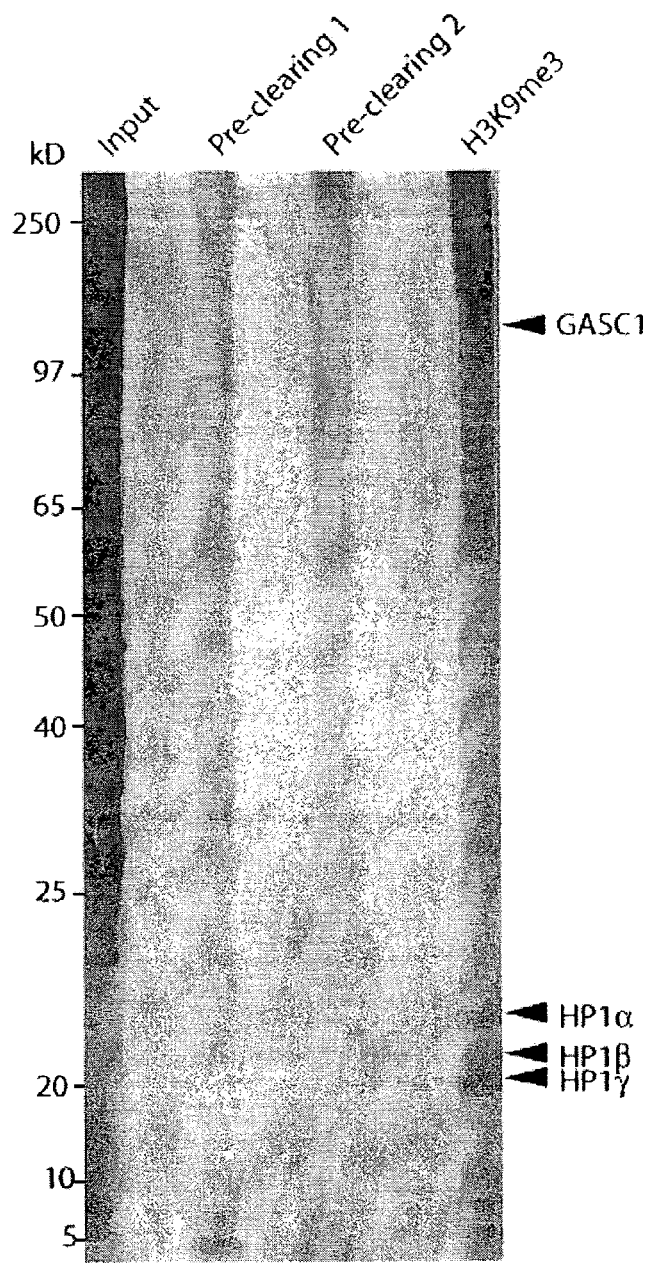
FIG. 15 (S1): Histone peptide pulldown of HeLa nuclear proteins Pull-down assays were performed using HeLa cell nuclear extracts and histone H3 peptide tri-methylated at lysine 9. The Hela nuclear extract was pre-cleared with uncoupled streptavidin beads (preclearing 1) and then with streptavidin beads coupled to unmodified H3 histone (preclearing 2). The pre-cleared lysate was then incubated with H3 histone peptide trimethylated at K9 (H3K9me3), pre-coupled to streptavidin beads. Beads were washed and bound proteins were subsequently eluted, resolved by SDS PAGE and visualized by silver staining. Protein bands enriched in the H3K9me3 pull-down were subse-quently identified by mass-spectrometry. One of the enriched bands was identified as the jumonji protein GASC1 (see arrow). The HP1 α-γ proteins also enriched in the pull-down are likewise indicated. Molecular weight markers are indicated on the left.
Figure 20:
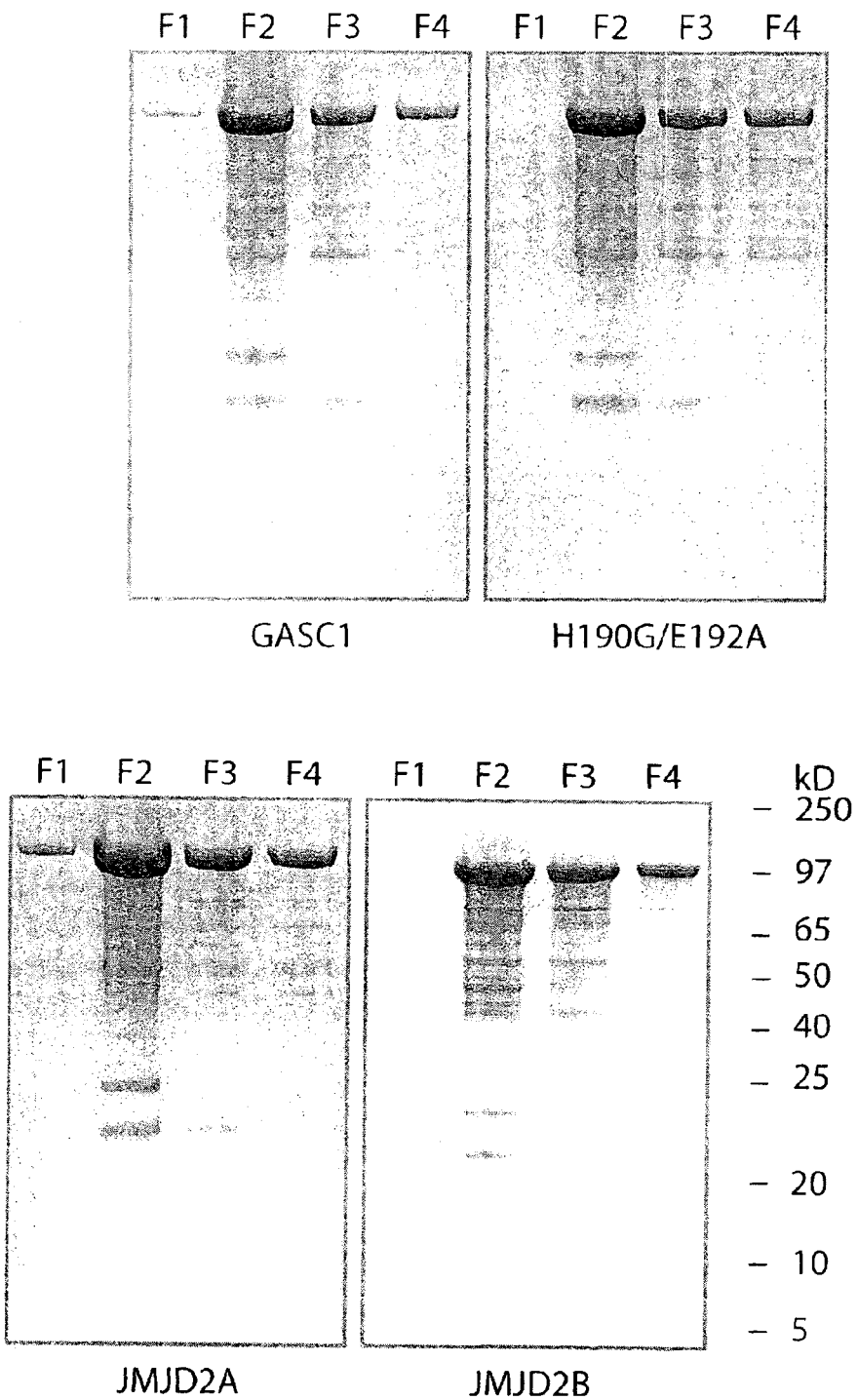
FIG. 20 (S3): Purification of His-tagged recombinant GASC1, GASC1 (H190G/E192A) mutant and JMJD2A and JMJD2b. Fractions 1-4 eluted from a cobalt-affinity column, were subjected to SDS-PAGE and Coomassie stained. Fractions F2 were further purified by size exclusion chromatography to obtain highly pure protein preparations.
Figure 21:
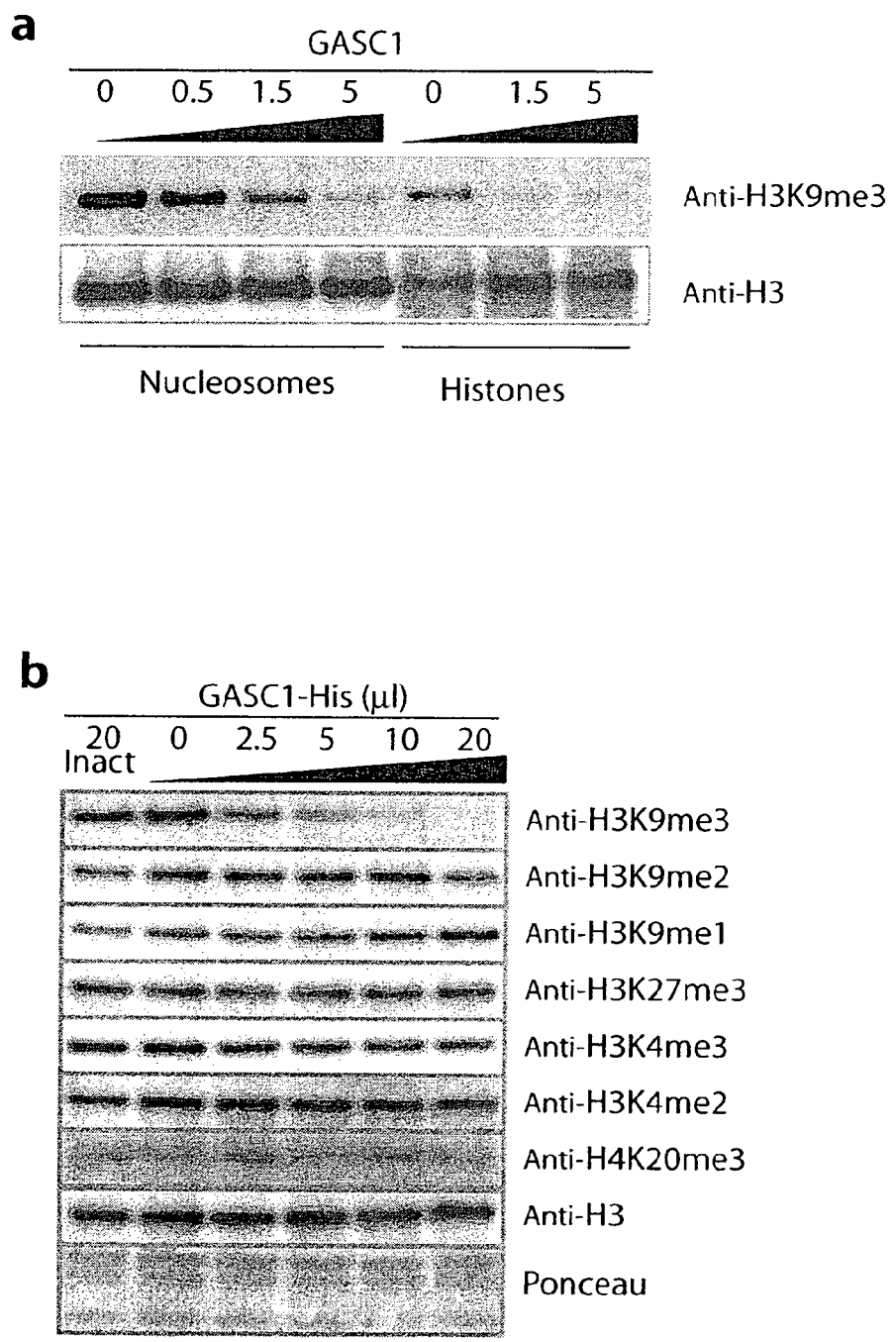
FIG. 21-23 (S4): GASC demethylates H3K9me3 and H3K9me2. a, Demethylation assay using varying amounts of recombinant GASC1 and oligonucleosomes or bulk histones as substrates. b, Demethylation assay using recombinant GASC1 and bulk histones as substrates. Histones were incubated with varying amounts of His-GASC1 as indicated, in the presence of its co-factors for 30 min. at 37° C., and analyzed by western blot analysis. Heat inactivation (inact.), for 5 min. at 60° C., abrogated the demethylating activity of GASC1. c, Demethylation assay using recombinant GASC1 and synthetic tri-methylated H3K9 peptides as substrates. Peptides are incubated with 10 μg His-GASC1 in the presence of co-factors for 30 min. at 37° C. d, Demethylation assay using recombinant GASC1 or JMJD2a and synthetic tri- di- and mono-methylated H3-K9 peptides as substrates. Peptides are incubated with 8 μg His-GASC1 or His-JMJD2a in the presence of co-factors for 30 min. at 37° C., and analyzed by western blot analysis.
Figure 22:
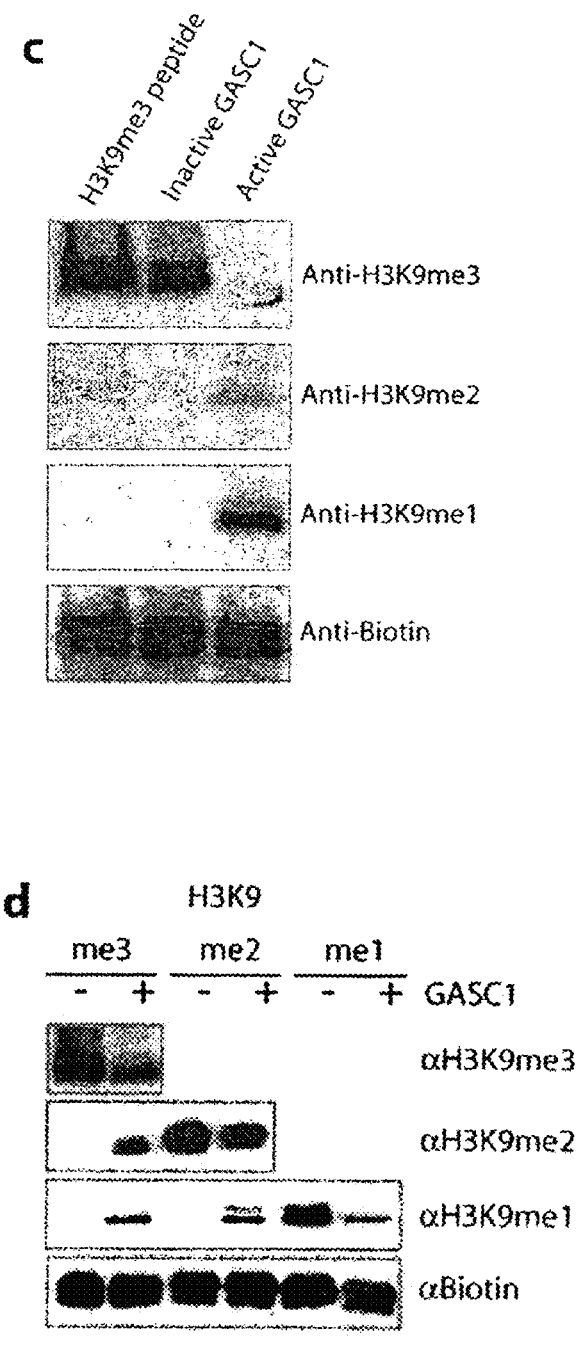
Figure 23:
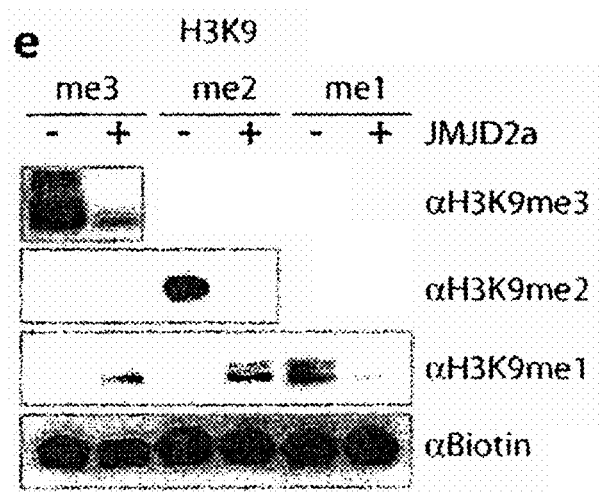
Figure 24:
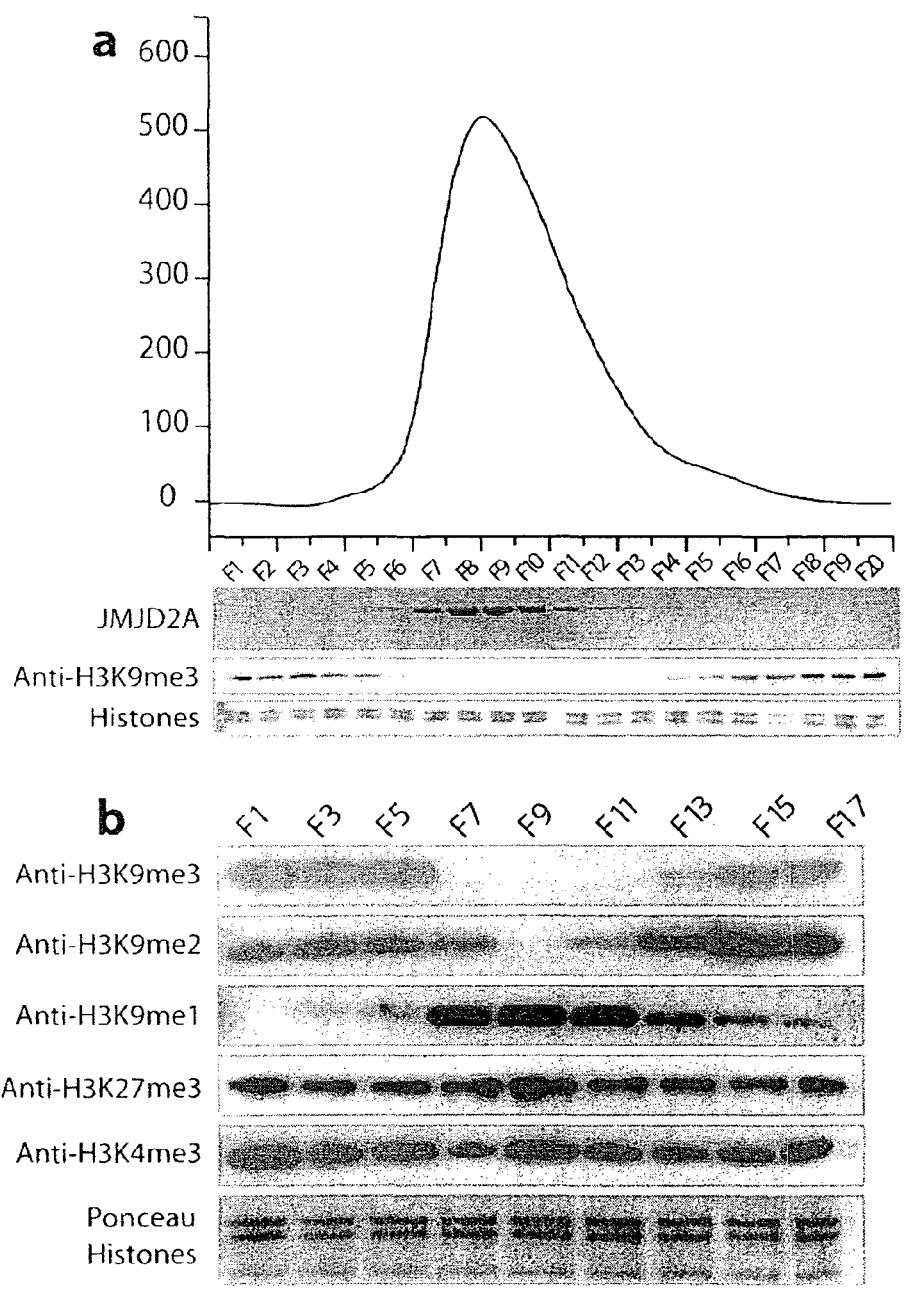
FIG. 24-25 (S5): JMJD2A and JMJD2B demethylate histones tri- and di- methylated at H3-K9. a, Purification of recombinant JMJD2A by size exclusion chromatography. One ml fractions were collected and 10 μl of the material was incubated with bulk histones for 30 min. at 37° C. Demethylation activity was assayed for by blotting for tri-methylated H3-K9. b, Demethylation assay using recombinant JMJD2A and bulk histones as substrates. Various fractions from size-exclusion chromatography (Fig. S5a) were analyzed by western blot analysis. c, Purification of recombinant JMJD2B by size exclusion chromato-graphy. One ml fractions were collected and 10 μl of the material was incubated with bulk histones for 30 min. at 37° C. Demethylation activity was assayed for by blotting for tri-methylated H3-K9.
Figure 25:
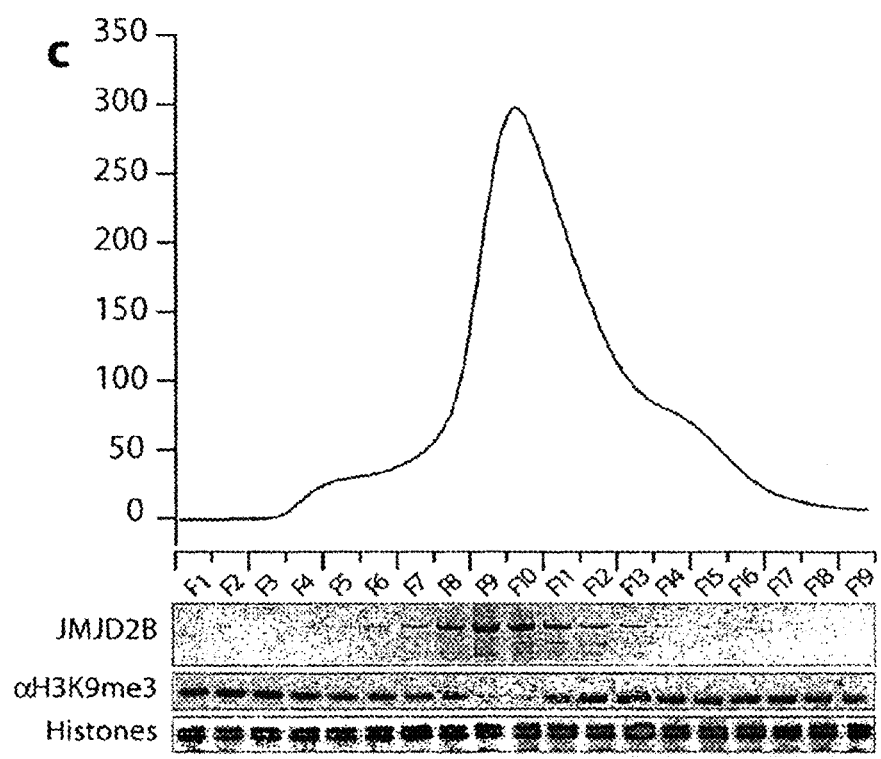
Figure 26:
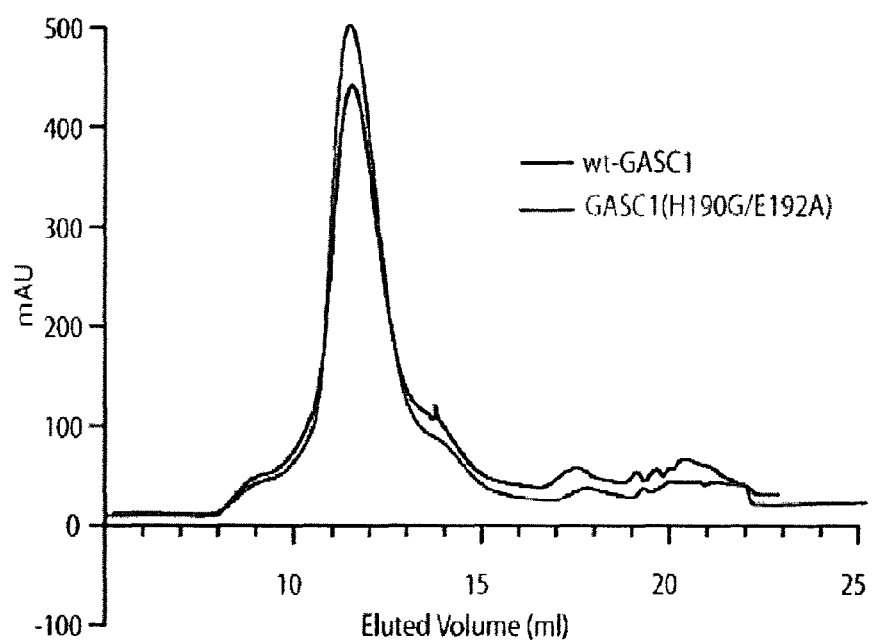
FIG. 26 (S6): Size exclusion chromatography of wild-type and H190G/E192A mutant GASC1.
Figure 27:
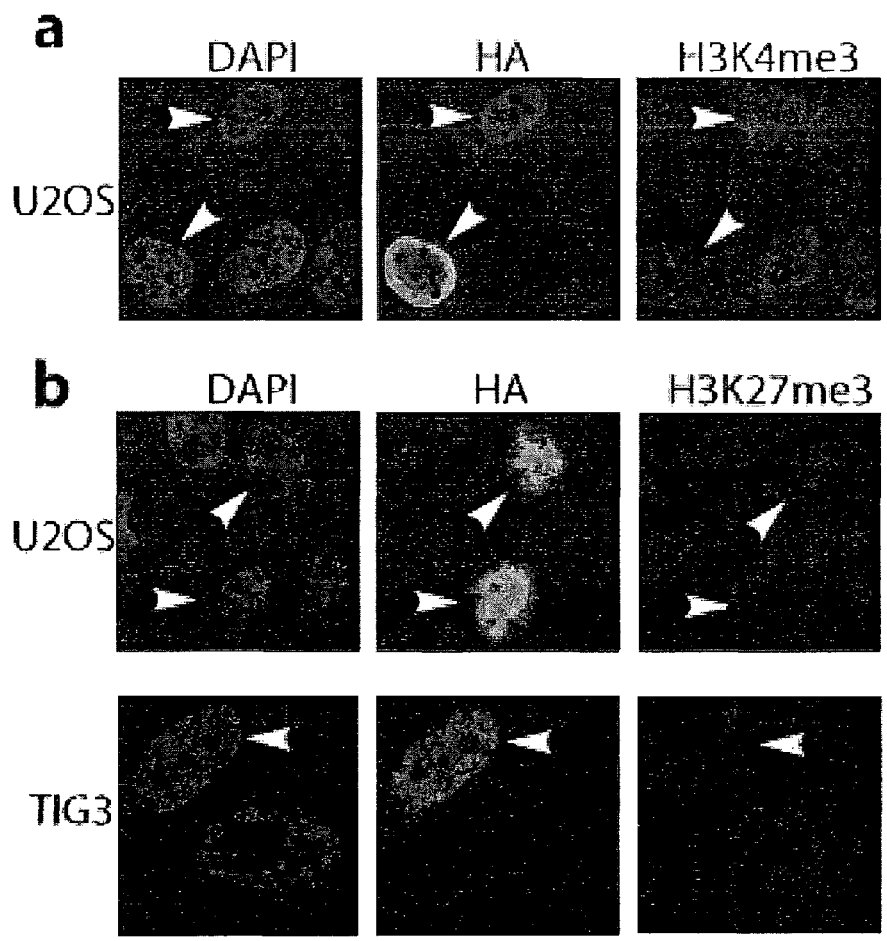
FIG. 27 (S7): α-Ketoglutarate analogues and cobalt and nickel salts inhibit GASC1 demethylation activity. Demethylation assay using recombinant GASC1 and bulk histones as substrates. Histones were incubated with His-GASC1 in the presence of co-factors for 30 min. at 37° C., and in the presence or absence of either (a), CoCl$_2$ or (b) NiSO$_4$ and analyzed by western blot analysis.
Figure 28:
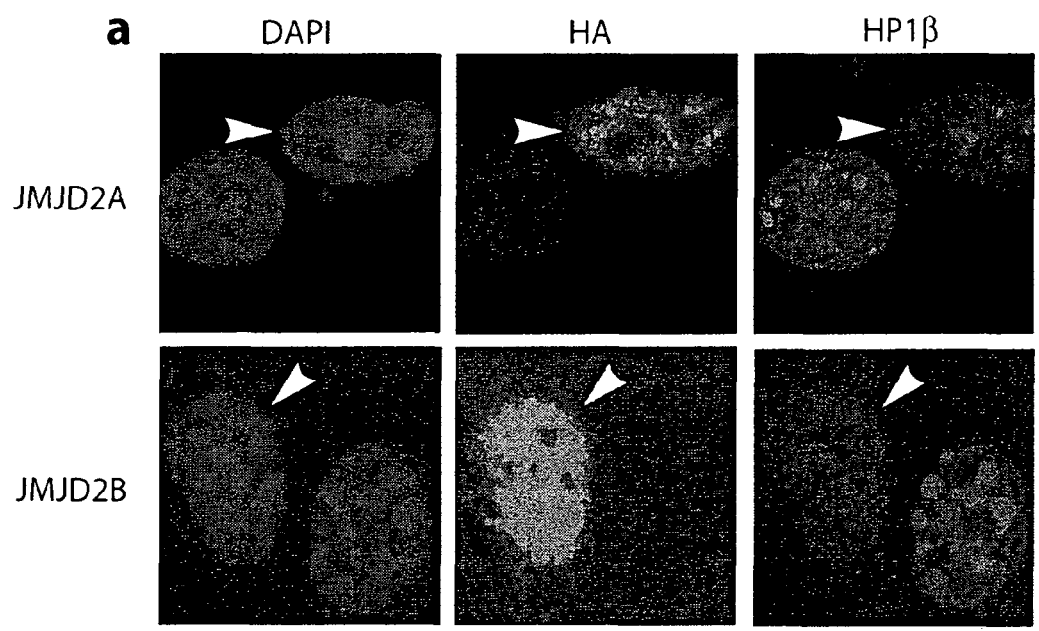
FIG. 28-29 (S8): Ectopic expression of GASC1 does not affect H3K4 and H3K27 methylation. a, H3K4 trimethylation status in U2OS cells overexpressing GASC1 evaluated by immunofluorescence. b, H3K27 trimethylation status in U2OS and Tig3 cells overexpressing GASC1 evaluated by immuno-fluorescence.
Figure 29:
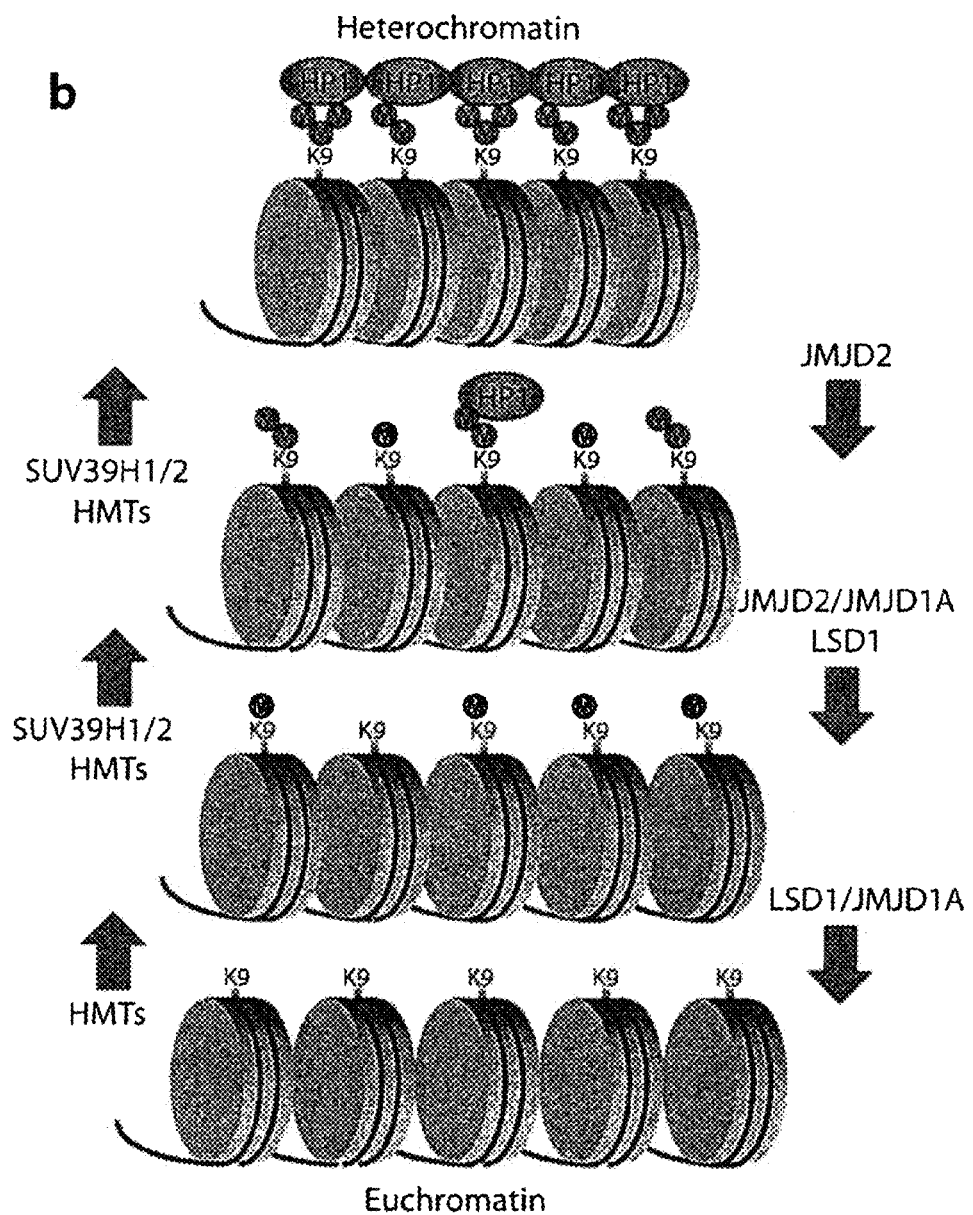
Figure 30:
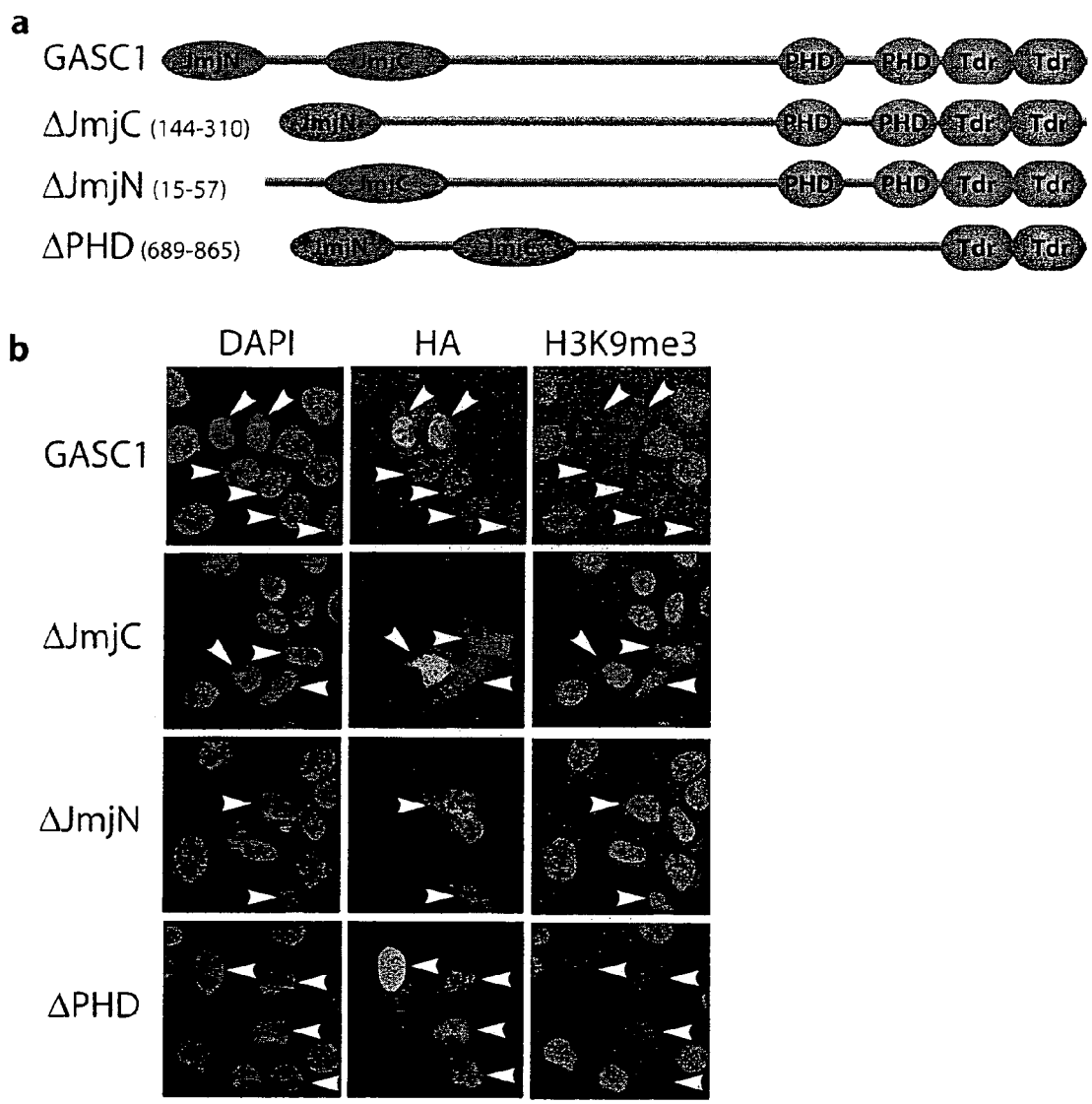
FIG. 30 (S9): Putative role of GASC1 in heterochromatin modelling/plasticity. a, Confocal microscopy of U2OS cells transfected with HA-tagged JMJD2a and JMJD2b. White arrows indicate cells expressing HA-tagged GASC1. HP1 is delocalized in cells over-expressing JMJD2a and JMJD2b. b, Model for GASC1's role in heterochromatin modelling and plasticity. Recruitment of H3K9 specific histone methyltransferases (HMTs) as GLP, G9a and SUV39H1/H2 to chromatin will lead to the progressive methylation of the H3K9 mark. First H3K9 can be mono-methylated, by enzymes as GLP, G9a. Processive HMTs as SUV39H1/H2 can subsequently act to produce di- and tri-methylated H3K9 permitting the binding of HP1. In turn, HP1-binding will lead to further recruitment of HMTs and propagation of heterochromatin. GASC1 may counteract the spreading and formation of heterochromatin by removing the di-methyl and tri-methyl marks hampering HP1-binding. GASC1 may work in concert with other demethylases as LSD1[46] and JMJD2a, b to counter heterochromatin.
Figure 31:
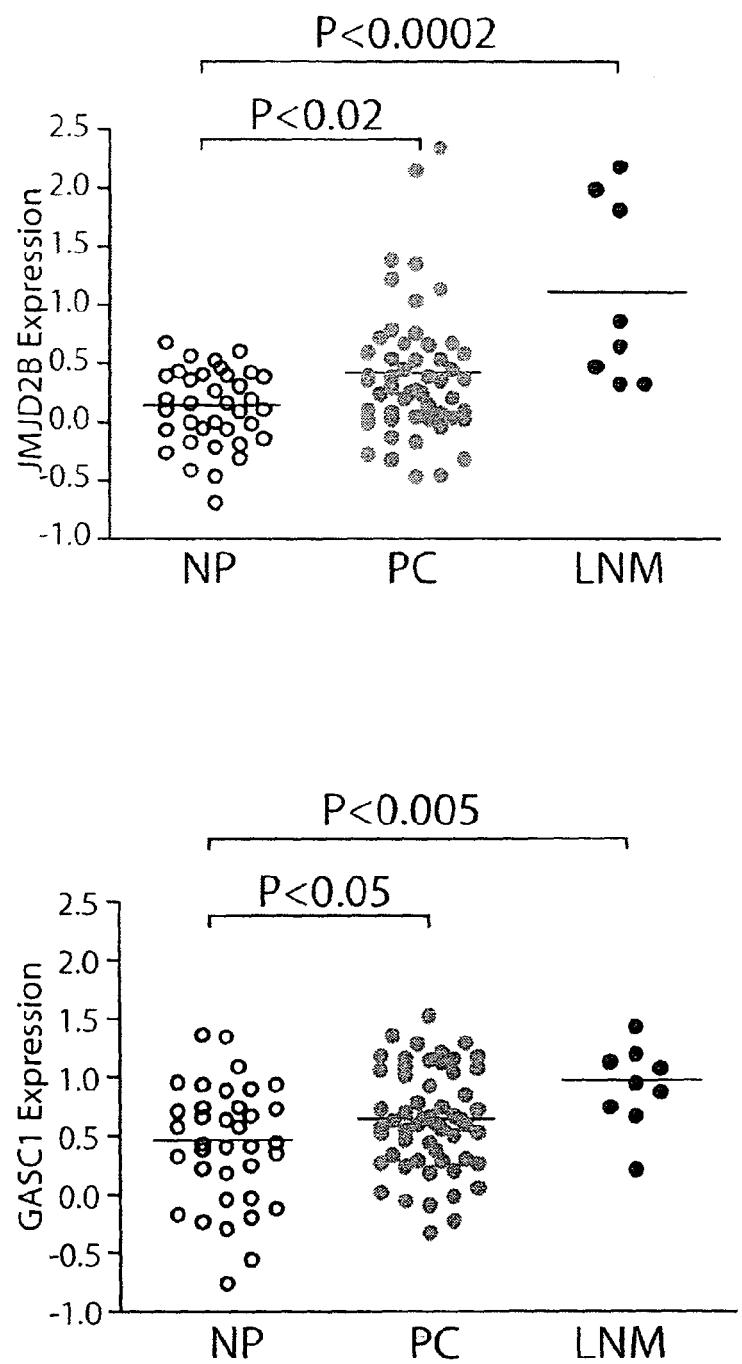
Figure 33:
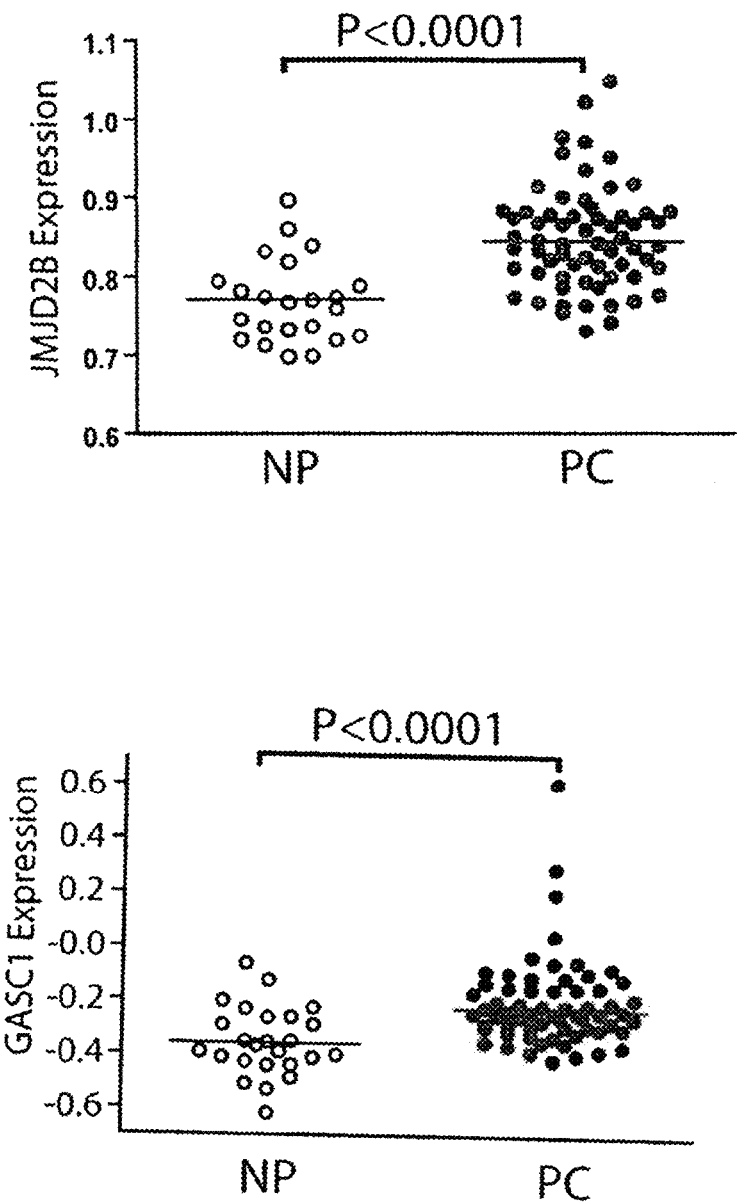

Intriguingly, it was found that quercetin (FIG. 12b), a plant flavanoid associated with anti-proliferative and anti-cancer properties[40-42] was able to effectively inhibit GASC1-mediated demethylation of H3K9me3 in vitro (FIG. 12c). In vivo, overnight treatment of KYSE-150 cells with quercetin caused a staggering increase in H3K9 trimethylation as evidenced by immunofluorescence and western blotting (FIG. 13d and data not shown). The increase of H3K9me3 was accompanied with a marked decrease of growth rate and a senescent-like phenotype characterized by changed cell morphology, appearance of senescence associated heterochromatin foci (SAHFs) and β-gal staining (data not shown). Interestingly quercetin-treatment did not seem to affect the other cell-lines (expressing-low and moderate levels of GASC1) to the same extent. Thus U2OS, WI38 and KYSE-450 cells did not display the same increase in H3K9me3 nor the same senescent-like phenotype and growth inhibition. This result suggests that some cancers characterized by increased expression or activity of JMJD2 enzymes and subsequent decrease of H3K9me3/me2 may be especially susceptible to the growth-inhibitory effect of this compound. The biological effects of quercetin have previously been attributed to inhibition of topoisomerase I[43], modulation of protein and lipid kinase signalling pathways[44] and scavenging of reactive oxygen species[45], In light of the present findings it is tempting to speculate that the anti-cancer effect of quercetin might at least partially by explained by its inhibitory effect on GASC1 and other members of the JMJD2 subfamily.

In summary, using several independent lines of evidence it has been shown that GASC1 directly demethylates the repressive histone di- and tri-methyl H3K9 marks both in vitro and in vivo. The present findings demonstrate that histone tri-methylation is a reversible modification. This finding may potentially have far-reaching implications for human disease, notably cancer.

MATERIALS AND METHODS

Demethylation Assay

Bulk histones, oligonucleosomes or synthetic histone peptides were reacted with purified His-GASC1 in demethylation buffer (50 mM Tris pH 8.0, 50 mM KCl, 10 mM $MgCl_2$, 1 mM α-ketoglutarate, 40 µM $FeSO_4$, 2 mM ascorbic acid, 0.01% (w/v) BSA and 5% (v/v) glycerol) at 37° C. In a typical reaction, either 6 µg bulk histones or 2 µg of modified histone peptides were reacted with 20 µg GASC1 in a volume of 100 µl for 30 minutes. Reaction mixtures were analyzed by either western blotting using specific antibodies, or by formaldehyde-release assays.

Formaldehyde Release Assay.

Formaldehyde release assays were performed essentially as described[4]. All reactions were performed in a total volume of 200 µl per reaction in a quartz cuvette. In short, recombinant GASC1 (typically 40 µg) was incubated in 150 µl demethylation buffer (see above) in the presence of 2 mM NAD+ and 0.2 U formaldehyde dehydrogenase (FDH) for 37° C. for 5 minutes. Then the reaction was started by adding substrates (histone-peptides). The absorbance at 340 nm was measured with 0.5 min intervals (15 min total) using a Genesys 10UV Thermospectronic spectrophotometer at 37° C.

GASC1 demethylation of H3K9me3 peptide for mass spectrometry analysis. Six µg of recombinant GASC1, was incubated with 3 µg H3K9me3 peptide in FDH buffer in a final volume of 90 µl for 30 min at 37° C. Urea was added to a final concentration of 4M and the mixture was incubated at 20° C. for 15 min. An equal volume of 1% TFA was added and the sample loaded on a reversed phase mini C8 column packed in a 100 µl tip (column volume of 20 µl). After washing in 1% TFA, the bound peptide was eluted in 20 µl (30% methanol, 25% formic acid). One third of the eluted material was analysed by SDS page and Western blotting using first anti-H3K9me3, followed by anti-biotin antibody (FIG. 4c). The rest of the material was analysed by mass spectrometry (FIG. 4d).

Mass Spectrometry (MS) Analysis.

One third of the eluate was injected in 1% TFA using an Agilent 1100 Nano HPLC (Palo Alto, Calif.) onto a C18-column (Reprosil-Pur C18-AQ 3 µm; Dr. Maisch GmbH, Ammerbuch-Entringen, germany) packed into a spray emitter (75 µm ID, 8 µm opening, 70 mm length; New Objectives, USA). Peptides were eluted in a gradient from buffer A (5% acetonitrile and 0.5% acetic acid) to buffer B (acetonitrile and 0.5% acetic acid) going from 0 to 20% in 10 min at 300 mL/min. Spectra were recorded on a LTQ-FT mass spectrometer (Thermoelectron, Bremen, Germany).

Supplementary Methods

Materials.

Synthetic peptides 43 amino acids long mimicking the N-terminal tail (1-40) of histone H3 (ARTKQTARKSTG-GKAPRKQLATKAARKSAPATGGVKKPHR-Tyr-Cys-(Ttds)-Lys-biotin). The peptides were synthesized with a C-terminal tyrosine and cysteine for coupling and linked to biotin through lysine and a Ttds spacer. Peptides used in experiments were either unmodified, tri-methylated at lysine 27 or mono-, di-, or tri-methylated at lysine K9 were purchased from Jerini, GMBH Germany. Formaldehyde dehydrogenase (FDH, F1879) and nicotine amine and bulk histones (H9250) were purchased from Sigma. Antibodies used in the study were as follows: anti tri-methylated H3-K9, (Upstate 07-523), anti di-methylated H3-K9 (Upstate 07-212), anti mono-methylated H3-K9 (Abcam Ab9045-50), anti tri-methyl H3-K27 (Upstate 07-449), anti tri-methyl H4-K20 (Upstate 07-463), anti tri-methylated H3-K4, (Abcam ab8580-50), anti di-methylated H3-K4 (Upstate 07-030), anti histone H3 (Abcam Ab1791-100), anti HP1α (Upstate 05-689), anti-HP1γ (upstate 05-690), anti biotin-HRP (Sigma A4541), anti-His (Upstate 05-531) and anti HA (CRP Inc. AFC-101P).

Cell Lines and Tissue Culture.

Human esophageal squamous cell carcinoma cell lines KYSE-70 and 150 were obtained from the German Collection of Microorganisms and Cell Cultures, Braunschweig, Germany. Diploid human fibroblast (TIG-3) expressing hTert and U2OS cells expressing the murine ecotropic retrovirus receptor EcoR were used for the experiments. HEK293 cells stably expressing tetracycline inducible amino-terminally myc-tagged GASC1 was generated using the 293 TRex-flip-in cells essentially as described by the manufacturer (InVitrogen). KYSE cells were maintained in 49% RPMI 1640, 49% Ham's F12 supplemented 2% foetal calf serum (FCS), 5% $CO_2$. All other cells were maintained at 37° C. in Dulbecco's modified Eagle's medium (DMEM) supplemented with 10% foetal calf serum (FCS), 5% $CO_2$.

Histone peptide pulldown of HeLa nuclear proteins Pulldown assays were performed using HeLa cell nuclear extracts and histone H3 peptide tri-methylated at lysine 9 (ART-KQTARK(me3)STGGKAPRKQLATKAA-RKS APATG-GVKKPHR-Tyr-Cys-(Ttds)-Lys-biotin). Nuclei were prepared from HeLa cells, lysed with lysis buffer (50 mM Tris, pH 7.2, 300 mM NaCl, 0.5% IGEPAL CA-630, 1 mM EDTA (pH 8.0), 1 mM PMSF containing protease inhibitors). The lysate was pre-cleared with uncoupled streptavidin beads (Fig. S1, preclearing 1) and then with streptavidin beads coupled to unmodified H3 histone (Fig. S1, preclearing 2). The pre-cleared lysate was then incubated with H3 histone peptide trimethylated at K9 (H3K9me3), precoupled to streptavidin beads. Beads were washed avidly and bound proteins were subsequently eluted from the resin with 2×LSB buffer (100 mM Tris-HCl pH 6.8, 200 mM DTT, 4% SDS, 20% glycerol and 0.2% bromphenolblue), Figure S, H3K9me3. Proteins were resolved by SDS PAGE and visualized by silver staining. Protein bands enriched in the H3K9me3 pull-down were excised, in-gel digested with trypsin and analyzed by nanoelectrospray tandem mass spectrometry as described by Wilm et al. (Wilm M. (1996) Nature 379, 466-469). Immunofluorescense Confocal immunostainings were done essentially as described by Sørensen, C. S. et al., *Nat. Cell. Biol.* 7, 195-201 (2005).

Preparation of Cell Lysates.

Total lysates of cells were generated from the same number of cells lysed in urea buffer (1% SDS, 9M urea, 25 mM Tris-HCl, pH 6.8, 1 mM EDTA, 0.7 M β-mercaptoethanol), boiled for 5 min. and sonicated. For chromatin fractionation an equal number of cells were incubated 30 min. on ice in 200 µl pre-extraction buffer (20 mM Hepes-KOH, pH 7.2 containing 0.5% IGEPAL-630, 50 mM NaCl, 3 mM $MgCl_2$ and 300 mM sucrose). 100 µl was mixed with 2×LSB buffer (100 mM Tris-HCl pH 6.8, 200 mM DTT, 4% SDS, 20% glycerol and 0.2% bromphenolblue), boiled, sonicated and used as total lysate. The remaining 100 µl was spun down at 1300×g for 10 min at 4° C., washed in 1 ml pre-extraction buffer, re-suspended in 100 µl 2×LSB buffer, boiled, sonicated and used as chromatin fraction.

siRNA and shRNA to GASC1 and JMJD2a/b.

Small interfering RNA (siRNA) oligonucleotides to GASC1 and its homologs JMJD2a and JMJD2b were synthesized by Dharmacon Research, Inc. Cells ($1 \times 10^5$/well) were transfected with siRNA oligos (0.3 µg/well) in 6-well plates using Oligofectamine reagent (Invitrogen) following the manufacturer's protocol. SiRNA can be designed according to procedures known in the art for instance using the SiRNA retriever; (http://katahdin.cshl.org:9331/homepage/siRNA/RNAi.cgi?type=siRNA).

ShRNA Constructs

Short hairpin RNA constructs were generated in the MSCV/LTRmiR30-PIG (LMP) vector (Dickens N G et al (2005) "Probing tumor phenotypes using stable and regulated synthetic microRNA precursors" Nature Genetics Vol 37, No 11 1289-1295.) according to the procedure described in Paddison et al. (2005) (Paddison P J, Cleary M, Silva J M, Chang K, Sheth N, Sachidanandam R & Hannon G J. Cloning of short hairpin RNAs for gene knockdown in mammalian cells Nature methods pp 163-167).

Three oligonucleotides were designed using the "shRNA retriever" (http://katahdin.cshl.org:9331/homepage/siRNA/RNAi.cgi?type=shRNA). Using the oligonucleotide TGCT-GTTGACAGTGAGCG CGCCAGATAGCAGCAATGAAGATAG-TGAAGCCA-CAGATGTATCTTCATTGCTGCTATCTGGCTTGCCT-ACTGCCTCGGA as template a 150 bp PCR product was amplified, digested with XhoI and EcoRI and ligated into the digested LMP vector. The shRNA construct targets a 22 bp sequence at position 2117 in the GASC1 coding sequence, underlined in the above sequence. The efficiency of the shRNAi construct to knock-down the GASC1 mRNA was estimate as approximately 80% as assessed by real-time quantitative RT-PCR.

Real-Time Quantitative RT-PCR

Cells were transfected with the indicated shRNA constructs and subjected to a brief puromycin selection (2 µg/ml). Total RNA was made from transfected cells using the Quiagen RNAeasy mini kit according to the manufacturers instructions. cDNA was generated using the Taqman reverse transcription kit and poly dT primer according to the manufacturers instructions. The cDNA was used as template in real-time quantitative PCR reactions with GASC1 specific primers on a Applied biosystems 7700. The reactions were prepared using 2×SYBR green reaction mix from Applied biosystems.

BrdU Incorporation.

Thirty hours after transfection of siRNA, the cells were split into 4-well chamber slides and incubated with culture medium containing BrdU for 15-30 min.

cDNA Cloning of Human GASC1.

The putative open reading frames of human GASC1 and JMJD2A were amplified by PCR from HeLa cDNA and cDNA from a human foetal brain cDNA library (Invitrogen, Carlsbad, Calif.). Primer sequences are available upon request. PCR products were gel purified, cloned into pCR8/GW (Invitrogen), and verified by DNA sequencing. Using these Gateway-compatible entry clones GASC1 and JMJD2A were transferred into pCMV-HA, pCMV-myc and pBabepuro. A double mutant in the conserved iron-binding domain (HTE) of GASC1 changing amino acids 190-192 from histidine, threonine and glutamic acid respectively to glycine, threonine and alanine was generated using standard mutagenesis methods.

Recombinant Proteins.

Full-length amino-terminally hexahistidine-tagged human GASC1 baculovirus transfer vector was generated by Gateway-mediated transfer of GASC1 cDNA from pCR8/GW and into a Gateway-modified form of pAcHLT-A (Pharmingen). Recombinant baculoviruses were generated by cotransfection of baculovirus transfer vector containing the GASC1 gene and Bsu36I linearized Bakpak6 baculovirus DNA essentially as previously described. Histidine-tagged GASC1 and JMJD2A was expressed and purified by cobalt-affinity chromatography essentially as described previously (Christensen et al. *Nucleic Acids Research* 33, 5458-5470 (2005)). The eluted fractions were analyzed by SDS-PAGE and selected fractions were subjected to further purification by size exclusion chromatography (SEC). In short, SEC was performed on a Superose 12, 10/300 column (Pharmacia-Amersham) equilibrated with 25 mM HEPES-KOH, pH 7.7, containing 50 mM NaCl and eluted with the same buffer at a flow-rate of 0.3 ml/min. Eluted material was collected in 0.5 ml fractions, flash frozen in liquid $N_2$, and stored at −80° C. All procedures were performed on ice or at 4° C. in the presence of complete EDTA-free protease inhibitor (Boehringer Mannheim, Germany).

Retrovirus Transduction.

To generate recombinant retroviruses expressing GASC1 and its mutant H190G/E192A, the open reading frame of GASC1 was transferred into pBabepuro by Gateway-mediated recombination generating pBabepuro-HA-GASC1, and pBabepuro-HA-H190G/E192A. High titers of retroviral particles were obtained 24-48 hours after transfection of the Phoenix-Eco 293 cell packing cell line. Transfections were done using the calcium phosphate method. Transduction of TIG3-hTert-EcoR cells or U2OS-EcoR cells was achieved by adding virus containing supernatants from the packaging cell line to the cell dishes four times within a 24 hour period. Transduced cells were selected for 2-5 days in the presence puromycin (1 µg/µl).

Molecular Modelling

The structure of FIH complexed with α-ketoglutarate, CAD peptide and iron was available in Protein Data Bank (PDB, Brookhaven National Library, Upton N.Y., USA) with accession number 1H2K. $GASC1_{22-349}$ was homology-modelled with FIH as template using homology module INSIGHT II (2005) (Accelrys, San Diego). The histone tail (ARTKQTARKSTG) was modelled with the CAD peptide, as template. The program GRID (Version 22, Molecular Discovery Ltd., Oxford, UK) (Goodford, 1985) was used to compute the hydrophobic surface contours of the GASC1 molecule. The histone peptide was subsequently docked onto the hydrophobic surface contours of GASC1 using AUTODOCK (Ver. 3.0.5, Scripps Research Institute and Molecular Graphics Laboratory). Finally structural models of the complexes were drawn with Pymol (http://pymol.sourceforge.net/).

Supplementary Methods

Materials. Synthetic peptides 43 amino acids long mimicking the N-terminal tail (1-40) of histone H3 (ARTKQTARK-STGGKAPRKQLATKAARKSAPATGGVKKPHR-Tyr-Cys-(Ttds)-Lys-biotin). The peptides were synthesized with a C-terminal tyrosine and cysteine for coupling and linked to biotin through lysine and a Ttds spacer. Peptides used in experiments were either unmodified, tri-methylated at lysine 27 or mono-, di-, or tri-methylated at lysine K9 were purchased from Jerini, GMBH Germany. Formaldehyde dehydrogenase (FDH, F1879) and nicotine amine and bulk histones (H9250) were purchased from Sigma. Antibodies used in the study were as follows: anti tri-methylated H3-K9, (Upstate 07-523), anti di-methylated H3-K9 (Upstate 07-212), anti mono-methylated H3-K9 (Abcam Ab9045-50), anti tri-methyl H3-K27 (Upstate 07-449), anti tri-methyl H4-K20 (Upstate 07-463), anti tri-methylated H3-K4, (Abcam ab8580-50), anti di-methylated H3-K4 (Upstate 07-030), anti histone H3 (Abcam Ab1791-100), anti HP1α (Upstate 05-689), anti-HP1γ (upstate 05-690), anti biotin-HRP (Sigma A4541), anti-H is (Upstate 05-531) and anti HA (CRP Inc. AFC-101P).

Cell Lines and Tissue Culture.

Human esophageal squamous cell carcinoma cell lines KYSE-70 and 150 were obtained from the German Collection of Microorganisms and Cell Cultures, Braunschweig, Germany. Diploid human fibroblast (TIG-3) expressing hTert and U2OS cells expressing the murine ecotropic retrovirus receptor EcoR were used for the experiments. HEK293 cells stably expressing tetracycline inducible amino-terminally myc-tagged GASC1 was generated using the 293 TRex-flip-in cells essentially as described by the manufacturer (InVitrogen). KYSE cells were maintained in 49% RPMI 1640, 49% Ham's F12 supplemented 2% foetal calf serum (FCS), 5% $CO_2$. All other cells were maintained at 37° C. in Dulbecco's modified Eagle's medium (DMEM) supplemented with 10% foetal calf serum (FCS), 5% $CO_2$.

Histone peptide pulldown of HeLa nuclear proteins Pulldown assays were performed using HeLa cell nuclear extracts and histone H3 peptide tri-methylated at lysine 9 (ART-KQTARK(me3)STGGKAPRKQLATKAA-RKS APATG-GVKKPHR-Tyr-Cys-(Ttds)-Lys-biotin). Nuclei were prepared from HeLa cells, lysed with lysis buffer (50 mM Tris, pH 7.2, 300 mM NaCl, 0.5% IGEPAL CA-630, 1 mM EDTA (pH 8.0), 1 mM PMSF containing protease inhibitors). The lysate was pre-cleared with uncoupled streptavidin beads (Fig. S1, preclearing 1) and then with streptavidin beads coupled to unmodified H3 histone (Fig. S1, preclearing 2). The pre-cleared lysate was then incubated with H3 histone peptide trimethylated at K9 (H3K9me3), precoupled to streptavidin beads. Beads were washed avidly and bound proteins were subsequently eluted from the resin with 2×LSB buffer (100 mM Tris-HCl pH 6.8, 200 mM DTT, 4% SDS, 20% glycerol and 0.2% bromphenolblue), Figure S1, H3K9me3. Proteins were resolved by SDS PAGE and visualized by silver staining. Protein bands enriched in the H3K9me3 pull-down were excised, in-gel digested with trypsin and analyzed by nanoelectrospray tandem mass spectrometry as described by Wilm et al. (Wilm M. (1996) Nature 379, 466-469). Immunofluorescence Confocal immunostainings were done essentially as described by Sørensen, C. S. et al., *Nat. Cell. Biol.* 7, 195-201 (2005).

Preparation of Cell Lysates.

Total lysates of cells were generated from the same number of cells lysed in urea buffer (1% SDS, 9M urea, 25 mM Tris-HCl, pH 6.8, 1 mM EDTA, 0.7 M β-mercaptoethanol), boiled for 5 min. and sonicated. For chromatin fractionation an equal number of cells were incubated 30 min. on ice in 200p, pre-extraction buffer (20 mM Hepes-KOH, pH 7.2 containing 0.5% IGEPAL-630, 50 mM NaCl, 3 mM $MgCl_2$ and 300 mM sucrose). 100 μl was mixed with 2×LSB buffer (100 mM Tris-HCl pH 6.8, 200 mM DTT, 4% SDS, 20% glycerol and 0.2% bromphenolblue), boiled, sonicated and used as total lysate. The remaining 100 μl was spun down at 1300×g for 10 min at 4° C., washed in 1 ml pre-extraction buffer, re-suspended in 100 μl 2×LSB buffer, boiled, sonicated and used as chromatin fraction.

siRNA and shRNA to GASC1 and JMJD2a/b.

Small interfering RNA(siRNA) oligonucleotides to GASC1 and its homologs JMJD2a and JMJD2b were synthesized by Dharmacon Research, Inc. Cells ($1\times10^5$/well) were transfected with siRNA oligos (0.3 μg/well) in 6-well plates using Oligofectamine reagent (Invitrogen) following the manufacturer's protocol. SiRNA can be designed according to procedures known in the art for instance using the SiRNA retriever; (http://katahdin.cshl.org:9331/homepage/siRNA/RNAi.cgi?type=siRNA).

ShRNA Constructs

Short hairpin RNA constructs were generated in the MSCV/LTRmiR30-PIG (LMP) vector (Dickens N G et al (2005) "Probing tumor phenotypes using stable and regulated synthetic microRNA precursors" Nature Genetics Vol 37, No 11 1289-1295.) according to the procedure described in Paddison et al. (2005) (Paddison P J, Cleary M, Silva J M, Chang K, Sheth N, Sachidanandam R & Hannon G J. Cloning of short hairpin RNAs for gene knockdown in mammalian cells Nature methods pp 163-167).

Three oligonucleotides were designed using the "shRNA retriever" (http://katahdin.cshl.org:9331/homepage/siRNA/RNAi.cgi?type=shRNA). Using the oligonucleotide TGCT-GTTGACAGTGAGCG CGCCAGATAGCAGCAATGAAGATAG-TGAAGCCA-CAGATGTATCTTCATTGCTGCTATCTGGCTTG-CCTACTGCCTCGGA as template a 150 bp PCR product was amplified, digested with XhoI and EcoRI and ligated into the digested LMP vector. The shRNA construct targets a 22 bp sequence at position 2117 in the GASC1 coding sequence, underlined in the above sequence. The efficiency of the shRNAi construct to knock-down the GASC1 mRNA was estimate as approximately 80% as assessed by real-time quantitative RT-PCR.

Real-Time Quantitative RT-PCR

Cells were transfected with the indicated shRNA constructs and subjected to a brief puromycin selection (2 μg/ml). Total RNA was made from transfected cells using the Quiagen RNAeasy mini kit according to the manufacturers instructions. cDNA was generated using the Taqman reverse transcription kit and poly dT primer according to the manufacturers instructions. The cDNA was used as template in real-time quantitative PCR reactions with GASC1 specific primers on a Applied biosystems 7700. The reactions were prepared using 2×SYBR green reaction mix from Applied biosystems.

BrdU Incorporation.

Thirty h after transfection of siRNA, the cells were split into 4-well chamber slides and incubated with culture medium containing BrdU for 15-30 min.

cDNA Cloning of Human GASC1.

The putative open reading frames of human GASC1 and JMJD2A were amplified by PCR from HeLa cDNA and cDNA from a human foetal brain cDNA library (Invitrogen, Carlsbad, Calif.). Primer sequences are available upon request. PCR products were gel purified, cloned into pCR8/GW (Invitrogen), and verified by DNA sequencing. Using these Gateway-compatible entry clones GASC1 and JMJD2A were transferred into pCMV-HA, pCMV-myc and pBabepuro. A double mutant in the conserved iron-binding domain (HTE) of GASC1 changing amino acids 190-192 from histidine, threonine and glutamic acid respectively to glycine, threonine and alanine was generated using standard mutagenesis methods.

Recombinant Proteins.

Full-length amino-terminally hexahistidine-tagged human GASC1 baculovirus transfer vector was generated by Gateway-mediated transfer of GASC1 cDNA from pCR8/GW and into a Gateway-modified form of pAcHLT-A (Pharmingen). Recombinant baculoviruses were generated by cotransfection of baculovirus transfer vector containing the GASC1 gene and Bsu36I linearized Bakpak6 baculovirus DNA essentially as previously described. Histidine-tagged GASC1 and JMJD2A was expressed and purified by cobalt-affinity chromatography essentially as described previously (Christensen et al. *Nucleic Acids Research* 33, 5458-5470 (2005)). The eluted fractions were analyzed by SDS-PAGE and selected fractions were subjected to further purification by size exclusion chromatography (SEC). In short, SEC was performed on a Superose 12, 10/300 column (Pharmacia-Amersham) equilibrated with 25 mM HEPES-KOH, pH 7.7, containing 50 mM NaCl and eluted with the same buffer at a flow-rate of 0.3 ml/min. Eluted material was collected in 0.5 ml fractions, flash frozen in liquid $N_2$, and stored at −80° C. All procedures were performed on ice or at 4° C. in the presence of complete EDTA-free protease inhibitor (Boehringer Mannheim, Germany).

Retrovirus Transduction.

To generate recombinant retroviruses expressing GASC1 and its mutant H190G/E192A, the open reading frame of GASC1 was transferred into pBabepuro by Gateway-mediated recombination generating pBabepuro-HA-GASC1, and pBabepuro-HA-H190G/E192A. High titers of retroviral particles were obtained 24-48 hours after transfection of the Phoenix-Eco 293 cell packing cell line. Transfections were done using the calcium phosphate method. Transduction of TIG3-hTert-EcoR cells or U2OS-EcoR cells was achieved by adding virus containing supernatants from the packaging cell line to the cell dishes four times within a 24 hour period. Transduced cells were selected for 2-5 days in the presence puromycin (1 µg/µl).

Molecular Modelling

The structure of FIH complexed with α-ketoglutarate, CAD peptide and iron was available in Protein Data Bank (PDB, Brookhaven National Library, Upton N.Y., USA) with accession number 1H2K. $GASC1_{22-349}$ was homology-modelled with FIH as template using homology module INSIGHT II (2005) (Accelrys, San Diego). The histone tail (ARTKQTARKSTG) was modelled with the CAD peptide, as template. The program GRID (Version 22, Molecular Discovery Ltd., Oxford, UK) (Goodford, 1985) was used to compute the hydrophobic surface contours of the GASC1 molecule. The histone peptide was subsequently docked onto the hydrophobic surface contours of GASC1 using AUTODOCK (Ver. 3.0.5, Scripps Research Institute and Molecular Graphics Laboratory). Finally structural models of the complexes were drawn with Pymol (http://pymol.sourceforge.net/).

REFERENCES

1. Fischle, W., Wang, Y. & Allis, C. D. Histone and chromatin cross-talk. Curr Opin Cell Biol 15, 172-83 (2003).
2. Margueron, R., Trojer, P. & Reinberg, D. The key to development: interpreting the histone code? Curr Opin Genet Dev 15, 163-76 (2005).
3. Peterson, C. L. & Laniel, M. A. Histones and histone modifications. Curr Biol 14, R546-51 (2004).
4. Shi, Y. et al. Histone demethylation mediated by the nuclear amine oxidase homolog LSD1. Cell 119, 941-53 (2004).
5. Tsukada, Y. et al. Histone demethylation by a family of JmjC domain-containing proteins. Nature 439, 811-6 (2006).
6. Peters, A. H. et al. Loss of the Suv39h histone methyltransferases impairs mammalian heterochromatin and genome stability. Cell 107, 323-37 (2001).
7. Bannister, A. J. & Kouzarides, T. Reversing histone methylation. Nature 436, 1103-6 (2005).
8. Clissold, P. M. & Ponting, C. P. JmjC: cupin metalloenzyme-like domains in jumonji, hairless and phospholipase A2beta. Trends Biochem Sci 26, 7-9 (2001).
9. Katoh, M. & Katoh, M. Identification and characterization of JMJD2 family genes in silico. Int J Oncol 24, 1623-8 (2004).
10. Ayoub, N. et al. A novel jmjC domain protein modulates heterochromatization in fission yeast. Mol Cell Biol 23, 4356-70 (2003).
11. Dann, C. E., 3rd, Bruick, R. K. & Deisenhofer, J. Structure of factor-inhibiting hypoxia-inducible factor 1: An asparaginyl hydroxylase involved in the hypoxic response pathway. Proc Natl Acad Sci USA 99, 15351-6 (2002).
12. Gray, S. G. et al. Functional characterization of JMJD2A, a histone deacetylase- and retinoblastoma-binding protein. J Biol Chem 280, 28507-18 (2005).
13. Kim, T. G., Chen, J., Sadoshima, J. & Lee, Y. Jumonji represses atrial natriuretic factor gene expression by inhibiting transcriptional activities of cardiac transcription factors. Mol Cell Biol 24, 10151-60 (2004).
14. Kim, T. G., Kraus, J. C., Chen, J. & Lee, Y. JUMONJI, a critical factor for cardiac development, functions as a transcriptional repressor. J Biol Chem 278, 42247-55 (2003).
15. Schofield, C. J. & Zhang, Z. Structural and mechanistic studies on 2-oxoglutarate-dependent oxygenases and related enzymes. Curr Opin Struct Biol 9, 722-31 (1999).
16. Trewick, S. C., McLaughlin, P. J. & Allshire, R. C. Methylation: lost in hydroxylation? EMBO Rep 6, 315-20 (2005).
17. Knowles, H. J., Raval, R. R., Harris, A. L. & Ratcliffe, P. J. Effect of ascorbate on the activity of hypoxia-inducible factor in cancer cells. Cancer Res 63, 1764-8 (2003).
18. Lee, C., Kim, S. J., Jeong, D. G., Lee, S. M. & Ryu, S. E. Structure of human F1H-1 reveals a unique active site pocket and interaction sites for HIF-1 and von Hippel-Lindau. J Biol Chem 278, 7558-63 (2003).
19. Elkins, J. M. et al. Structure of factor-inhibiting hypoxia-inducible factor (HIF) reveals mechanism of oxidative modification of HIF-1 alpha. J Biol Chem 278, 1802-6 (2003).
20. Hegg, E. L. & Que, L., Jr. The 2-His-1-carboxylate facial triad—an emerging structural motif in mononuclear non-heme iron(II) enzymes. Eur J Biochem 250, 625-9 (1997).
21. Kivirikko, K. I. & Myllyharju, J. Prolyl 4-hydroxylases and their protein disulfide isomerase subunit. Matrix Biol 16, 357-68 (1998).
22. Myllyla, R., Majamaa, K., Gunzler, V., Hanauske-Abel, H. M. & Kivirikko, K. I. Ascorbate is consumed stoichiometrically in the uncoupled reactions catalyzed by prolyl 4-hydroxylase and lysyl hydroxylase. J Biol Chem 259, 5403-5 (1984).
23. Wilmouth, R. C. et al. Structure and mechanism of anthocyanidin synthase from *Arabidopsis thaliana*. Structure 10, 93-103 (2002).
24. Zhou, J. et al. Spectroscopic studies of substrate interactions with clavaminate synthase 2, a multifunctional alpha-KG-dependent non-heme iron enzyme: correlation with mechanisms and reactivities. J Am Chem Soc 123, 7388-98 (2001).
25. Bannister, A. J. et al. Selective recognition of methylated lysine 9 on histone H3 by the HP1 chromo domain. Nature 410, 120-4 (2001).
26. Elgin, S. C. & Grewal, S. I. Heterochromatin: silence is golden. Curr Biol 13, R895-8 (2003).
27. Lachner, M., O'Carroll, D., Rea, S., Mechtler, K. & Jenuwein, T. Methylation of histone H3 lysine 9 creates a binding site for HP1 proteins. Nature 410, 116-20 (2001).
28. Kubicek, S. & Jenuwein, T. A crack in histone lysine methylation. Cell 119, 903-6 (2004).
29. Maurer-Stroh, S. et al. The Tudor domain 'Royal Family': Tudor, plant Agenet, Chromo, PWWP and MBT domains. Trends Biochem Sci 28, 69-74 (2003).
30. Ragvin, A. et al. Nucleosome binding by the bromodomain and PHD finger of the transcriptional cofactor p300. J Mol Biol 337, 773-88 (2004).
31. Huyen, Y. et al. Methylated lysine 79 of histone H3 targets 53BP1 to DNA double-strand breaks. Nature 432, 406-11 (2004).
32. Pidoux, A. L. & Allshire, R. C. The role of heterochromatin in centromere function. Philos Trans R Soc Lond B Biol Sci 360, 569-79 (2005).
33. Yang, Z. Q. et al. Identification of a novel gene, GASC1, within an amplicon at 9p23-24 frequently detected in esophageal cancer cell lines. Cancer Res 60, 4735-9 (2000).
34. Yang, Z. Q. et al. A novel amplicon at 9p23-24 in squamous cell carcinoma of the esophagus that lies proximal to GASC1 and harbors NFIB. Jpn J Cancer Res 92, 423-8 (2001).
35. Soejima, H. et al. Silencing of imprinted CDKN1C gene expression is associated with loss of CpG and histone H3 lysine 9 methylation at DMR-LIT1 in esophageal cancer. Oncogene 23, 4380-8 (2004).
36. Braig, M. et al. Oncogene-induced senescence as an initial barrier in lymphoma development. Nature 436, 660-5 (2005).
37. Chen, Z. et al. Crucial role of p53-dependent cellular senescence in suppression of Pten-deficient tumorigenesis. Nature 436, 725-30 (2005).
38. Collado, M. et al. Tumour biology: senescence in premalignant tumours. Nature 436, 642 (2005).
39. Michaloglou, C. et al. BRAFE600-associated senescence-like cell cycle arrest of human naevi. Nature 436, 720-4 (2005).
40. Welford, R. W., Schlemminger, I., McNeill, L. A., Hewitson, K. S. & Schofield, C. J. The selectivity and inhibition of AlkB. J Biol Chem 278, 10157-61 (2003).
41. Lee, T. 3. et al. Quercetin arrests G2/M phase and induces caspase-dependent cell death in U937 cells. Cancer Lett (2005).
42. Yoshida, M., Yamamoto, M. & Nikaido, T. Quercetin arrests human leukemic T-cells in late G1 phase of the cell cycle. Cancer Res 52, 6676-81 (1992).
43. Das, B. B. et al. Differential induction of *Leishmania donovani* bi-subunit topoisomerase I-DNA cleavage complex by selected flavones and camptothecin: activity of flavones against camptothecin-resistant topoisomerase 1. Nucleic Acids Res 34, 1121-32 (2006).
44. Spencer, J. P., Rice-Evans, C. & Williams, R. J. Modulation of pro-survival Akt/protein kinase B and ERK1/2 signaling cascades by quercetin and its in vivo metabolites underlie their action on neuronal viability. 3 Biol Chem 278, 34783-93 (2003).
45. Chen, J. & Kang, J. H. Quercetin and trichostatin A cooperatively kill human leukemia cells. Pharmazie 60, 856-60 (2005).
46. Metzger, E. et al. LSD1 demethylates repressive histone marks to promote androgen-receptor-dependent transcription. Nature 437, 436-9 (2005).
47. Remington's Pharmaceutical Sciences 16th edition, Osol, A. Ed. (1980)
48. Bowie et al. Science 247 (1990) 1306-1310
49. Merrifield, R. B. (1963), *J. Amer. Chem. Soc.* 85, 2149-2154)
50. Kent, S. B. H. (1988), *Annu. Rev. Biochem.* 57, 957-989
51. Carpino, L. A. and Han, G. Y. (1972), *J. Org. Chem.* 37, 3404-3409
52. Stewart, J. M. and Young, J. D. (1983), "Solid Phase Peptide Synthesis", Pierce Chemical Company, Rockford, Ill.
53. Atherton, E. and Sheppard, R. C. (1989), "Solid Phase Peptide Synthesis", IRL Press at Oxford University Press
54. Pennington, M. W. and Dunn, B. M. (eds.) (1994), "Peptide Synthesis Protocols", Humana Press, Totowa, N.J.
55. Pessi, A. et al. Totally solid phase synthesis of peptide(s)-containing retro-inverted peptide bond, using crosslinked sarcosinyl copolymer as support. European Patent 97994-B, 30 Sep. 1987 (8739).
56. Verdini, A. S. & Viscomi, G. C. (1985) Synthesis, resolution, and assignment of configuration of potent hypotensive retro-inverso bradykinin potentiating peptide 5a (BPP5a) analogues. 3. Chem. Soc. Perkin Trans. I, 697-701.
57. Bonelli, F. et al. (1984) Solid phase synthesis of retro-inverso peptide analogues. Int. J. Peptide Protein Res., 24, 553-556.
58. LetunicI, Copley R R, Pils B, Pinkert S, Schultz, J, Bork P SMART 5: domains in the context of genomes and networks. Nucleic acid Research (2006) January 1: 34: D257-60.
59. Schultz 3, Milpetz F, Bork P, Ponting C P SMART, a simple modular architecture research tool: identification of signaling domains. Proc Natl Acad Sci USA. 1998 May 26; 95(11):5857-64.

The invention claimed is:

1. A method of testing the ability of a test compound to modulate the activity of a polypeptide of the JMJD2 subfamily of Jumonji proteins, said method comprising incubating a test compound with a polypeptide of the JMJD2 subfamily of Jumonji proteins, a co-factor of said polypeptide and a substrate for demethylation.

2. The method according to claim 1, wherein said polypeptide of the JMJD2 subfamily of Jumonji proteins is selected from the group comprising:
   a) the amino acid sequence of SEQ ID NO: 1;
   b) a fragment of at least 100 amino acids of the amino acid sequence of SEQ ID NO: 1;
   c) an amino acid having at least 45% sequence identity to either the sequence in a) or the sequence in b), or both.

3. The method according to claim 1, wherein said polypeptide of the JMJD2 subfamily of Jumonji proteins is selected from the group comprising:
   a) the amino acid sequences of SEQ ID NO: 1 (GASC-1 (JMJD2c)), SEQ ID NO: 2 (JMJD2a), SEQ ID NO: 3 (JMJD2b);
   b) a fragment of at least 100 amino acids of any one of the amino acid sequences in a);
   c) an amino acid having at least 75% sequence identity to any one of the sequences in a) and/or any one of the sequences in b).

4. The method according to claim 1, wherein said polypeptide of the JMJD2 subfamily of jumonji proteins comprises one or more amino acid sequences (domains) selected from the group consisting of: SEQ ID NOs: 4, 10 and 16 (JmjN), SEQ ID NO: 5, 11 and 17 (JmjC), SEQ ID NO: 6, 7, 12, 13, 18 and 19 (PHD), and SEQ ID NO: 8, 9, 14, 15, 20 and 21 (Tdr/TUDOR).

5. The method according to claim 1, said method comprising the additional steps of:
  a) monitoring in a test sample any of the following parameters:
    i) the methylation state of the substrate;
    ii) the release of formaldehyde;
    iii) the carboxylation state of an α-ketoglutarate substrate co-factor;
    iv) the oxygen consumption
  b) comparing the values obtained for the test sample in step a) with values obtained for a control sample, thereby determining the ability of the test compound to modulate the activity of a polypeptide of the JMJD2 subfamily of Jumonji proteins.

6. The method according to claim 5, wherein the control is provided by the following steps:
  a) Incubating a polypeptide of the JMJD2 subfamily of Jumonji proteins and a substrate for demethylation under conditions allowing demethylation
  b) monitoring any of the following parameters in a test sample:
    i) the methylation state of the substrate;
    ii) the release of formaldehyde in a test sample;
    iii) the carboxylation state of an α-ketoglutarate substrate co-factor;
    iv) the oxygen consumption.

7. The method according to claim 5, wherein incubation time and methylation state of the substrate and/or the release of formaldehyde are used to determine a rate of demethylation, which is used for comparison.

8. The method according to claim 1, wherein the substrate for demethylation comprises a methylated site corresponding to lysine 9 on histone H3.

9. The method according to claim 1, wherein the substrate for demethylation is a peptide comprising the amino acid sequence of SEQ ID NO: 25 (RQIKIWFQNRRMKWKK), the lysine residue in said amino acid sequence being methylated.

10. The method according to claim 1, wherein the substrate for demethylation is a peptide of at least 15 amino acid residues.

11. The method according to claim 1, wherein the substrate for demethylation is a peptide of at least 20 amino acid residues.

12. The method according to claim 1, wherein the substrate is selected from the group consisting of: bulk histones, synthetic peptides, and nucleosomes.

13. The method according to claim 8, wherein the methylated site is either mono-methylated, di-methylated or tri-methylated.

14. The method according to claim 1, wherein the compound and said polypeptide of the JMJD2 subfamily of Jumonji proteins are also incubated with Fe(II) ions, α-ketoglutarate and/or ascorbic acid.

15. The method according to claim 5, wherein step a) is done by immunoblotting or mass-spectrometry.

16. The method according to claim 1, said method comprising the steps of:
  i) preparing a suspension of a substrate for demethylation in a solution containing iron and alpha-ketoglutarate
  ii) adding said test compound to the suspension
  iii) adding to said suspension in ii) a polypeptide of the JMJD2 subfamily of Jumonji proteins
  iv) incubating said suspension and
  v) determining the extent of demethylation of said substrate.

17. The method according to claim 16, wherein the extent of demethylation is assayed using an immunological binding partner specific for histone H3 methylated at lysine 9.

18. The method according to claim 17, wherein said immunological binding partner is an anti trimethylated histone H3-K9 antibody.

19. The method according to claim 17, wherein said immunological binding partner is an anti dimethylated histone H3-K9 antibody.

20. The method according to claim 16, wherein the extent of demethylation is assayed using the release of formaldehyde.

21. The method according to claim 16, wherein the extent of demethylation is assayed using consumption of oxygen.

22. The method according to claim 16, wherein the extent of demethylation is assayed using the carboxylation state of an α-ketoglutarate substrate co-factor.

* * * * *

SEQUENCE LISTING

<160> NUMBER OF SEQ ID NOS: 64

<210> SEQ ID NO 1
<211> LENGTH: 1056
<212> TYPE: PRT

-continued

<213> ORGANISM: Homo sapiens

<400> SEQUENCE: 1

| | | | | | | | | | | | | | | |
|---|---|---|---|---|---|---|---|---|---|---|---|---|---|---|
| Met | Glu | Val | Ala | Glu | Val | Ser | Pro | Leu | Asn | Pro | Ser | Cys | Lys | Ile |
| 1 | | | | 5 | | | | | 10 | | | | | 15 |
| Met | Thr | Phe | Arg | Pro | Ser | Met | Glu | Glu | Phe | Arg | Glu | Phe | Asn | Lys | Tyr |
| | | | | 20 | | | | | 25 | | | | | 30 | |
| Leu | Ala | Tyr | Met | Glu | Ser | Lys | Gly | Ala | His | Arg | Ala | Gly | Leu | Ala | Lys |
| | | | 35 | | | | | 40 | | | | | 45 | | |
| Val | Ile | Pro | Pro | Lys | Glu | Trp | Lys | Pro | Arg | Gln | Cys | Tyr | Asp | Asp | Ile |
| | 50 | | | | | 55 | | | | | 60 | | | | |
| Asp | Asn | Leu | Leu | Ile | Pro | Ala | Pro | Ile | Gln | Gln | Met | Val | Thr | Gly | Gln |
| 65 | | | | | 70 | | | | | 75 | | | | | 80 |
| Ser | Gly | Leu | Phe | Thr | Gln | Tyr | Asn | Ile | Gln | Lys | Lys | Ala | Met | Thr | Val |
| | | | | 85 | | | | | 90 | | | | | 95 | |
| Lys | Glu | Phe | Arg | Gln | Leu | Ala | Asn | Ser | Gly | Lys | Tyr | Cys | Thr | Pro | Arg |
| | | | | 100 | | | | | 105 | | | | | 110 | |
| Tyr | Leu | Asp | Tyr | Glu | Asp | Leu | Glu | Arg | Lys | Tyr | Trp | Lys | Asn | Leu | Thr |
| | | | 115 | | | | | 120 | | | | | 125 | | |
| Phe | Val | Ala | Pro | Ile | Tyr | Gly | Ala | Asp | Ile | Asn | Gly | Ser | Ile | Tyr | Asp |
| | 130 | | | | | 135 | | | | | 140 | | | | |
| Glu | Gly | Val | Asp | Glu | Trp | Asn | Ile | Ala | Arg | Ile | Asn | Thr | Val | Leu | Asp |
| 145 | | | | | 150 | | | | | 155 | | | | | 160 |
| Val | Val | Glu | Glu | Glu | Cys | Gly | Ile | Ser | Ile | Glu | Gly | Val | Asn | Thr | Pro |
| | | | | 165 | | | | | 170 | | | | | 175 | |
| Tyr | Leu | Tyr | Phe | Gly | Met | Trp | Lys | Thr | Thr | Phe | Ala | Trp | His | Thr | Glu |
| | | | | 180 | | | | | 185 | | | | | 190 | |
| Asp | Met | Asp | Leu | Tyr | Ser | Ile | Asn | Tyr | Leu | His | Phe | Gly | Glu | Pro | Lys |
| | | | 195 | | | | | 200 | | | | | 205 | | |
| Ser | Trp | Tyr | Ala | Ile | Pro | Pro | Glu | His | Gly | Lys | Arg | Leu | Glu | Arg | Leu |
| | 210 | | | | | 215 | | | | | 220 | | | | |
| Ala | Gln | Gly | Phe | Phe | Pro | Ser | Ser | Gln | Gly | Cys | Asp | Ala | Phe | Leu |
| 225 | | | | | 230 | | | | | 235 | | | | | 240 |
| Arg | His | Lys | Met | Thr | Leu | Ile | Ser | Pro | Ser | Val | Leu | Lys | Lys | Tyr | Gly |
| | | | | 245 | | | | | 250 | | | | | 255 | |
| Ile | Pro | Phe | Asp | Lys | Ile | Thr | Gln | Glu | Ala | Gly | Glu | Phe | Met | Ile | Thr |
| | | | | 260 | | | | | 265 | | | | | 270 | |
| Phe | Pro | Tyr | Gly | Tyr | His | Ala | Gly | Phe | Asn | His | Gly | Phe | Asn | Cys | Ala |
| | | | 275 | | | | | 280 | | | | | 285 | | |
| Glu | Ser | Thr | Asn | Phe | Ala | Thr | Val | Arg | Trp | Ile | Asp | Tyr | Gly | Lys | Val |
| | 290 | | | | | 295 | | | | | 300 | | | | |
| Ala | Lys | Leu | Cys | Thr | Cys | Arg | Lys | Asp | Met | Val | Lys | Ile | Ser | Met | Asp |
| 305 | | | | | 310 | | | | | 315 | | | | | 320 |
| Ile | Phe | Val | Arg | Lys | Phe | Gln | Pro | Asp | Arg | Tyr | Gln | Leu | Trp | Lys | Gln |
| | | | | 325 | | | | | 330 | | | | | 335 | |
| Gly | Lys | Asp | Ile | Tyr | Thr | Ile | Asp | His | Thr | Lys | Pro | Thr | Pro | Ala | Ser |
| | | | 340 | | | | | 345 | | | | | 350 | | |
| Thr | Pro | Glu | Val | Lys | Ala | Trp | Leu | Gln | Arg | Arg | Arg | Lys | Val | Arg | Lys |
| | | | 355 | | | | | 360 | | | | | 365 | | |
| Ala | Ser | Arg | Ser | Phe | Gln | Cys | Ala | Arg | Ser | Thr | Ser | Lys | Arg | Pro | Lys |
| | | | 370 | | | | | 375 | | | | | 380 | | |
| Ala | Asp | Glu | Glu | Glu | Glu | Val | Ser | Asp | Glu | Val | Asp | Gly | Ala | Glu | Val |
| 385 | | | | | 390 | | | | | 395 | | | | | 400 |
| Pro | Asn | Pro | Asp | Ser | Val | Thr | Asp | Asp | Leu | Lys | Val | Ser | Glu | Lys | Ser |

-continued

```
            405                 410                 415
Glu Ala Ala Val Lys Leu Arg Asn Thr Glu Ala Ser Ser Glu Glu
                420                 425                 430

Ser Ser Ala Ser Arg Met Gln Val Glu Gln Asn Leu Ser Asp His Ile
            435                 440                 445

Lys Leu Ser Gly Asn Ser Cys Leu Ser Thr Ser Val Thr Glu Asp Ile
        450                 455                 460

Lys Thr Glu Asp Asp Lys Ala Tyr Ala Tyr Arg Ser Val Pro Ser Ile
465                 470                 475                 480

Ser Ser Glu Ala Asp Asp Ser Ile Pro Leu Ser Thr Gly Tyr Glu Lys
                485                 490                 495

Pro Glu Lys Ser Asp Pro Ser Glu Leu Ser Trp Pro Lys Ser Pro Glu
            500                 505                 510

Ser Cys Ser Ser Val Ala Glu Ser Asn Gly Val Leu Thr Glu Gly Glu
        515                 520                 525

Glu Ser Asp Val Glu Ser His Gly Asn Gly Leu Glu Pro Gly Glu Ile
        530                 535                 540

Pro Ala Val Pro Ser Gly Glu Arg Asn Ser Phe Lys Val Pro Ser Ile
545                 550                 555                 560

Ala Glu Gly Glu Asn Lys Thr Ser Lys Ser Trp Arg His Pro Leu Ser
                565                 570                 575

Arg Pro Pro Ala Arg Ser Pro Met Thr Leu Val Lys Gln Gln Ala Pro
            580                 585                 590

Ser Asp Glu Glu Leu Pro Glu Val Leu Ser Ile Glu Glu Val Glu
        595                 600                 605

Glu Thr Glu Ser Trp Ala Lys Pro Leu Ile His Leu Trp Gln Thr Lys
        610                 615                 620

Ser Pro Asn Phe Ala Ala Glu Gln Glu Tyr Asn Ala Thr Val Ala Arg
625                 630                 635                 640

Met Lys Pro His Cys Ala Ile Cys Thr Leu Leu Met Pro Tyr His Lys
                645                 650                 655

Pro Asp Ser Ser Asn Glu Glu Asn Asp Ala Arg Trp Glu Thr Lys Leu
            660                 665                 670

Asp Glu Val Val Thr Ser Glu Gly Lys Thr Lys Pro Leu Ile Pro Glu
        675                 680                 685

Met Cys Phe Ile Tyr Ser Glu Glu Asn Ile Glu Tyr Ser Pro Pro Asn
        690                 695                 700

Ala Phe Leu Glu Glu Asp Gly Thr Ser Leu Leu Ile Ser Cys Ala Lys
705                 710                 715                 720

Cys Cys Val Arg Val His Ala Ser Cys Tyr Gly Ile Pro Ser His Glu
                725                 730                 735

Ile Cys Asp Gly Trp Leu Cys Ala Arg Cys Lys Arg Asn Ala Trp Thr
            740                 745                 750

Ala Glu Cys Cys Leu Cys Asn Leu Arg Gly Gly Ala Leu Lys Gln Thr
        755                 760                 765

Lys Asn Asn Arg Trp Ala His Val Met Cys Ala Val Ala Val Pro Glu
        770                 775                 780

Val Arg Phe Thr Asn Val Pro Glu Arg Thr Gln Ile Asp Val Gly Arg
785                 790                 795                 800

Ile Pro Leu Gln Arg Leu Lys Leu Lys Cys Ile Phe Cys Arg His Arg
                805                 810                 815

Val Lys Arg Val Ser Gly Ala Cys Ile Gln Cys Ser Tyr Gly Arg Cys
            820                 825                 830
```

-continued

```
Pro Ala Ser Phe His Val Thr Cys Ala His Ala Ala Gly Val Leu Met
        835                 840                 845
Glu Pro Asp Asp Trp Pro Tyr Val Val Asn Ile Thr Cys Phe Arg His
    850                 855                 860
Lys Val Asn Pro Asn Val Lys Ser Lys Ala Cys Glu Lys Val Ile Ser
865                 870                 875                 880
Val Gly Gln Thr Val Ile Thr Lys His Arg Asn Thr Arg Tyr Tyr Ser
                885                 890                 895
Cys Arg Val Met Ala Val Thr Ser Gln Thr Phe Tyr Glu Val Met Phe
                900                 905                 910
Asp Asp Gly Ser Phe Ser Arg Asp Thr Phe Pro Glu Asp Ile Val Ser
            915                 920                 925
Arg Asp Cys Leu Lys Leu Gly Pro Ala Glu Gly Glu Val Val Gln
        930                 935                 940
Val Lys Trp Pro Asp Gly Lys Leu Tyr Gly Ala Lys Tyr Phe Gly Ser
945                 950                 955                 960
Asn Ile Ala His Met Tyr Gln Val Glu Phe Glu Asp Gly Ser Gln Ile
                965                 970                 975
Ala Met Lys Arg Glu Asp Ile Tyr Thr Leu Asp Glu Glu Leu Pro Lys
            980                 985                 990
Arg Val Lys Ala Arg Phe Ser Thr  Ala Ser Asp Met Arg  Phe Glu Asp
        995                 1000                1005
Thr Phe  Tyr Gly Ala Asp Ile  Ile Gln Gly Glu Arg  Lys Arg Gln
    1010                1015                1020
Arg Val  Leu Ser Ser Arg Phe  Lys Asn Glu Tyr Val  Ala Asp Pro
    1025                1030                1035
Val Tyr  Arg Thr Phe Leu Lys  Ser Ser Phe Gln Lys  Lys Cys Gln
    1040                1045                1050
Lys Arg  Gln
    1055

<210> SEQ ID NO 2
<211> LENGTH: 1064
<212> TYPE: PRT
<213> ORGANISM: Homo sapiens

<400> SEQUENCE: 2

Met Ala Ser Glu Ser Glu Thr Leu Asn Pro Ser Ala Arg Ile Met Thr
1               5                   10                  15
Phe Tyr Pro Thr Met Glu Glu Phe Arg Asn Phe Ser Arg Tyr Ile Ala
                20                  25                  30
Tyr Ile Glu Ser Gln Gly Ala His Arg Ala Gly Leu Ala Lys Val Val
            35                  40                  45
Pro Pro Lys Glu Trp Lys Pro Arg Ala Ser Tyr Asp Asp Ile Asp Asp
        50                  55                  60
Leu Val Ile Pro Ala Pro Ile Gln Gln Leu Val Thr Gly Gln Ser Gly
65                  70                  75                  80
Leu Phe Thr Gln Tyr Asn Ile Gln Lys Lys Ala Met Thr Val Arg Glu
                85                  90                  95
Phe Arg Lys Ile Ala Asn Ser Asp Lys Tyr Cys Thr Pro Arg Tyr Ser
                100                 105                 110
Glu Phe Glu Glu Leu Glu Arg Lys Tyr Trp Lys Asn Leu Thr Phe Asn
            115                 120                 125
Pro Pro Ile Tyr Gly Ala Asp Val Asn Gly Thr Leu Tyr Glu Lys His
        130                 135                 140
```

```
Val Asp Glu Trp Asn Ile Gly Arg Leu Arg Thr Ile Leu Asp Leu Val
145                 150                 155                 160

Glu Lys Glu Ser Gly Ile Thr Ile Glu Gly Val Asn Thr Pro Tyr Leu
            165                 170                 175

Tyr Phe Gly Met Trp Lys Thr Ser Phe Ala Trp His Thr Glu Asp Met
            180                 185                 190

Asp Leu Tyr Ser Ile Asn Tyr Leu His Phe Gly Glu Pro Lys Ser Trp
            195                 200                 205

Tyr Ser Val Pro Pro Glu His Gly Lys Arg Leu Glu Arg Leu Ala Lys
            210                 215                 220

Gly Phe Phe Pro Gly Ser Ala Gln Ser Cys Glu Ala Phe Leu Arg His
225                 230                 235                 240

Lys Met Thr Leu Ile Ser Pro Leu Met Leu Lys Lys Tyr Gly Ile Pro
            245                 250                 255

Phe Asp Lys Val Thr Gln Glu Ala Gly Glu Phe Met Ile Thr Phe Pro
            260                 265                 270

Tyr Gly Tyr His Ala Gly Phe Asn His Gly Phe Asn Cys Ala Glu Ser
            275                 280                 285

Thr Asn Phe Ala Thr Arg Arg Trp Ile Glu Tyr Gly Lys Gln Ala Val
            290                 295                 300

Leu Cys Ser Cys Arg Lys Asp Met Val Lys Ile Ser Met Asp Val Phe
305                 310                 315                 320

Val Arg Lys Phe Gln Pro Glu Arg Tyr Lys Leu Trp Lys Ala Gly Lys
            325                 330                 335

Asp Asn Thr Val Ile Asp His Thr Leu Pro Thr Pro Glu Ala Ala Glu
            340                 345                 350

Phe Leu Lys Glu Ser Glu Leu Pro Pro Arg Ala Gly Asn Glu Glu Glu
            355                 360                 365

Cys Pro Glu Glu Asp Met Glu Gly Val Glu Asp Gly Glu Glu Gly Asp
            370                 375                 380

Leu Lys Thr Ser Leu Ala Lys His Arg Ile Gly Thr Lys Arg His Arg
385                 390                 395                 400

Val Cys Leu Glu Ile Pro Gln Glu Val Ser Gln Ser Glu Leu Phe Pro
            405                 410                 415

Lys Glu Asp Leu Ser Ser Glu Gln Tyr Glu Met Thr Glu Cys Pro Ala
            420                 425                 430

Ala Leu Ala Pro Val Arg Pro Thr His Ser Ser Val Arg Gln Val Glu
            435                 440                 445

Asp Gly Leu Thr Phe Pro Asp Tyr Ser Asp Ser Thr Glu Val Lys Phe
            450                 455                 460

Glu Glu Leu Lys Asn Val Lys Leu Glu Glu Glu Asp Glu Glu Glu Glu
465                 470                 475                 480

Gln Glu Ala Ala Ala Leu Asp Leu Ser Val Asn Pro Ala Ser Val Gly
            485                 490                 495

Gly Arg Leu Val Phe Ser Gly Ser Lys Lys Ser Ser Ser Ser Leu
            500                 505                 510

Gly Ser Gly Ser Ser Arg Asp Ser Ile Ser Ser Asp Ser Glu Thr Ser
            515                 520                 525

Glu Pro Leu Ser Cys Arg Ala Gln Gly Gln Thr Gly Val Leu Thr Val
            530                 535                 540

His Ser Tyr Ala Lys Gly Asp Gly Arg Val Thr Val Gly Glu Pro Cys
545                 550                 555                 560

Thr Arg Lys Lys Gly Ser Ala Ala Arg Ser Phe Ser Glu Arg Glu Leu
            565                 570                 575
```

```
Ala Glu Val Ala Asp Glu Tyr Met Phe Ser Leu Glu Glu Asn Lys Lys
            580                 585                 590

Ser Lys Gly Arg Arg Gln Pro Leu Ser Lys Leu Pro Arg His His Pro
        595                 600                 605

Leu Val Leu Gln Glu Cys Val Ser Asp Glu Thr Ser Glu Gln Leu
        610                 615                 620

Thr Pro Glu Glu Ala Glu Thr Glu Ala Trp Ala Lys Pro Leu
625                 630                 635                 640

Ser Gln Leu Trp Gln Asn Arg Pro Pro Asn Phe Glu Ala Glu Lys Glu
                645                 650                 655

Phe Asn Glu Thr Met Ala Gln Gln Ala Pro His Cys Ala Val Cys Met
                660                 665                 670

Ile Phe Gln Thr Tyr His Gln Val Glu Phe Gly Gly Phe Asn Gln Asn
            675                 680                 685

Cys Gly Asn Ala Ser Asp Leu Ala Pro Gln Lys Gln Arg Thr Lys Pro
        690                 695                 700

Leu Ile Pro Glu Met Cys Phe Thr Ser Thr Gly Cys Ser Thr Asp Ile
705                 710                 715                 720

Asn Leu Ser Thr Pro Tyr Leu Glu Glu Asp Gly Thr Ser Ile Leu Val
                725                 730                 735

Ser Cys Lys Lys Cys Ser Val Arg Val His Ala Ser Cys Tyr Gly Val
            740                 745                 750

Pro Pro Ala Lys Ala Ser Glu Asp Trp Met Cys Ser Arg Cys Ser Ala
        755                 760                 765

Asn Ala Leu Glu Glu Asp Cys Cys Leu Cys Ser Leu Arg Gly Gly Ala
        770                 775                 780

Leu Gln Arg Ala Asn Asp Asp Arg Trp Val His Val Ser Cys Ala Val
785                 790                 795                 800

Ala Ile Leu Glu Ala Arg Phe Val Asn Ile Ala Glu Arg Ser Pro Val
                805                 810                 815

Asp Val Ser Lys Ile Pro Leu Pro Arg Phe Lys Leu Lys Cys Ile Phe
            820                 825                 830

Cys Lys Lys Arg Arg Lys Arg Thr Ala Gly Cys Cys Val Gln Cys Ser
835                 840                 845

His Gly Arg Cys Pro Thr Ala Phe His Val Ser Cys Ala Gln Ala Ala
        850                 855                 860

Gly Val Met Met Gln Pro Asp Asp Trp Pro Phe Val Val Phe Ile Thr
865                 870                 875                 880

Cys Phe Arg His Lys Ile Pro Asn Leu Glu Arg Ala Lys Gly Ala Leu
                885                 890                 895

Gln Ser Ile Thr Ala Gly Gln Lys Val Ile Ser Lys His Lys Asn Gly
            900                 905                 910

Arg Phe Tyr Gln Cys Glu Val Val Arg Leu Thr Thr Glu Thr Phe Tyr
        915                 920                 925

Glu Val Asn Phe Asp Asp Gly Ser Phe Ser Asp Asn Leu Tyr Pro Glu
        930                 935                 940

Asp Ile Val Ser Gln Asp Cys Leu Gln Phe Gly Pro Pro Ala Glu Gly
945                 950                 955                 960

Glu Val Val Gln Val Arg Trp Thr Asp Gly Gln Val Tyr Gly Ala Lys
                965                 970                 975

Phe Val Ala Ser His Pro Ile Gln Met Tyr Gln Val Glu Phe Glu Asp
            980                 985                 990

Gly Ser Gln Leu Val Val Lys Arg  Asp Asp Val Tyr Thr  Leu Asp Glu
```

-continued

```
                995                1000               1005
Glu Leu Pro Lys Arg Val Lys Ser Arg Leu Ser Val Ala Ser Asp
        1010                1015               1020

Met Arg Phe Asn Glu Ile Phe Thr Glu Lys Val Lys Gln Glu
        1025                1030               1035

Lys Lys Arg Gln Arg Val Ile Asn Ser Arg Tyr Arg Glu Asp Tyr
        1040                1045               1050

Ile Glu Pro Ala Leu Tyr Arg Ala Ile Met Glu
        1055                1060

<210> SEQ ID NO 3
<211> LENGTH: 1096
<212> TYPE: PRT
<213> ORGANISM: Homo sapiens

<400> SEQUENCE: 3

Met Gly Ser Glu Asp His Gly Ala Gln Asn Pro Ser Cys Lys Ile Met
1               5                   10                  15

Thr Phe Arg Pro Thr Met Glu Glu Phe Lys Asp Phe Asn Lys Tyr Val
            20                  25                  30

Ala Tyr Ile Glu Ser Gln Gly Ala His Arg Ala Gly Leu Ala Lys Ile
        35                  40                  45

Ile Pro Pro Lys Glu Trp Lys Pro Arg Gln Thr Tyr Asp Asp Ile Asp
    50                  55                  60

Asp Val Val Ile Pro Ala Pro Ile Gln Gln Val Val Thr Gly Gln Ser
65                  70                  75                  80

Gly Leu Phe Thr Gln Tyr Asn Ile Gln Lys Lys Ala Met Thr Val Gly
                85                  90                  95

Glu Tyr Arg Arg Leu Ala Asn Ser Glu Lys Tyr Cys Thr Pro Arg His
            100                 105                 110

Gln Asp Phe Asp Asp Leu Glu Arg Lys Tyr Trp Lys Asn Leu Thr Phe
        115                 120                 125

Val Ser Pro Ile Tyr Gly Ala Asp Ile Ser Gly Ser Leu Tyr Asp Asp
    130                 135                 140

Asp Val Ala Gln Trp Asn Ile Gly Ser Leu Arg Thr Ile Leu Asp Met
145                 150                 155                 160

Val Glu Arg Glu Cys Gly Thr Ile Ile Glu Gly Val Asn Thr Pro Tyr
                165                 170                 175

Leu Tyr Phe Gly Met Trp Lys Thr Thr Phe Ala Trp His Thr Glu Asp
            180                 185                 190

Met Asp Leu Tyr Ser Ile Asn Tyr Leu His Phe Gly Glu Pro Lys Ser
        195                 200                 205

Trp Tyr Ala Ile Pro Pro Glu His Gly Lys Arg Leu Glu Arg Leu Ala
    210                 215                 220

Ile Gly Phe Phe Pro Gly Ser Ser Gln Gly Cys Asp Ala Phe Leu Arg
225                 230                 235                 240

His Lys Met Thr Leu Ile Ser Pro Ile Ile Leu Lys Lys Tyr Gly Ile
                245                 250                 255

Pro Phe Ser Arg Ile Thr Gln Glu Ala Gly Glu Phe Met Ile Thr Phe
            260                 265                 270

Pro Tyr Gly Tyr His Ala Gly Phe Asn His Gly Phe Asn Cys Ala Glu
        275                 280                 285

Ser Thr Asn Phe Ala Thr Leu Arg Trp Ile Asp Tyr Gly Lys Val Ala
    290                 295                 300

Thr Gln Cys Thr Cys Arg Lys Asp Met Val Lys Ile Ser Met Asp Val
```

```
            305                 310                 315                 320
        Phe Val Arg Ile Leu Gln Pro Glu Arg Tyr Glu Leu Trp Lys Gln Gly
                        325                 330                 335

Lys Asp Leu Thr Val Leu Asp His Thr Arg Pro Thr Ala Leu Thr Ser
                    340                 345                 350

Pro Glu Leu Ser Ser Trp Ser Ala Ser Arg Ala Ser Leu Lys Ala Lys
                    355                 360                 365

Leu Leu Arg Arg Ser His Arg Lys Arg Ser Gln Pro Lys Lys Pro Lys
            370                 375                 380

Pro Glu Asp Pro Lys Phe Pro Gly Gly Thr Ala Gly Ala Ala Leu
        385                 390                 395                 400

Leu Glu Glu Ala Gly Gly Ser Val Lys Glu Ala Gly Pro Glu Val
                        405                 410                 415

Asp Pro Glu Glu Glu Glu Glu Pro Gln Pro Leu Pro His Gly Arg
                        420                 425                 430

Glu Ala Glu Gly Ala Glu Asp Gly Arg Gly Lys Leu Arg Pro Thr
                        435                 440                 445

Lys Ala Lys Ser Glu Arg Lys Lys Ser Phe Gly Leu Leu Pro Pro
                    450                 455                 460

Gln Leu Pro Pro Pro Ala His Phe Pro Ser Glu Ala Leu Trp
        465                 470                 475                 480

Leu Pro Ser Pro Leu Glu Pro Pro Val Leu Gly Pro Gly Pro Ala Ala
                        485                 490                 495

Met Glu Glu Ser Pro Leu Pro Ala Pro Leu Asn Val Val Pro Pro Glu
                    500                 505                 510

Val Pro Ser Glu Glu Leu Glu Ala Lys Pro Arg Pro Ile Ile Pro Met
                515                 520                 525

Leu Tyr Val Val Pro Arg Pro Gly Lys Ala Ala Phe Asn Gln Glu His
            530                 535                 540

Val Ser Cys Gln Gln Ala Phe Glu His Phe Ala Gln Lys Gly Pro Thr
        545                 550                 555                 560

Trp Lys Glu Pro Val Ser Pro Met Glu Leu Thr Gly Pro Glu Asp Gly
                        565                 570                 575

Ala Ala Ser Ser Gly Ala Gly Arg Met Glu Thr Lys Ala Arg Ala Gly
                    580                 585                 590

Glu Gly Gln Ala Pro Ser Thr Phe Ser Lys Leu Lys Met Glu Ile Lys
                    595                 600                 605

Lys Ser Arg Arg His Pro Leu Gly Arg Pro Pro Thr Arg Ser Pro Leu
                610                 615                 620

Ser Val Val Lys Gln Glu Ala Ser Ser Asp Glu Glu Ala Ser Pro Phe
        625                 630                 635                 640

Ser Gly Glu Glu Asp Val Ser Asp Pro Asp Ala Leu Arg Pro Leu Leu
                        645                 650                 655

Ser Leu Gln Trp Lys Asn Arg Ala Ala Ser Phe Gln Ala Glu Arg Lys
                    660                 665                 670

Phe Asn Ala Ala Ala Arg Thr Glu Pro Tyr Cys Ala Ile Cys Thr
                    675                 680                 685

Leu Phe Tyr Pro Tyr Cys Gln Ala Leu Gln Thr Glu Lys Glu Ala Pro
            690                 695                 700

Ile Ala Ser Leu Gly Glu Gly Cys Pro Ala Thr Leu Pro Ser Lys Ser
        705                 710                 715                 720

Arg Gln Lys Thr Arg Pro Leu Ile Pro Glu Met Cys Phe Thr Ser Gly
                        725                 730                 735
```

-continued

Gly Glu Asn Thr Glu Pro Leu Pro Ala Asn Ser Tyr Ile Gly Asp Asp
            740                 745                 750

Gly Thr Ser Pro Leu Ile Ala Cys Gly Lys Cys Cys Leu Gln Val His
        755                 760                 765

Ala Ser Cys Tyr Gly Ile Arg Pro Glu Leu Val Asn Glu Gly Trp Thr
    770                 775                 780

Cys Ser Arg Cys Ala Ala His Ala Trp Thr Ala Glu Cys Cys Leu Cys
785                 790                 795                 800

Asn Leu Arg Gly Gly Ala Leu Gln Met Thr Thr Asp Arg Arg Trp Ile
                805                 810                 815

His Val Ile Cys Ala Ile Ala Val Pro Glu Ala Arg Phe Leu Asn Val
            820                 825                 830

Ile Glu Arg His Pro Val Asp Ile Ser Ala Ile Pro Glu Gln Arg Trp
        835                 840                 845

Lys Leu Lys Cys Val Tyr Cys Arg Lys Arg Met Lys Lys Val Ser Gly
    850                 855                 860

Ala Cys Ile Gln Cys Ser Tyr Glu His Cys Ser Thr Ser Phe His Val
865                 870                 875                 880

Thr Cys Ala His Ala Ala Gly Val Leu Met Glu Pro Asp Asp Trp Pro
                885                 890                 895

Tyr Val Val Ser Ile Thr Cys Leu Lys His Lys Ser Gly His Ala
            900                 905                 910

Val Gln Leu Leu Arg Ala Val Ser Leu Gly Gln Val Ile Thr Lys
        915                 920                 925

Asn Arg Asn Gly Leu Tyr Tyr Arg Cys Arg Val Ile Gly Ala Ala Ser
    930                 935                 940

Gln Thr Cys Tyr Glu Val Asn Phe Asp Asp Gly Ser Tyr Ser Asp Asn
945                 950                 955                 960

Leu Tyr Pro Glu Ser Ile Thr Ser Arg Asp Cys Val Gln Leu Gly Pro
                965                 970                 975

Pro Ser Glu Gly Glu Leu Val Glu Leu Arg Trp Thr Asp Gly Asn Leu
            980                 985                 990

Tyr Lys Ala Lys Phe Ile Ser Ser Val Thr Ser His Ile Tyr Gln Val
            995                 1000                1005

Glu Phe Glu Asp Gly Ser Gln Leu Thr Val Lys Arg Gly Asp Ile
        1010                1015                1020

Phe Thr Leu Glu Glu Glu Leu Pro Lys Arg Val Arg Ser Arg Leu
        1025                1030                1035

Ser Leu Ser Thr Gly Ala Pro Gln Glu Pro Ala Phe Ser Gly Glu
        1040                1045                1050

Glu Ala Lys Ala Ala Lys Arg Pro Arg Val Gly Thr Pro Leu Ala
        1055                1060                1065

Thr Glu Asp Ser Gly Arg Ser Gln Asp Tyr Val Ala Phe Val Glu
        1070                1075                1080

Ser Leu Leu Gln Val Gln Gly Arg Pro Gly Ala Pro Phe
        1085                1090                1095

<210> SEQ ID NO 4
<211> LENGTH: 43
<212> TYPE: PRT
<213> ORGANISM: Homo sapiens

<400> SEQUENCE: 4

Arg Ile Met Thr Phe Tyr Pro Thr Met Glu Glu Phe Arg Asn Phe Ser
1               5                   10                  15

Arg Tyr Ile Ala Tyr Ile Glu Ser Gln Gly Ala His Arg Ala Gly Leu
             20                  25                  30

Ala Lys Val Val Pro Pro Lys Glu Trp Lys Pro
             35                  40

<210> SEQ ID NO 5
<211> LENGTH: 167
<212> TYPE: PRT
<213> ORGANISM: Homo sapiens

<400> SEQUENCE: 5

Glu Lys His Val Asp Glu Trp Asn Ile Gly Arg Leu Arg Thr Ile Leu
1               5                   10                  15

Asp Leu Val Glu Lys Glu Ser Gly Ile Thr Ile Glu Gly Val Asn Thr
             20                  25                  30

Pro Tyr Leu Tyr Phe Gly Met Trp Lys Thr Ser Phe Ala Trp His Thr
         35                  40                  45

Glu Asp Met Asp Leu Tyr Ser Ile Asn Tyr Leu His Phe Gly Glu Pro
     50                  55                  60

Lys Ser Trp Tyr Ser Val Pro Pro Glu His Gly Lys Arg Leu Glu Arg
65                  70                  75                  80

Leu Ala Lys Gly Phe Phe Pro Gly Ser Ala Gln Ser Cys Glu Ala Phe
                 85                  90                  95

Leu Arg His Lys Met Thr Leu Ile Ser Pro Leu Met Leu Lys Lys Tyr
            100                 105                 110

Gly Ile Pro Phe Asp Lys Val Thr Gln Glu Ala Gly Glu Phe Met Ile
        115                 120                 125

Thr Phe Pro Tyr Gly Tyr His Ala Gly Phe Asn His Gly Phe Asn Cys
    130                 135                 140

Ala Glu Ser Thr Asn Phe Ala Thr Arg Arg Trp Ile Glu Tyr Gly Lys
145                 150                 155                 160

Gln Ala Val Leu Cys Ser Cys
                165

<210> SEQ ID NO 6
<211> LENGTH: 59
<212> TYPE: PRT
<213> ORGANISM: Homo sapiens

<400> SEQUENCE: 6

Met Cys Phe Thr Ser Thr Gly Cys Ser Thr Asp Ile Asn Leu Ser Thr
1               5                   10                  15

Pro Tyr Leu Glu Glu Asp Gly Thr Ser Ile Leu Val Ser Cys Lys Lys
             20                  25                  30

Cys Ser Val Arg Val His Ala Ser Cys Tyr Gly Val Pro Pro Ala Lys
         35                  40                  45

Ala Ser Glu Asp Trp Met Cys Ser Arg Cys Ser
     50                  55

<210> SEQ ID NO 7
<211> LENGTH: 57
<212> TYPE: PRT
<213> ORGANISM: Homo sapiens

<400> SEQUENCE: 7

Lys Cys Ile Phe Cys Lys Lys Arg Lys Arg Thr Ala Gly Cys Cys
1               5                   10                  15

Val Gln Cys Ser His Gly Arg Cys Pro Thr Ala Phe His Val Ser Cys
             20                  25                  30

```
Ala Gln Ala Ala Gly Val Met Met Gln Pro Asp Asp Trp Pro Phe Val
            35                  40                  45

Val Phe Ile Thr Cys Phe Arg His Lys
 50                  55
```

<210> SEQ ID NO 8
<211> LENGTH: 58
<212> TYPE: PRT
<213> ORGANISM: Homo sapiens

<400> SEQUENCE: 8

```
Gln Ser Ile Thr Ala Gly Gln Lys Val Ile Ser Lys His Lys Asn Gly
 1               5                  10                  15

Arg Phe Tyr Gln Cys Glu Val Val Arg Leu Thr Thr Glu Thr Phe Tyr
            20                  25                  30

Glu Val Asn Phe Asp Asp Gly Ser Phe Ser Asp Asn Leu Tyr Pro Glu
            35                  40                  45

Asp Ile Val Ser Gln Asp Cys Leu Gln Phe
 50                  55
```

<210> SEQ ID NO 9
<211> LENGTH: 57
<212> TYPE: PRT
<213> ORGANISM: Homo sapiens

<400> SEQUENCE: 9

```
Gly Pro Pro Ala Glu Gly Glu Val Val Gln Val Arg Trp Thr Asp Gly
 1               5                  10                  15

Gln Val Tyr Gly Ala Lys Phe Val Ala Ser His Pro Ile Gln Met Tyr
            20                  25                  30

Gln Val Glu Phe Glu Asp Gly Ser Gln Leu Val Val Lys Arg Asp Asp
            35                  40                  45

Val Tyr Thr Leu Asp Glu Glu Leu Pro
 50                  55
```

<210> SEQ ID NO 10
<211> LENGTH: 43
<212> TYPE: PRT
<213> ORGANISM: Homo sapiens

<400> SEQUENCE: 10

```
Lys Ile Met Thr Phe Arg Pro Thr Met Glu Glu Phe Lys Asp Phe Asn
 1               5                  10                  15

Lys Tyr Val Ala Tyr Ile Glu Ser Gln Gly Ala His Arg Ala Gly Leu
            20                  25                  30

Ala Lys Ile Ile Pro Pro Lys Glu Trp Lys Pro
            35                  40
```

<210> SEQ ID NO 11
<211> LENGTH: 167
<212> TYPE: PRT
<213> ORGANISM: Homo sapiens

<400> SEQUENCE: 11

```
Asp Asp Asp Val Ala Gln Trp Asn Ile Gly Ser Leu Arg Thr Ile Leu
 1               5                  10                  15

Asp Met Val Glu Arg Glu Cys Gly Thr Ile Glu Gly Val Asn Thr
            20                  25                  30

Pro Tyr Leu Tyr Phe Gly Met Trp Lys Thr Thr Phe Ala Trp His Thr
            35                  40                  45
```

```
Glu Asp Met Asp Leu Tyr Ser Ile Asn Tyr Leu His Phe Gly Glu Pro
            50                  55                  60

Lys Ser Trp Tyr Ala Ile Pro Pro Glu His Gly Lys Arg Leu Glu Arg
 65                  70                  75                  80

Leu Ala Ile Gly Phe Phe Pro Gly Ser Ser Gln Gly Cys Asp Ala Phe
                 85                  90                  95

Leu Arg His Lys Met Thr Leu Ile Ser Pro Ile Ile Leu Lys Lys Tyr
                100                 105                 110

Gly Ile Pro Phe Ser Arg Ile Thr Gln Glu Ala Gly Glu Phe Met Ile
            115                 120                 125

Thr Phe Pro Tyr Gly Tyr His Ala Gly Phe Asn His Gly Phe Asn Cys
130                 135                 140

Ala Glu Ser Thr Asn Phe Ala Thr Leu Arg Trp Ile Asp Tyr Gly Lys
145                 150                 155                 160

Val Ala Thr Gln Cys Thr Cys
                165
```

<210> SEQ ID NO 12
<211> LENGTH: 59
<212> TYPE: PRT
<213> ORGANISM: Homo sapiens

<400> SEQUENCE: 12

```
Met Cys Phe Thr Ser Gly Gly Glu Asn Thr Glu Pro Leu Pro Ala Asn
  1               5                  10                  15

Ser Tyr Ile Gly Asp Asp Gly Thr Ser Pro Leu Ile Ala Cys Gly Lys
                 20                  25                  30

Cys Cys Leu Gln Val His Ala Ser Cys Tyr Gly Ile Arg Pro Glu Leu
                 35                  40                  45

Val Asn Glu Gly Trp Thr Cys Ser Arg Cys Ala
                 50                  55
```

<210> SEQ ID NO 13
<211> LENGTH: 57
<212> TYPE: PRT
<213> ORGANISM: Homo sapiens

<400> SEQUENCE: 13

```
Lys Cys Val Tyr Cys Arg Lys Arg Met Lys Lys Val Ser Gly Ala Cys
  1               5                  10                  15

Ile Gln Cys Ser Tyr Glu His Cys Ser Thr Ser Phe His Val Thr Cys
                 20                  25                  30

Ala His Ala Ala Gly Val Leu Met Glu Pro Asp Asp Trp Pro Tyr Val
                 35                  40                  45

Val Ser Ile Thr Cys Leu Lys His Lys
                 50                  55
```

<210> SEQ ID NO 14
<211> LENGTH: 58
<212> TYPE: PRT
<213> ORGANISM: Homo sapiens

<400> SEQUENCE: 14

```
Arg Ala Val Ser Leu Gly Gln Val Val Ile Thr Lys Asn Arg Asn Gly
  1               5                  10                  15

Leu Tyr Tyr Arg Cys Arg Val Ile Gly Ala Ala Ser Gln Thr Cys Tyr
                 20                  25                  30

Glu Val Asn Phe Asp Asp Gly Ser Tyr Ser Asp Asn Leu Tyr Pro Glu
```

```
                        35                  40                  45

Ser Ile Thr Ser Arg Asp Cys Val Gln Leu
    50                  55

<210> SEQ ID NO 15
<211> LENGTH: 57
<212> TYPE: PRT
<213> ORGANISM: Homo sapiens

<400> SEQUENCE: 15

Gly Pro Pro Ser Glu Gly Glu Leu Val Glu Leu Arg Trp Thr Asp Gly
1               5                   10                  15

Asn Leu Tyr Lys Ala Lys Phe Ile Ser Ser Val Thr Ser His Ile Tyr
            20                  25                  30

Gln Val Glu Phe Glu Asp Gly Ser Gln Leu Thr Val Lys Arg Gly Asp
        35                  40                  45

Ile Phe Thr Leu Glu Glu Glu Leu Pro
    50                  55

<210> SEQ ID NO 16
<211> LENGTH: 43
<212> TYPE: PRT
<213> ORGANISM: Homo sapiens

<400> SEQUENCE: 16

Lys Ile Met Thr Phe Arg Pro Ser Met Glu Glu Phe Arg Glu Phe Asn
1               5                   10                  15

Lys Tyr Leu Ala Tyr Met Glu Ser Lys Gly Ala His Arg Ala Gly Leu
            20                  25                  30

Ala Lys Val Ile Pro Pro Lys Glu Trp Lys Pro
        35                  40

<210> SEQ ID NO 17
<211> LENGTH: 167
<212> TYPE: PRT
<213> ORGANISM: Homo sapiens

<400> SEQUENCE: 17

Asp Glu Gly Val Asp Glu Trp Asn Ile Ala Arg Ile Asn Thr Val Leu
1               5                   10                  15

Asp Val Val Glu Glu Cys Gly Ile Ser Ile Glu Gly Val Asn Thr
            20                  25                  30

Pro Tyr Leu Tyr Phe Gly Met Trp Lys Thr Thr Phe Ala Trp His Thr
        35                  40                  45

Glu Asp Met Asp Leu Tyr Ser Ile Asn Tyr Leu His Phe Gly Glu Pro
    50                  55                  60

Lys Ser Trp Tyr Ala Ile Pro Pro Glu His Gly Lys Arg Leu Glu Arg
65                  70                  75                  80

Leu Ala Gln Gly Phe Phe Pro Ser Ser Ser Gln Gly Cys Asp Ala Phe
                85                  90                  95

Leu Arg His Lys Met Thr Leu Ile Ser Pro Ser Val Leu Lys Lys Tyr
            100                 105                 110

Gly Ile Pro Phe Asp Lys Ile Thr Gln Glu Ala Gly Glu Phe Met Ile
        115                 120                 125

Thr Phe Pro Tyr Gly Tyr His Ala Gly Phe Asn His Gly Phe Asn Cys
    130                 135                 140

Ala Glu Ser Thr Asn Phe Ala Thr Val Arg Trp Ile Asp Tyr Gly Lys
145                 150                 155                 160
```

```
Val Ala Lys Leu Cys Thr Cys
              165

<210> SEQ ID NO 18
<211> LENGTH: 59
<212> TYPE: PRT
<213> ORGANISM: Homo sapiens

<400> SEQUENCE: 18

Met Cys Phe Ile Tyr Ser Glu Glu Asn Ile Glu Tyr Ser Pro Pro Asn
1               5                   10                  15

Ala Phe Leu Glu Glu Asp Gly Thr Ser Leu Leu Ile Ser Cys Ala Lys
            20                  25                  30

Cys Cys Val Arg Val His Ala Ser Cys Tyr Gly Ile Pro Ser His Glu
        35                  40                  45

Ile Cys Asp Gly Trp Leu Cys Ala Arg Cys Lys
        50                  55

<210> SEQ ID NO 19
<211> LENGTH: 57
<212> TYPE: PRT
<213> ORGANISM: Homo sapiens

<400> SEQUENCE: 19

Lys Cys Ile Phe Cys Arg His Arg Val Lys Arg Val Ser Gly Ala Cys
1               5                   10                  15

Ile Gln Cys Ser Tyr Gly Arg Cys Pro Ala Ser Phe His Val Thr Cys
            20                  25                  30

Ala His Ala Ala Gly Val Leu Met Glu Pro Asp Asp Trp Pro Tyr Val
        35                  40                  45

Val Asn Ile Thr Cys Phe Arg His Lys
        50                  55

<210> SEQ ID NO 20
<211> LENGTH: 58
<212> TYPE: PRT
<213> ORGANISM: Homo sapiens

<400> SEQUENCE: 20

Lys Val Ile Ser Val Gly Gln Thr Val Ile Thr Lys His Arg Asn Thr
1               5                   10                  15

Arg Tyr Tyr Ser Cys Arg Val Met Ala Val Thr Ser Gln Thr Phe Tyr
            20                  25                  30

Glu Val Met Phe Asp Asp Gly Ser Phe Ser Arg Asp Thr Phe Pro Glu
        35                  40                  45

Asp Ile Val Ser Arg Asp Cys Leu Lys Leu
        50                  55

<210> SEQ ID NO 21
<211> LENGTH: 57
<212> TYPE: PRT
<213> ORGANISM: Homo sapiens

<400> SEQUENCE: 21

Gly Pro Pro Ala Glu Gly Glu Val Val Gln Val Lys Trp Pro Asp Gly
1               5                   10                  15

Lys Leu Tyr Gly Ala Lys Tyr Phe Gly Ser Asn Ile Ala His Met Tyr
            20                  25                  30

Gln Val Glu Phe Glu Asp Gly Ser Gln Ile Ala Met Lys Arg Glu Asp
        35                  40                  45
```

Ile Tyr Thr Leu Asp Glu Glu Leu Pro
            50                  55

<210> SEQ ID NO 22
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Lys(me)

<400> SEQUENCE: 22

Thr Ala Arg Lys Ser Thr Gly
1               5

<210> SEQ ID NO 23
<211> LENGTH: 136
<212> TYPE: PRT
<213> ORGANISM: Homo sapiens

<400> SEQUENCE: 23

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 24
<211> LENGTH: 40
<212> TYPE: PRT
<213> ORGANISM: Homo sapiens

<400> SEQUENCE: 24

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg
        35                  40

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 4239
<212> TYPE: DNA
<213> ORGANISM: Homo sapiens

<400> SEQUENCE: 26

| | | | | | |
|---|---|---|---|---|---|
| aattcggcac | gagaacagct | gtcacctagt | gcggaacaag | tctcccaaat | ttcccaaatc | 60 |
| tccctgggcc | ggaggccact | gtcttctctt | cctcctccac | cgagtcgtgc | tctcgcccca | 120 |
| acccgcgcgc | cagacactgc | cctaaccatc | atggaggtgg | ccgaggtgga | aagtcctctg | 180 |
| aaccccagct | gtaagataat | gaccttcaga | ccctccatgg | aggagttccg | ggagttcaac | 240 |
| aaataccttg | catacatgga | gtctaaagga | gcccatcgtg | cgggtcttgc | aaaggtgatt | 300 |
| cctcctaagg | agtggaagcc | aagacagtgc | tatgatgaca | ttgataattt | gctcattcca | 360 |
| gcaccaattc | agcagatggt | cacagggcag | tcaggactgt | tcactcagta | caacatccag | 420 |
| aaaaaagcga | tgactgtgaa | ggagttcagg | cagctggcca | acagtggcaa | atattgtact | 480 |
| ccaagatact | tggattacga | agatttggag | cgcaagtact | ggaagaactt | aacttttgtg | 540 |
| gcacctatct | atggtgcaga | tattaatggg | agcatatatg | atgagggtgt | ggatgaatgg | 600 |
| aacatagctc | gcatcaatac | agtcttggat | gtggttgaag | aagagtgtgg | catttctatt | 660 |
| gagggtgtaa | ataccccata | tctctatttt | ggcatgtgga | agaccacgtt | tgcatggcac | 720 |
| accgaagaca | tggacctcta | tagcattaat | tatctccact | ttggagagcc | caagtcttgg | 780 |
| tatgctatac | ctccggagca | tggaaaacga | cttgaaagac | tagctcaagg | ttttttccca | 840 |
| agcagctccc | aagggtgtga | tgcatttctt | cgccacaaga | tgacattgat | ttctccatca | 900 |
| gtattgaaga | aatatggtat | cccctttgac | aagataaccc | aggaggctgg | agaattcatg | 960 |
| atcactttcc | catatggcta | ccatgctggt | tttaatcatg | gtttcaactg | tgcagaatct | 1020 |
| acaaattttg | ctactgtcag | atggattgac | tatggaaaag | ttgccaaatt | gtgcacttgc | 1080 |
| aggaaagaca | tggtgaagat | ttcaatggat | atctttgtga | ggaaatttca | gccagacaga | 1140 |
| tatcagcttt | ggaaacaagg | aaaggatata | taccattg | atcacacgaa | gcctactcca | 1200 |
| gcatccaccc | ctgaagtaaa | agcatggctg | cagaggagga | ggaaagtaag | aaaagcatcc | 1260 |
| cgaagcttcc | agtgtgctag | gtctacctct | aaaaggccta | aggctgatga | ggaagaggaa | 1320 |
| gtgtcagatg | aagtcgatgg | ggcagaggtc | cctaaccccg | actcagtcac | agatgacctc | 1380 |
| aaggtcagtg | aaaagtcaga | agcagcagtg | aagctgagga | acacagaagc | atcttcagaa | 1440 |
| gaaagagtcat | ctgctagcag | gatgcaggtg | gagcagaatt | tatcagatca | tatcaaactc | 1500 |
| tcaggaaaca | gctgcttaag | tacatctgta | acagaagaca | taaaaactga | ggatgacaaa | 1560 |
| gcttatgcat | atagaagtgt | accttctata | tccagtgagg | ctgatgattc | cattccattg | 1620 |
| tctactggct | atgagaagcc | cgagaaatca | gacccatccg | agctttcatg | gccaaagtca | 1680 |
| cctgagtcat | gctcatcagt | ggcagagagt | aatggtgtgt | taacagaggg | agaagagagt | 1740 |
| gatgtggaga | gccatgggaa | tggccttgaa | cctgggaaa | tcccagcggt | ccccagtgga | 1800 |
| gagagaaata | gcttcaaagt | ccccagtata | gcagagggag | agaacaaaac | ctctaagagt | 1860 |
| tggcgccatc | cacttagcag | gcctccagca | agatctccga | tgactcttgt | gaagcagcag | 1920 |
| gcgccaagtg | atgaagaatt | gcctgaggtt | ctgtccattg | aggaggaagt | ggaagaaaca | 1980 |
| gagtcttggg | cgaaacctct | catccacctt | tggcagacga | agtcccctaa | cttcgcagct | 2040 |

```
gagcaagagt ataatgcaac agtggccagg atgaagccac actgtgccat ctgcactctg    2100
ctcatgccgt accacaagcc agatagcagc aatgaagaaa atgatgctag atgggagaca    2160
aaattagatg aagtcgttac atcggaggga aagactaagc ccctcatacc agagatgtgt    2220
tttatttata gtgaagaaaa tatagaatat tctccaccca atgccttcct tgaagaggat    2280
ggaacaagtc tccttatttc ctgtgcaaag tgctgcgtac gggttcatgc aagttgttat    2340
ggtattcctt ctcatgagat ctgtgatgga tggctgtgtg cccggtgcaa agaaatgcg     2400
tggacagcag aatgctgtct ctgcaatttg agaggaggtg ctcttaagca acgaagaac     2460
aataggtggg cccatgtcat gtgcgccgtt gcggtcccag aagttcgatt cactaatgtc    2520
ccagaaagga cacaaataga tgtaggcaga ataccttac agaggttaaa attgaaatgc     2580
atcttctgca gacaccgggt taagagggtc tctggagcct gcatccagtg ttcctacggt    2640
cgctgcccgg cctccttcca tgtcacttgt gcccatgctg ctggggtact gatggagcct    2700
gatgattggc cttatgtggt gaacattaca tgctttcgac ataaggtcaa ccccaacgtg    2760
aagtccaagg cttgcgagaa ggtcatttcc gtgggtcaaa cggtcatcac gaagcatcgg    2820
aacacccggt attacagttg cagagtgatg gctgtgacat cgcagacctt ctatgaggtc    2880
atgtttgatg atggctcctt tagcagagac acatttcctg aggatatcgt gagccgagac    2940
tgtctgaagc tgggcccacc tgctgaggga gaagtcgtcc aagtcaagtg gcccgatggc    3000
aaactctatg gagcaaaata ttttggatca atattgccc acatgtacca ggttgagttt     3060
gaagatggat cccagatagc aatgaagaga aggacatct acactttaga tgaagagtta     3120
cccaagagag tgaaagctcg attttccaca gcctctgaca tgcgatttga agacacgttt    3180
tatggagcag acattatcca aggggagaga aagagacaaa gagtgctgag ctccaggttt    3240
aagaatgaat atgtggccga ccctgtatac cgcactttt tgaagagctc tttccagaag    3300
aagtgccaga agagacagta gtctgcatac atcgctgcag ccacagagc agcttgggtt    3360
ggaaagagaa agatgaaggg acatccttgg ggctgtgccg tgagatttgc tggcataggt    3420
gacagggtgt gtctctgaca gtggtaaatc gggtttccag agtttggtca ccaaaaatac    3480
aaaatacaca caatgaattg gacgcagcaa tctgaaatca tctctagtct tgctttcact    3540
tgtgagcagt tgtcttctat gatcccaaag aagttttcta agtgaaagga aatactagtg    3600
aatcacccac aaggaaaagc cactgccaca gaggaggcgg gtcccctggt gcggcttagg    3660
gccctgtcag gaaacacacg gggacctctc tctctagctc cagcaggtgg cacctcggta    3720
cccagcgggt agggcgataa tttatatatt ttccacagtc agggaaggac tctcacttat    3780
ttgtttcaaa ttgcagtttt tataaaacat ttttaaaaca caaatggcat gtatgctaat    3840
gagatttacc cgtgtgctat ctgtatttcc cttgtacaga acttttacat ttttgaatat    3900
tcctattact tttgattgtg tctgatggga actgagttgt tggcctttgt gaaatgaaat    3960
ttttggctct tgagaaagaa ttcttatgaa ttgttatgcg aattttatat atttaaagag    4020
ggagatctgg ggctgttatt tttaaacact ttttttcata atacatattc cgagtagata    4080
tttataaaat atatgtttct ttcattatgt gtttgtaaaa ttagagttta aataaatatg    4140
ctttgatgca tagttttgaa ctaatgtaac atgattttc ttttttaaaa cagcctgaaa     4200
atgtactagt gtttaaaaat aaagatttcc attttctcc                           4239
```

<210> SEQ ID NO 27
<211> LENGTH: 4417
<212> TYPE: DNA
<213> ORGANISM: Homo sapiens

<400> SEQUENCE: 27

```
gccttcgcct gctggaaaag cagtaggatc ggccagtggc gacagcagga gctgagccta        60
agccctggcg gggctttggg ctgtagattc ctgtctgact aaagggacct caaaaaggag       120
ggaaaatggc ttctgagtct gaaactctga atcccagtgc taggataatg accttttatc       180
caactatgga agagttccga aacttcagta gatacattgc ctacattgaa tcccaaggag       240
ctcatcgggc agggctagcc aaggttgttc ctccaaaaga gtggaagcca cgagcatcct       300
atgatgacat tgatgatttg gtcattcctg cccccattca acagctggtg acggggcagt       360
ctggcctctt tactcagtac aacatacaga gaaaagccat gactgttcga gagttccgca       420
agatagccaa tagcgataag tactgtaccc cacgctatag tgagtttgaa gagctcgagc       480
ggaaatactg gaaaaatctt acattcaatc ctccaatcta tggtgcagat gtgaatggta       540
ccctctatga aaagcatgtt gatgagtgga atattggccg gctgagaaca atcctggact       600
tggtggaaaa ggagagtggg atcaccattg agggtgtgaa cacccatac ctgtactttg       660
gcatgtggaa gacatccttt gcttggcaca ctgaagacat ggacctctac agcatcaact       720
acctgcactt tggagaacca aagtcctggt actctgttcc acctgagcat ggaaagcggt       780
tggaacgcct cgccaaaggc ttttcccag gaagtgctca aagctgtgag gcatttctcc       840
gccacaagat gaccctgatt tccccgttaa tgctgaagaa atatggaatt ccctttgaca       900
aggtgactca agaggctgga gagtttatga tcactttccc ttatggttac catgccggct       960
ttaaccatgg ttttaactgt gcggagtcta ccaattttgc tacccgtcgg tggattgagt      1020
acggcaagca agctgtgctg tgctcctgta gaaaggacat ggtgaagatc tccatggatg      1080
tgtttgtgag aaagttccag ccagaaaggt acaaactttg gaaagctggg aaggacaaca      1140
cagttattga ccatactctg cccacgccag aagcagctga gtttcttaag gagagtgaac      1200
tgcctccaag agctggcaac gaggaggagt gcccagagga ggacatggaa ggggtggagg      1260
atggagagga aggagacctg aagacaagcc tggccaagca ccgaataggg acaaagaggc      1320
accgagtttg tcttgaaata ccacaggagg tgagtcagag tgagctcttc cccaaggagg      1380
atctgagttc tgagcagtat gagatgacgg agtgcccggc agccctcgcc cctgtgaggc      1440
ccacccatag ctctgtgcgg caagttgagg atggtcttac cttcccagat tattctgact      1500
ccactgaagt caaatttgaa gagcttaaaa atgtcaaact agaagaggag gatgaggagg      1560
aagaacaaga agcagctgcc ttggatcttt ctgtgaatcc tgcgtctgta gggggacgcc      1620
ttgtcttctc aggctccaaa aagaaatcat cttctagcct gggctctggc tcttcacggg      1680
attctatctc ttctgattca gaaactagtg agcctctctc ctgccgagcc aagggcaaa       1740
cgggagttct cactgtgcac agttatgcca aaggggatgg cagggtcact gtgggagagc      1800
catgcacgag gaagaaagga agcgccgcta gaagtttcag tgagcgggag ctggcagagg      1860
ttgcagatga atacatgttt tccctagaag agaataagaa gtccaaggga cgccgtcagc      1920
ctttaagcaa gctccccgc catcacccac ttgtgctgca ggagtgtgtc agtgatgatg       1980
agacatctga acagctgacc cctgaggaag aggctgagga gacagaggcc tgggccaagc      2040
ctctgagcca actgtggcag aaccgacctc caaactttga ggctgagaag gaattcaatg      2100
agaccatggc caacaggcc cctcactgcg ctgtctgtat gatcttccag acttatcatc        2160
aggttgaatt tggaggcttt aatcagaact gtggaaatgc ttcagattta gccccccaga      2220
agcagaggac caagccattg attccagaaa tgtgcttcac ttcgactggc tgcagcacgg      2280
acatcaacct ttctactcct tatcttgagg aggatggcac cagcatactc gtttcctgca      2340
```

| | |
|---|---|
| agaagtgcag cgtccgggtc catgccagtt gctatggggt ccccccctgca aaggcttctg | 2400 |
| aagactggat gtgttctcgg tgttcagcca atgccctaga ggaggactgc tgtttatgct | 2460 |
| cattacgagg aggggccctg cagagagcaa atgatgacag gtgggtccac gtttcatgtg | 2520 |
| ctgtggcaat tctggaagca aggtttgtca acattgcaga aagaagtccg gtggatgtga | 2580 |
| gcaaaatccc cctgccccgc ttcaaactga atgtatctt ctgtaagaag cggaggaaaa | 2640 |
| gaactgctgg ctgctgtgtg cagtgttctc acggccgctg cccaactgcc ttccatgtga | 2700 |
| gctgcgccca ggctgccggt gtgatgatgc agcctgacga ctggcctttt gtggtcttca | 2760 |
| ttacctgctt tcgcacaaag attcctaatt tggagcgtgc caaggggggcc ttgcaaagca | 2820 |
| tcactgcagg ccagaaagtc attagcaagc ataagaacgg gcgcttctac cagtgtgaag | 2880 |
| tggtcaggct caccaccgag accttctatg aagtcaactt tgatgatggc tccttcagcg | 2940 |
| acaatcttta tcctgaggac atagtgagcc aggactgtct ccagtttggt cctcctgctg | 3000 |
| aaggggaagt ggtccaagtg agatggacag acggccaagt ctatggagcc aagtttgtgg | 3060 |
| cctcccaccc tatccaaatg taccaggtgg agtttgagga tggctcacaa cttgtggtta | 3120 |
| agagagatga tgtatacaca ctggatgaag agcttcccaa gagagtcaaa tctagactgt | 3180 |
| cagtagcctc agacatgcgc ttcaatgaga ttttcacaga gaaagaggtt aagcaagaaa | 3240 |
| agaaacggca acgagttatc aactcaagat accgggaaga ttatattgag cctgcactat | 3300 |
| accgggccat catggagtag gtgcttccag ggtccaaggg attctcagcc atccaggcaa | 3360 |
| gagcactctg ggttccacag cacagcagac atggaacgct gaagtctctg aaagtgaagt | 3420 |
| tgtaaaaaga aaaggaatga ataaccgac ccatcatctt ctcacccacc ctcattgcat | 3480 |
| tccgctgtag tgaaaggacg agccatttct gggcacgtgg cagcagtcgc tgatctccca | 3540 |
| gctgaggggc tgagcactgg aatgctgtgg ctgcactggc cccagtccat agaggggtca | 3600 |
| actatgctgg ctggactggc tgccttgttc ctggcctagg acttagcttc ataactatca | 3660 |
| cctgcaccga ctaggctgag gtgctggtac ttgccccaac ccctactttt gtatttatat | 3720 |
| gtgtgtgtgt gtgtcgtgc gtgcgtgcgt gcgtgtatgt ttggtctgga ccagcttctg | 3780 |
| ccagcccctg gccttttactt tcttccttgc ctatgcaggg caaacaaaat gtgaaattct | 3840 |
| gccctcagct gagctgagta agggctcctg ggggttggct ggagatgggt gtggcatctg | 3900 |
| tccaggcctg gaaccgtctc aagacagtgc tggcaaagct gcagtattga gatgctaagg | 3960 |
| agctgatgcc acctctttgt cttcccctaa aggagaacat ggggataaca tgggtgtgtg | 4020 |
| cccacaacac tctaggtgca gagccccgt ggcaaagtat tacagggtgt gggtggggat | 4080 |
| taccctgaat cggggatttt aatgatggaa gcaggcagag cctggtgggt gattctgtca | 4140 |
| acagaaaatt gcaatcatgc aggggctggg agggttagga tgaaaaaact ggggccattg | 4200 |
| gaggcccact gtaggtggga gggagctgat tttggggtgg ggggtgggac tagagggcaa | 4260 |
| tactgaaggg gttaaacagg ttttttgctcc tcaagaattt gtttgcctgg gcccaggatt | 4320 |
| ggagggcttc acaccaatac cctgtgtata caagaatcag atttataata cttccccttt | 4380 |
| tttgttacgt atgaacacta taaaccaaat tattttg | 4417 |

<210> SEQ ID NO 28
<211> LENGTH: 5595
<212> TYPE: DNA
<213> ORGANISM: Homo sapiens

<400> SEQUENCE: 28

| | |
|---|---|
| gtcgccagca accgagcggg gcccggcccg agcggggcct gggggtgcga cgccgagggc | 60 |

-continued

```
gggggagagc gcgccgctgc tcccggaccg ggccgcgcac gccgcctcag gaaccatcac    120
tgttgctgga ggcacctgac aaatcctagc gaattttttgg agcatctcca cccaggaacc    180
tcgccatcca gaagtgtgct tcccgcacag ctgcagccat ggggtctgag gaccacggcg    240
cccagaaccc cagctgtaaa atcatgacgt ttcgcccaac catggaagaa tttaaagact    300
tcaacaaata cgtggcctac atagagtcgc agggagccca ccgggcgggc ctggccaaga    360
tcatcccccc gaaggagtgg aagccgcggc agacgtatga tgacatcgac gacgtggtga    420
tcccggcgcc catccagcag gtggtgacgg gccagtcggg cctcttcacg cagtacaata    480
tccagaagaa ggccatgaca gtgggcgagt accgccgcct ggccaacagc gagaagtact    540 gtacccccgcg gcaccaggac tttgacgacc ttgaacgcaa atactggaag aacctcacct    600
ttgtctcccc gatctacggg gctgacatca gcggctcttt gtatgatgac gacgtggccc    660
agtggaacat cgggagcctc cggaccatcc tggacatggt ggagcgcgag tgcggcacca    720
tcatcgaggg cgtgaacacg ccctacctgt acttcggcat gtggaagacc accttcgcct    780
ggcacaccga ggacatggac ctgtacagca tcaactacct gcactttggg gagcctaagt    840
cctggtacgc catcccacca gagcacggca agcgcctgga gcggctggcc atcggcttct    900
tccccgggag ctcgcagggc tgcgacgcct tcctgcggca taagatgacc ctcatctcgc    960
ccatcatcct gaagaagtac gggatcccct cagccggat cacgcaggag gccggggaat   1020
tcatgatcac atttccctac ggctaccacg ccggcttcaa tcacgggttc aactgcgcag   1080
aatctaccaa cttcgccacc ctgcggtgga ttgactacgg caaagtggcc actcagtgca   1140
cgtgccggaa ggacatggtc aagatctcca tggacgtgtt cgtgcgcatc ctgcagcccg   1200
agcgctacga gctgtggaag cagggcaagg acctcacggt gctggaccac acgcggccca   1260
cggcgctcac cagccccgag ctgagctcct ggagtgcgtc ccgggcctcg ctgaaggcca   1320
agctcctccg caggtctcac cggaaacgga gccagcccaa gaagccgaag cccgaagacc   1380
ccaagttccc tggggagggt acggctgggg cagcgctcct agaggaggct ggggcagcg   1440 tgaaggagga ggctgggccg gaggttgacc ccgaggagga ggaggaggag ccgcagccac   1500
tgccacacgc ccgggaggcc gagggcgcag aagaggacgg gaggggcaag ctgcggccaa   1560
ccaaggccaa gagcgagcgg aagaagaaga gcttcggcct gctgcccca cagctgccgc   1620 ccccgcctgc tcacttcccc tcagaggagg cgctgtggct gccatcccca ctggagcccc   1680
cggtgctggg cccaggccct gcagccatgg aggagagccc cctgccggca ccccttaatg   1740
tcgtgccccc tgaggtgccc agtgaggagc tagaggccaa gctcggccc atcatcccca   1800 tgctgtacgt ggtgccgcgg ccgggcaagg cagccttcaa ccaggagcac gtgtcctgcc   1860
agcaggcctt tgagcacttt gcccagaagg gtccgacctg gaaggaacca gtttcccca   1920 tggagctgac ggggccagag gacggtgcag ccagcagtgg ggcaggtcgc atggagacca   1980
aagcccgggc cggagagggg caggcaccgt ccacattttc caaattgaag atggagatca   2040
agaagagccg gcgccatccc ctgggccggc cgcccacccg gtccccactg tcggtggtga   2100
agcaggaggc ctcaagtgac gaggaggcat ccccttttctc cggggaggaa gatgtgagtg   2160
acccggacgc cttgaggccg ctgctgtctc tgcagtggaa gaacagggcg ccagcttcc   2220 aggccgagag gaagttcaac gcagcggctg cgcgcacgga gccctactgc gccatctgca   2280
cgctcttcta ccccctactgc caggccctac agactgagaa ggaggcaccc atagcctccc   2340
tcggagaggg ctgccgggcc acattaccct ccaaaagccg tcagaagacc cgaccgctca   2400
tccctgagat gtgcttcacc tctggcggtg agaacacgga gccgctgcct gccaactcct   2460
```

```
acatcggcga cgacgggacc agcccctga tcgcctgcgg caagtgctgc ctgcaggtcc      2520
atgccagttg ctatggcatc cgtcccgagc tggtcaatga aggctggacg tgttcccggt      2580
gcgcggccca cgcctggact gcggagtgct gcctgtgcaa cctgcgagga ggtgcgctgc      2640
agatgaccac cgataggagg tggatccacg tgatctgtgc catcgcagtc cccgaggcgc      2700
gcttcctgaa cgtgattgag cgccaccctg tggacatcag cgccatcccc gagcagcggt      2760
ggaagctgaa atgcgtgtac tgccggaagc ggatgaagaa ggtgtcaggt gcctgtatcc      2820
agtgctccta cgagcactgc tccacgtcct tccacgtgac ctgcgcccac gccgcaggcg      2880
tgctcatgga gccggacgac tggccctatg tggtctccat cacctgcctc aagcacaagt      2940
cgggggggtca cgctgtccaa ctcctgaggg ccgtgtccct aggccaggtg gtcatcacca      3000
agaaccgcaa cgggctgtac taccgctgtc gcgtcatcgg tgccgcctcg cagacctgct      3060
acgaagtgaa cttcgacgat ggctcctaca gcgacaacct gtaccctgag agcatcacga      3120
gtagggactg tgtccagctg gaccccctt ccgaggggga gctggtggag ctccggtgga      3180
ctgacggcaa cctctacaag gccaagttca tctcctccgt caccagccac atctaccagg      3240
tggagtttga ggacgggtcc cagctgacgg tgaagcgtgg ggacatcttc acctggagg      3300
aggagctgcc caagagggtc cgctctcggc tgtcactgag cacgggggca ccgcaggagc      3360
ccgccttctc gggggaggag gccaaggccg ccaagcgccc gcgtgtgggc accccgcttg      3420
ccacggagga ctccgggcgg agccaggact acgtggcctt cgtggagagc ctcctgcagg      3480
tgcaggccg gccggagcc ccttctagg acagctggcc gctcaggcga ccctcagccc      3540
ggcggggagg ccatggcatg ccccgggcgt tcgcttgctg tgaattcctg tcctcgtgtc      3600
cccgacccc gagaggccac ctccaagccg cgggtgcccc ctagggcgac aggagccagc      3660
gggacgccgc acgcggcccc agactcaggg agcagggcca ggcgggctcg ggggccggcc      3720
aggggagcac cccactcaac tactcagaat tttaaaccat gtaagctctc ttcttctcga      3780
aaaggtgcta ctgcaatgcc ctactgagca acctttgaga ttgtcacttc tgtacataaa      3840
ccacctttgt gaggctcttt ctataaatac atattgttta aaaaaagca agaaaaaaag      3900
gaaaacaaag gaaaatatcc ccaaagttgt tttctagatt tgtggcttta agaaaaaaca      3960
aaacaaaaca aacacattgt ttttctcaga accaggattc tctgagaggt cagagcatct      4020
cgctgttttt ttgttgttgt tttaaaatat tatgatttgg ctacagacca ggcagggaaa      4080
gagacccggt aattggaggg tgagcctcgg ggggggggca ggacgccccg gtttcggcac      4140
agcccggtca ctcacggcct cgctctcgcc tcaccccggc tcctgggctt tgatggtctg      4200
gtgccagtgc ctgtgcccac tctgtgcctg ctgggaggag gcccaggctc tctggtggcc      4260
gcccctgtgc acctggccag gggaagcccg ggggtctggg gcctccctcc gtctgcgccc      4320
acctttgcag aataaactct ctcctggggt ttgtctatct ttgtttctct cacccgagag      4380
aaacgcaggt gttccagagg cttccttgca gacaaagcac ccctgcacct cccatggctc      4440
aggatgaggg aggccccag gcccttctgg ttggtagtga gtgtggacag cttcccagct      4500
cttcgggtac aaccctgagc aggtcggggg acacagggcc gaggcaggcc ttcgggcccc      4560
cttttcgcctg cttccgggca gggacgaggc ctggtgtcct cgctccaccc acccacgctg      4620
ctgtcacctg aggggaatct gcttcttagg agtgggttga gctgatagag aaaaaacggc      4680
cttcagccca ggctgggaag cgccttctcc aggtgcctct ccctcaccag ctctgcaccc      4740
ctctggggag ccttccccac cttagctgtc tcctgcccca gggagggatg gaggagataa      4800
tttgcttata ttaaaaacaa aaaatggctg aggcaggagt ttgggaccag cctgggctat      4860
```

-continued

```
atagcaagac cccatcacta caaatttttt acaaattagc taggtgtggt ggtgcgcacc    4920
tgtggtccca gctactcggg aggctgtggt gggaggattg cttgagtcca ggaggttgag    4980
gctgcagtca gctcagattg caccactgca ctccagcctg gcaacagag cgagaccctg     5040 tctccaaaaa aaaaaaaaaa gcaatgttta tattataaaa gagtgtccta acagtccccg    5100
ggctagagag gactaaggaa aacagagaga gtgttacgca ggagcaagcc tttcatttcc    5160 ttggtgggg aggggggcgg ttgccctgga gagggccggg gtcggggagg ttgggggtg      5220 tcagccaaaa cgtggaggtg tccctctgca cgcagccctc gcccggcgtg gcgctgacac    5280
tgtattctta tgttgtttga aaatgctatt tatattgtaa agaagcgggc gggtgccct     5340 gctgcccttg tcccttgggg gtcacaccca tccctggtg ggctcctggg cggcctgcgc     5400
agatgggcca cagaagggca ggccggagct gcacactctc cccacgaagg tatctctgtg    5460
tcttactctg tgcaaagacg cggcaaaacc cagtgccctg gttttccccc acccgagatg    5520
aaggatacgc tgtatttttt gcctaatgtc cctgcctcta ggttcataat gaattaaagg    5580
ttcatgaacg ctgcg                                                      5595
```

<210> SEQ ID NO 29
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Cys
        35                  40

<210> SEQ ID NO 30
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(me3)

<400> SEQUENCE: 30

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Cys
        35                  40

<210> SEQ ID NO 31
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
tgctgttgac agtgagcgcg ccagatagca gcaatgaaga tagtgaagcc acagatgtat    60
cttcattgct gctatctggc ttgcctactg cctcgga                              97
```

<210> SEQ ID NO 32
<211> LENGTH: 75
<212> TYPE: PRT
<213> ORGANISM: Homo sapiens

<400> SEQUENCE: 32

```
Gly Met Trp Lys Thr Thr Phe Ala Trp His Thr Glu Asp Met Asp Leu
1               5                   10                  15

Tyr Ser Ile Asn Tyr Leu His Phe Gly Glu Pro Lys Ser Trp Tyr Ala
            20                  25                  30

Ile Pro Pro Glu His Gly Pro Tyr Gly Tyr His Ala Gly Phe Asn His
        35                  40                  45

Gly Phe Asn Cys Ala Glu Ser Thr Asn Phe Ala Thr Val Arg Trp Ile
    50                  55                  60

Asp Tyr Gly Lys Val Ala Lys Leu Cys Thr Cys
65                  70                  75
```

<210> SEQ ID NO 33
<211> LENGTH: 75
<212> TYPE: PRT
<213> ORGANISM: Homo sapiens

<400> SEQUENCE: 33

```
Gly Met Trp Lys Thr Ser Phe Ala Trp His Thr Glu Asp Met Asp Leu
1               5                   10                  15

Tyr Ser Ile Asn Tyr Leu His Phe Gly Glu Pro Lys Ser Trp Tyr Ser
            20                  25                  30

Val Pro Pro Glu His Gly Pro Tyr Gly Tyr His Ala Gly Phe Asn His
        35                  40                  45

Gly Phe Asn Cys Ala Glu Ser Thr Asn Phe Ala Thr Arg Arg Trp Ile
    50                  55                  60

Glu Tyr Gly Lys Gln Ala Val Leu Cys Ser Cys
65                  70                  75
```

<210> SEQ ID NO 34
<211> LENGTH: 73
<212> TYPE: PRT
<213> ORGANISM: Homo sapiens

<400> SEQUENCE: 34

```
Val Arg Gly Cys Tyr Thr Asp Phe His Val Asp Phe Gly Gly Thr Ser
1               5                   10                  15

Val Trp Tyr His Ile His Gln Gly Gly Lys Val Phe Trp Leu Ile Pro
            20                  25                  30

Pro Thr Ala His Ser Gly Trp Ile His Ala Val Tyr Thr Pro Thr Asp
        35                  40                  45

Thr Leu Val Phe Gly Gly Asn Phe Leu His Ser Phe Asn Ile Pro Met
    50                  55                  60

Gln Leu Lys Ile Tyr Asn Ile Glu Asp
65                  70
```

<210> SEQ ID NO 35
<211> LENGTH: 71
<212> TYPE: PRT
<213> ORGANISM: Homo sapiens

<400> SEQUENCE: 35

Met Glu Gly Asn Val Thr Pro Ala His Tyr Asp Glu Gln Gln Asn Phe
1               5                   10                  15

Pro Ala Gln Ile Lys Gly Tyr Lys Arg Cys Ile Leu Phe Pro Pro Asp
            20                  25                  30

Gln Phe Met Tyr Trp Trp His His Ile Glu Ser Leu Leu Asn Gly Gly
        35                  40                  45

Ile Thr Ile Thr Val Asn Phe Trp Tyr Lys Gly Ala Pro Thr Pro Lys
    50                  55                  60

Arg Ile Glu Tyr Pro Leu Lys
65                  70

<210> SEQ ID NO 36
<211> LENGTH: 73
<212> TYPE: PRT
<213> ORGANISM: Schizasaccharomyces pombe

<400> SEQUENCE: 36

Ala Glu Asn Ser Tyr Thr Glu Phe His Ile Glu Phe Gly Gly Ser Ser
1               5                   10                  15

Ala Tyr Tyr Ile Asn Leu Asp Gly Cys Lys Ile Phe Tyr Leu Ile Pro
            20                  25                  30

Gly Thr Ser Lys Ser Gly Trp Ile Tyr Ala Val Val Thr Pro Cys Asp
        35                  40                  45

Thr Ile Ser Ile Ala Gly Asn Phe Leu Thr Phe Leu His Ile Tyr Pro
    50                  55                  60

Gln Leu Ser Ile Tyr Asn Leu Glu Leu
65                  70

<210> SEQ ID NO 37
<211> LENGTH: 116
<212> TYPE: PRT
<213> ORGANISM: Homo sapiens

<400> SEQUENCE: 37

Asp Glu Gly Val Asp Glu Trp Asn Ile Ala Arg Leu Asn Thr Val Leu
1               5                   10                  15

Asp Val Val Glu Glu Glu Cys Gly Ile Ser Ile Glu Gly Val Asn Thr
            20                  25                  30

Pro Tyr Leu Tyr Phe Gly Met Trp Lys Thr Thr Phe Ala Trp His Thr
        35                  40                  45

Glu Asp Met Asp Leu Tyr Ser Ile Asn Tyr Leu His Phe Gly Glu Pro
    50                  55                  60

Lys Ser Trp Tyr Ala Ile Pro Pro Glu His Gly Lys Arg Leu Glu Arg
65                  70                  75                  80

Leu Ala Gln Gly Phe Phe Pro Ser Ser Ser Gln Gly Cys Asp Ala Phe
                85                  90                  95

Leu Arg His Lys Met Thr Leu Ile Ser Pro Ser Val Leu Lys Lys Tyr
            100                 105                 110

Gly Ile Pro Phe
            115

<210> SEQ ID NO 38
<211> LENGTH: 116
<212> TYPE: PRT
<213> ORGANISM: Homo sapiens

<400> SEQUENCE: 38

```
Glu Lys His Val Asp Glu Trp Asn Ile Gly Arg Leu Arg Thr Ile Leu
1               5                   10                  15

Asp Leu Val Glu Lys Glu Ser Gly Ile Thr Ile Glu Gly Val Asn Thr
                20                  25                  30

Pro Tyr Leu Tyr Phe Gly Met Trp Lys Thr Ser Phe Ala Trp His Thr
            35                  40                  45

Glu Asp Met Asp Leu Tyr Ser Ile Asn Tyr Leu His Phe Gly Glu Pro
        50                  55                  60

Lys Ser Trp Tyr Ser Val Pro Pro Glu His Gly Lys Arg Leu Glu Arg
65                  70                  75                  80

Leu Ala Lys Gly Phe Phe Pro Gly Ser Ala Gln Ser Cys Glu Ala Phe
                85                  90                  95

Leu Arg His Lys Met Thr Leu Ile Ser Pro Leu Met Leu Lys Lys Tyr
                100                 105                 110

Gly Ile Pro Phe
            115

<210> SEQ ID NO 39
<211> LENGTH: 116
<212> TYPE: PRT
<213> ORGANISM: Homo sapiens

<400> SEQUENCE: 39

Asp Asp Asp Val Ala Gln Trp Asn Ile Gly Ser Leu Arg Thr Ile Leu
1               5                   10                  15

Asp Met Val Glu Arg Glu Cys Gly Thr Ile Glu Gly Val Asn Thr
                20                  25                  30

Pro Tyr Leu Tyr Phe Gly Met Trp Lys Thr Thr Phe Ala Trp His Thr
            35                  40                  45

Glu Asp Met Asp Leu Tyr Ser Ile Asn Tyr Leu His Phe Gly Glu Pro
        50                  55                  60

Lys Ser Trp Tyr Ala Ile Pro Pro Glu His Gly Lys Arg Leu Glu Arg
65                  70                  75                  80

Leu Ala Ile Gly Phe Phe Pro Gly Ser Ser Gln Gly Cys Asp Ala Phe
                85                  90                  95

Leu Arg His Lys Met Thr Leu Ile Ser Pro Ile Ile Leu Lys Lys Tyr
                100                 105                 110

Gly Ile Pro Phe
            115

<210> SEQ ID NO 40
<211> LENGTH: 116
<212> TYPE: PRT
<213> ORGANISM: Homo sapiens

<400> SEQUENCE: 40

Asp Glu Asn Thr Lys Gln Trp Asn Leu Gly His Leu Gly Thr Ile Gln
1               5                   10                  15

Asp Leu Leu Glu Lys Glu Cys Gly Val Val Ile Glu Gly Val Asn Thr
                20                  25                  30

Pro Tyr Leu Tyr Phe Gly Met Trp Lys Thr Thr Phe Ala Trp His Thr
            35                  40                  45

Glu Asp Met Asp Leu Tyr Ser Ile Asn Tyr Leu His Leu Gly Glu Pro
        50                  55                  60

Lys Thr Trp Tyr Val Val Pro Pro Glu His Gly Gln Arg Leu Glu Arg
65                  70                  75                  80

Leu Ala Arg Glu Leu Phe Pro Gly Ser Ser Arg Gly Cys Gly Ala Phe
```

```
                    85                  90                  95
Leu Arg His Lys Val Ala Leu Ile Ser Pro Thr Val Leu Lys Glu Asn
                100                 105                 110

Gly Ile Pro Phe
        115

<210> SEQ ID NO 41
<211> LENGTH: 116
<212> TYPE: PRT
<213> ORGANISM: Homo sapiens

<400> SEQUENCE: 41

Glu Tyr Leu Asp Ser Gly Trp Asn Leu Asn Met Pro Val Met Glu
1               5                   10                  15

Gln Ser Val Leu Ala His Ile Thr Ala Asp Ile Cys Gly Met Lys Leu
                20                  25                  30

Pro Trp Leu Tyr Val Gly Met Cys Phe Ser Ser Phe Cys Trp His Ile
            35                  40                  45

Glu Asp His Trp Ser Tyr Ser Ile Asn Tyr Leu His Trp Gly Glu Pro
    50                  55                  60

Lys Thr Trp Tyr Gly Val Pro Gly Tyr Ala Ala Glu Gln Leu Glu Asn
65                  70                  75                  80

Val Met Lys Lys Leu Ala Pro Glu Leu Phe Val Ser Gln Pro Asp Leu
                85                  90                  95

Leu His Gln Leu Val Thr Ile Met Asn Pro Asn Thr Leu Met Thr His
                100                 105                 110

Glu Val Pro Val
        115

<210> SEQ ID NO 42
<211> LENGTH: 116
<212> TYPE: PRT
<213> ORGANISM: Homo sapiens

<400> SEQUENCE: 42

Glu Tyr Ala Thr Ser Gly Trp Asn Leu Asn Val Met Pro Val Leu Glu
1               5                   10                  15

Gln Ser Val Leu Cys His Ile Asn Ala Asp Ile Ser Gly Met Lys Val
                20                  25                  30

Pro Trp Leu Tyr Val Gly Met Val Phe Ser Ala Phe Cys Trp His Ile
            35                  40                  45

Glu Asp His Trp Ser Tyr Ser Ile Asn Tyr Leu His Trp Gly Glu Pro
    50                  55                  60

Lys Thr Trp Tyr Gly Val Pro Ser Leu Ala Ala Glu His Leu Glu Glu
65                  70                  75                  80

Val Met Lys Lys Leu Thr Pro Glu Leu Phe Asp Ser Gln Pro Asp Leu
                85                  90                  95

Leu His Gln Leu Val Thr Leu Met Asn Pro Asn Thr Leu Met Ser His
                100                 105                 110

Gly Val Pro Val
        115

<210> SEQ ID NO 43
<211> LENGTH: 116
<212> TYPE: PRT
<213> ORGANISM: Homo sapiens

<400> SEQUENCE: 43
```

```
Glu Tyr Ala Leu Ser Gly Trp Asn Leu Asn Asn Met Pro Val Leu Glu
1               5                   10                  15

Gln Ser Val Leu Ala His Ile Asn Val Asp Ile Ser Gly Met Lys Val
            20                  25                  30

Pro Trp Leu Tyr Val Gly Met Cys Phe Ser Ser Phe Cys Trp His Ile
            35                  40                  45

Glu Asp His Trp Ser Tyr Ser Ile Asn Tyr Leu His Trp Gly Glu Pro
50                  55                  60

Lys Thr Trp Tyr Gly Val Pro Ser His Ala Ala Glu Gln Leu Glu Glu
65                  70                  75                  80

Val Met Arg Glu Leu Ala Pro Glu Leu Phe Glu Ser Gln Pro Asp Leu
                85                  90                  95

Leu His Gln Leu Val Thr Ile Met Asn Pro Asn Val Leu Met Glu His
                100                 105                 110

Gly Val Pro Val
            115

<210> SEQ ID NO 44
<211> LENGTH: 116
<212> TYPE: PRT
<213> ORGANISM: Homo sapiens

<400> SEQUENCE: 44

Glu Tyr Ala Thr Ser Gly Trp Asn Leu Asn Val Met Pro Val Leu Asp
1               5                   10                  15

Gln Ser Val Leu Cys His Ile Asn Ala Asp Ile Ser Gly Met Lys Val
            20                  25                  30

Pro Trp Leu Tyr Val Gly Met Val Phe Ser Ala Phe Cys Trp His Ile
            35                  40                  45

Glu Asp His Trp Ser Tyr Ser Ile Asn Tyr Leu His Trp Gly Glu Pro
50                  55                  60

Lys Thr Trp Tyr Gly Val Pro Ser Leu Ala Ala Glu His Leu Glu Glu
65                  70                  75                  80

Val Met Lys Met Leu Thr Pro Glu Leu Phe Asp Ser Gln Pro Asp Leu
                85                  90                  95

Leu His Gln Leu Val Thr Leu Met Asn Pro Asn Thr Leu Met Ser His
                100                 105                 110

Gly Val Pro Val
            115

<210> SEQ ID NO 45
<211> LENGTH: 113
<212> TYPE: PRT
<213> ORGANISM: Homo sapiens

<400> SEQUENCE: 45

Arg Trp Lys Pro Gln Leu Gln Glu Leu Leu Lys Leu Pro Ala Phe Met
1               5                   10                  15

Arg Val Thr Ser Thr Gly Asn Met Leu Ser His Val Gly His Thr Ile
            20                  25                  30

Leu Gly Met Asn Thr Val Gln Leu Tyr Met Lys Val Pro Gly Ser Arg
            35                  40                  45

Thr Pro Gly His Gln Glu Asn Asn Asn Phe Cys Ser Val Asn Ile Asn
50                  55                  60

Ile Gly Pro Gly Asp Cys Glu Trp Phe Ala Val His Glu His Tyr Trp
65                  70                  75                  80

Glu Thr Ile Ser Ala Phe Cys Asp Arg His Gly Val Asp Tyr Leu Thr
```

```
                85                  90                  95
Gly Ser Trp Trp Pro Ile Leu Asp Asp Leu Tyr Ala Ser Asn Ile Pro
            100                 105                 110
Val

<210> SEQ ID NO 46
<211> LENGTH: 113
<212> TYPE: PRT
<213> ORGANISM: Homo sapiens

<400> SEQUENCE: 46

Lys Trp Lys Leu Gln Leu His Glu Leu Thr Lys Leu Pro Ala Phe Val
1               5                   10                  15

Arg Val Val Ser Ala Gly Asn Leu Leu Ser His Val Gly His Thr Ile
            20                  25                  30

Leu Gly Met Asn Thr Val Gln Leu Tyr Met Lys Val Pro Gly Ser Arg
        35                  40                  45

Thr Pro Gly His Gln Glu Asn Asn Phe Cys Ser Val Asn Ile Asn
    50                  55                  60

Ile Gly Pro Gly Asp Cys Glu Trp Phe Val Val Pro Glu Gly Tyr Trp
65                  70                  75                  80

Gly Val Leu Asn Asp Phe Cys Glu Lys Asn Asn Leu Asn Phe Leu Met
                85                  90                  95

Gly Ser Trp Trp Pro Asn Leu Glu Asp Leu Tyr Glu Ala Asn Val Pro
            100                 105                 110

Val

<210> SEQ ID NO 47
<211> LENGTH: 113
<212> TYPE: PRT
<213> ORGANISM: Homo sapiens

<400> SEQUENCE: 47

Lys Trp Lys Leu Gln Leu His Glu Leu Thr Lys Leu Pro Ala Phe Ala
1               5                   10                  15

Arg Val Val Ser Ala Gly Asn Leu Leu Thr His Val Gly His Thr Ile
            20                  25                  30

Leu Gly Met Asn Thr Val Gln Leu Tyr Met Lys Val Pro Gly Ser Arg
        35                  40                  45

Thr Pro Gly His Gln Glu Asn Asn Phe Cys Ser Val Asn Ile Asn
    50                  55                  60

Ile Gly Pro Gly Asp Cys Glu Trp Phe Val Val Pro Glu Asp Tyr Trp
65                  70                  75                  80

Gly Val Leu Asn Asp Phe Cys Glu Lys Asn Asn Leu Asn Phe Leu Met
                85                  90                  95

Ser Ser Trp Trp Pro Asn Leu Glu Asp Leu Tyr Glu Ala Asn Val Pro
            100                 105                 110

Val

<210> SEQ ID NO 48
<211> LENGTH: 137
<212> TYPE: PRT
<213> ORGANISM: Homo sapiens

<400> SEQUENCE: 48

Leu Ser Leu Pro Asn Ser Trp Asn Tyr Arg His Leu Pro Ser Cys Pro
1               5                   10                  15
```

Thr Asn Phe Cys Ile Phe Val Glu Thr Gly Phe His His Val Gly Gln
            20                  25                  30

Ala Cys Leu Glu Leu Leu Thr Ser Gly Gly Leu Leu Ala Ser Ala Ser
            35                  40                  45

Gln Ser Ala Gly Ile Thr Gly Val Ser His His Ala Arg Leu Gln Leu
50                      55                  60

Tyr Met Lys Val Pro Gly Ser Arg Thr Pro Gly His Gln Glu Asn Asn
65                  70                  75                  80

Asn Phe Cys Ser Val Asn Ile Asn Ile Gly Pro Gly Asp Cys Glu Trp
                85                  90                  95

Phe Val Val Pro Glu Asp Tyr Trp Gly Val Leu Asn Asp Phe Cys Glu
            100                 105                 110

Lys Asn Asn Leu Asn Phe Leu Met Ser Ser Trp Trp Pro Asn Leu Glu
        115                 120                 125

Asp Leu Tyr Glu Ala Asn Val Pro Val
    130                 135

<210> SEQ ID NO 49
<211> LENGTH: 125
<212> TYPE: PRT
<213> ORGANISM: Homo sapiens

<400> SEQUENCE: 49

Phe Ser His Thr Lys Leu Glu His Leu Val Lys Arg Pro Thr Val Val
1               5                   10                  15

Asp Leu Val Asp Trp Val Asp Asn Met Trp Pro Gln His Leu Lys Glu
            20                  25                  30

Lys Gln Thr Glu Ala Thr Asn Ala Ile Ala Glu Met Lys Tyr Pro Lys
        35                  40                  45

Val Lys Lys Tyr Cys Leu Met Ser Val Lys Gly Gly Phe Thr Asp Phe
    50                  55                  60

His Ile Asp Phe Gly Gly Thr Ser Val Trp Tyr His Val Phe Arg Gly
65                  70                  75                  80

Gly Lys Ile Phe Trp Leu Ile Pro Pro Thr Leu His Asn Leu Ala Leu
                85                  90                  95

Tyr Glu Glu Trp Val Leu Ser Gly Lys Gln Ser Asp Ile Phe Leu Gly
            100                 105                 110

Asp Arg Val Glu Arg Cys Gln Arg Ile Glu Leu Lys Gln
        115                 120                 125

<210> SEQ ID NO 50
<211> LENGTH: 125
<212> TYPE: PRT
<213> ORGANISM: Homo sapiens

<400> SEQUENCE: 50

Phe Ser His Thr Arg Leu Glu Asn Met Val Gln Arg Pro Ser Thr Val
1               5                   10                  15

Asp Phe Ile Asp Trp Val Asp Asn Met Trp Pro Arg His Leu Lys Glu
            20                  25                  30

Ser Gln Thr Glu Ser Thr Asn Ala Ile Leu Glu Met Gln Tyr Pro Lys
        35                  40                  45

Val Gln Lys Tyr Cys Leu Met Ser Val Arg Gly Cys Tyr Thr Asp Phe
    50                  55                  60

His Val Asp Phe Gly Gly Thr Ser Val Trp Tyr His Ile His Gln Gly
65                  70                  75                  80

Gly Lys Val Phe Trp Leu Ile Pro Pro Thr Ala His Asn Leu Glu Leu 85                  90                  95
Tyr Glu Asn Trp Leu Leu Ser Gly Lys Gln Gly Asp Ile Phe Leu Gly
                100                 105                 110

Asp Arg Val Ser Asp Cys Gln Arg Ile Glu Leu Lys Gln
            115                 120                 125

<210> SEQ ID NO 51
<211> LENGTH: 113
<212> TYPE: PRT
<213> ORGANISM: Homo sapiens

<400> SEQUENCE: 51

Phe Ser Asp Thr Arg Met Ser Ser Phe Val Glu Pro Pro Asp Ile Val
1               5                   10                  15

Lys Lys Leu Ser Trp Val Glu Asn Tyr Trp Pro Asp Asp Ala Leu Leu
            20                  25                  30

Ala Lys Pro Lys Val Thr Lys Tyr Cys Leu Ile Cys Val Lys Asp Ser
        35                  40                  45

Tyr Thr Asp Phe His Ile Asp Ser Gly Gly Ala Ser Ala Trp Tyr His
    50                  55                  60

Val Leu Lys Gly Glu Lys Thr Phe Tyr Leu Ile Arg Pro Ala Ser Ala
65                  70                  75                  80

Asn Ile Ser Leu Tyr Glu Arg Trp Arg Ser Ala Ser Asn His Ser Glu
                85                  90                  95

Met Phe Phe Ala Asp Gln Val Asp Lys Cys Tyr Lys Cys Ile Val Lys
                100                 105                 110

Gln

<210> SEQ ID NO 52
<211> LENGTH: 113
<212> TYPE: PRT
<213> ORGANISM: Homo sapiens

<400> SEQUENCE: 52

Phe Ser Asp Thr Arg Leu Ser Asn Leu Val Glu Thr Pro Lys Ile Val
1               5                   10                  15

Arg Lys Leu Ser Trp Val Glu Asn Leu Trp Pro Glu Glu Cys Val Phe
            20                  25                  30

Glu Arg Pro Asn Val Gln Lys Tyr Cys Leu Met Ser Val Arg Asp Ser
        35                  40                  45

Tyr Thr Asp Phe His Ile Asp Phe Gly Gly Thr Ser Val Trp Tyr His
    50                  55                  60

Val Leu Lys Gly Glu Lys Ile Phe Tyr Leu Ile Arg Pro Thr Asn Ala
65                  70                  75                  80

Asn Leu Thr Leu Phe Glu Cys Trp Ser Ser Ser Asn Gln Asn Glu
                85                  90                  95

Met Phe Phe Gly Asp Gln Val Asp Lys Cys Tyr Lys Cys Ser Val Lys
                100                 105                 110

Gln

<210> SEQ ID NO 53
<211> LENGTH: 113
<212> TYPE: PRT
<213> ORGANISM: Homo sapiens

<400> SEQUENCE: 53

Phe Ser Asp Thr Lys Met Ser Glu Leu Val Glu Val Pro Asp Ile Ala
1               5                   10                  15

Lys Lys Leu Ser Trp Val Glu Asn Tyr Trp Pro Asp Asp Ser Val Phe
            20                  25                  30

Pro Lys Pro Phe Val Gln Lys Tyr Cys Leu Met Gly Val Gln Asp Ser
            35                  40                  45

Tyr Thr Asp Phe His Ile Asp Phe Gly Gly Thr Ser Val Trp Tyr His
        50                  55                  60

Val Leu Trp Gly Glu Lys Ile Phe Tyr Leu Ile Lys Pro Thr Asp Glu
65                  70                  75                  80

Asn Leu Ala Arg Tyr Glu Ser Trp Ser Ser Val Thr Gln Ser Glu
                85                  90                  95

Val Phe Phe Gly Asp Lys Val Asp Lys Cys Tyr Lys Cys Val Val Lys
                100                 105                 110

Gln

<210> SEQ ID NO 54
<211> LENGTH: 115
<212> TYPE: PRT
<213> ORGANISM: Homo sapiens

<400> SEQUENCE: 54

Pro Lys Arg Arg Lys Leu Leu Glu Asp Tyr Lys Val Pro Lys Phe Phe
1               5                   10                  15

Thr Asp Asp Leu Phe Gln Tyr Ala Gly Glu Lys Arg Arg Pro Pro Tyr
            20                  25                  30

Arg Trp Phe Val Met Gly Pro Pro Arg Ser Gly Thr Gly Ile His Ile
            35                  40                  45

Asp Pro Leu Gly Thr Ser Ala Trp Asn Ala Leu Val Gln Gly His Lys
        50                  55                  60

Arg Trp Cys Leu Phe Pro Thr Ser Thr Pro Arg Glu Leu Ile Lys Val
65                  70                  75                  80

Thr Arg Asp Glu Gly Gly Asn Gln Gln Asp Gly Ala Ile Thr Trp Phe
                85                  90                  95

Asn Val Ile Tyr Pro Arg Thr Gln Leu Pro Thr Trp Pro Pro Glu Phe
                100                 105                 110

Lys Pro Leu
        115

<210> SEQ ID NO 55
<211> LENGTH: 122
<212> TYPE: PRT
<213> ORGANISM: Homo sapiens

<400> SEQUENCE: 55

Leu Tyr Leu Gln Gln Thr Leu Asn Asp Thr Val Gly Arg Lys Ile Val
1               5                   10                  15

Met Asp Phe Leu Gly Phe Asn Trp Asn Trp Ile Asn Lys Gln Gln Gly
            20                  25                  30

Lys Arg Gly Trp Gly Gln Leu Thr Ser Asn Leu Leu Leu Ile Gly Met
            35                  40                  45

Glu Gly Asn Val Thr Pro Ala His Tyr Asp Glu Gln Gln Asn Phe Phe
        50                  55                  60

Ala Gln Ile Lys Gly Tyr Lys Arg Cys Ile Leu Phe Pro Pro Asp Gln
65                  70                  75                  80

Phe Glu Cys Leu Tyr Pro Tyr Pro Val His His Pro Cys Asp Arg Gln
                85                  90                  95

Ser Gln Val Asp Phe Asp Asn Pro Asp Tyr Glu Arg Phe Pro Asn Phe

```
                    100                 105                 110

Gln Asn Val Val Gly Tyr Glu Thr Val Val
        115                 120

<210> SEQ ID NO 56
<211> LENGTH: 127
<212> TYPE: PRT
<213> ORGANISM: Homo sapiens

<400> SEQUENCE: 56

Asp Thr Ser Arg Val Glu Asn Leu Ala Ala Ser Leu Pro Leu Pro Glu
1               5                   10                  15

Tyr Cys Ala Leu His Gly Lys Leu Asn Leu Ala Ser Tyr Leu Pro Pro
            20                  25                  30

Gly Leu Ala Leu Arg Pro Leu Glu Pro Gln Leu Trp Ala Ala Tyr Gly
        35                  40                  45

Val Ser Pro His Arg Gly His Leu Gly Thr Lys Asn Leu Cys Val Glu
    50                  55                  60

Val Ala Asp Leu Val Ser Ile Leu Val His Ala Asp Thr Pro Leu Pro
65                  70                  75                  80

Ala Trp His Arg Ala Gln Lys Asp Phe Leu Ser Gly Leu Asp Gly Glu
                85                  90                  95

Gly Leu Trp Ser Pro Gly Ser Gln Val Ser Thr Val Trp His Val Phe
            100                 105                 110

Arg Ala Gln Asp Ala Gln Arg Ile Arg Arg Phe Leu Gln Met Val
        115                 120                 125

<210> SEQ ID NO 57
<211> LENGTH: 135
<212> TYPE: PRT
<213> ORGANISM: Homo sapiens

<400> SEQUENCE: 57

Met Pro Thr Arg Phe Glu Asp Leu Met Glu Asn Leu Pro Leu Pro Glu
1               5                   10                  15

Tyr Thr Lys Arg Asp Gly Arg Leu Asn Leu Ala Ser Arg Leu Pro Ser
            20                  25                  30

Tyr Phe Val Arg Pro Asp Leu Gly Pro Lys Met Tyr Asn Ala Tyr Gly
        35                  40                  45

Leu Ile Thr Ala Glu Asp Arg Arg Val Gly Thr Thr Asn Leu His Leu
    50                  55                  60

Asp Val Ser Asp Ala Val Asn Val Met Val Tyr Val Gly Ile Pro Ile
65                  70                  75                  80

Gly Glu Gly Ala His Asp Glu Glu Val Leu Lys Thr Ile Asp Glu Gly
                85                  90                  95

Asp Ala Asp Glu Val Thr Lys Gln Arg Ile His Asp Gly Lys Glu Lys
            100                 105                 110

Pro Gly Ala Leu Trp His Ile Tyr Ala Ala Lys Asp Ala Glu Lys Ile
        115                 120                 125

Arg Glu Leu Leu Arg Lys Val
        130                 135

<210> SEQ ID NO 58
<211> LENGTH: 133
<212> TYPE: PRT
<213> ORGANISM: Homo sapiens

<400> SEQUENCE: 58
```

```
Met Pro Ala Arg Tyr Glu Asp Leu Leu Lys Ser Leu Pro Leu Pro Glu
 1               5                  10                  15

Tyr Cys Asn Pro Glu Gly Lys Phe Asn Leu Ala Ser His Leu Pro Gly
                20                  25                  30

Phe Phe Val Arg Pro Asp Leu Gly Pro Arg Leu Cys Ser Ala Tyr Gly
            35                  40                  45

Val Val Ala Ala Lys Asp His Asp Ile Gly Thr Thr Asn Leu His Ile
50                  55                  60

Glu Val Ser Asp Val Val Asn Ile Leu Val Tyr Val Gly Ile Ala Lys
65                  70                  75                  80

Gly Asn Gly Ile Leu Ser Lys Ala Gly Ile Leu Lys Lys Phe Glu Glu
                85                  90                  95

Glu Asp Leu Asp Asp Ile Leu Arg Lys Arg Leu Lys Asp Ser Ser Glu
            100                 105                 110

Ile Pro Gly Ala Leu Trp His Ile Tyr Ala Gly Lys Asp Val Asp Lys
        115                 120                 125

Ile Arg Glu Phe Leu
    130
```

<210> SEQ ID NO 59
<211> LENGTH: 135
<212> TYPE: PRT
<213> ORGANISM: Homo sapiens

<400> SEQUENCE: 59

```
Met Pro Ser Arg Phe Asp Asp Leu Met Ala Asn Ile Pro Leu Pro Glu
 1               5                  10                  15

Tyr Thr Arg Arg Asp Gly Lys Leu Asn Leu Ala Ser Arg Leu Pro Asn
                20                  25                  30

Tyr Phe Val Arg Pro Asp Leu Gly Pro Lys Met Tyr Asn Ala Tyr Gly
            35                  40                  45

Leu Ile Thr Pro Glu Asp Arg Lys Tyr Gly Thr Thr Asn Leu His Leu
        50                  55                  60

Asp Val Ser Asp Ala Ala Asn Val Met Val Tyr Val Gly Ile Pro Lys
65                  70                  75                  80

Gly Gln Cys Glu Gln Glu Glu Val Leu Lys Thr Ile Gln Asp Gly
                85                  90                  95

Asp Ser Asp Glu Leu Thr Ile Lys Arg Phe Ile Glu Gly Lys Glu Lys
            100                 105                 110

Pro Gly Ala Leu Trp His Ile Tyr Ala Ala Lys Asp Thr Glu Lys Ile
        115                 120                 125

Arg Glu Phe Leu Lys Lys Val
    130                 135
```

<210> SEQ ID NO 60
<211> LENGTH: 137
<212> TYPE: PRT
<213> ORGANISM: Homo sapiens

<400> SEQUENCE: 60

```
Val Gln Lys Gln Cys Ser Asn Leu Pro Ser Glu Leu Pro Gln Leu Leu
 1               5                  10                  15

Pro Asp Leu Glu Ser His Val Pro Trp Ala Ser Glu Ala Leu Gly Lys
                20                  25                  30

Met Pro Asp Ala Val Asn Phe Trp Leu Gly Glu Ala Ala Ala Val Thr
            35                  40                  45

Ser Leu His Lys Asp His Tyr Glu Asn Leu Tyr Cys Val Val Ser Gly
```

```
                    50                  55                  60
Glu Lys His Phe Leu Phe His Pro Pro Ser Asp Arg Pro Phe Ile Pro
 65                  70                  75                  80

Tyr Glu Leu Tyr Thr Pro Ala Thr Tyr Gln Leu Thr Glu Gly Thr
                     85                  90                  95

Phe Lys Val Val Asp Glu Glu Ala Met Glu Lys Ala Glu Val Ser Arg
                    100                 105                 110

Thr Cys Leu Leu Thr Val Arg Val Leu Gln Ala His Arg Leu Pro Ser
                    115                 120                 125

Lys Asp Leu Val Thr Pro Ser Asp Cys
                    130                 135

<210> SEQ ID NO 61
<211> LENGTH: 156
<212> TYPE: PRT
<213> ORGANISM: Homo sapiens

<400> SEQUENCE: 61

Val Gln Lys Gln Cys Ser Asn Leu Pro Ser Glu Leu Pro Gln Leu Leu
 1               5                  10                  15

Pro Asp Leu Glu Ser His Val Pro Trp Ala Ser Glu Ala Leu Gly Lys
                 20                  25                  30

Met Pro Asp Ala Val Asn Phe Trp Leu Gly Glu Ala Ala Ala Val Thr
                 35                  40                  45

Ser Leu His Lys Asp His Tyr Glu Asn Leu Tyr Cys Val Val Ser Gly
             50                  55                  60

Glu Lys His Phe Leu Phe His Pro Pro Ser Asp Arg Pro Phe Ile Pro
 65                  70                  75                  80

Tyr Glu Leu Tyr Thr Pro Gly Thr Tyr Gln Pro Ser Asp Arg Pro Phe
                 85                  90                  95

Ile Pro Tyr Glu Leu Tyr Thr Pro Ala Thr Tyr Gln Leu Thr Glu Glu
                100                 105                 110

Gly Thr Phe Lys Val Val Asp Glu Glu Ala Met Glu Lys Val Pro Trp
                115                 120                 125

Ile Pro Leu Asp Pro Leu Ala Pro Asp Leu Ala Arg Tyr Pro Ser Tyr
                130                 135                 140

Ser Gln Ala Gln Ala Leu Arg Cys Met Val Arg Ala
145                 150                 155

<210> SEQ ID NO 62
<211> LENGTH: 101
<212> TYPE: PRT
<213> ORGANISM: Homo sapiens

<400> SEQUENCE: 62

Phe Asp Gln Lys Arg Ala Thr Ile Gln Phe His Gln Pro Gln Arg Phe
 1               5                  10                  15

Lys Asp Glu Leu Trp Arg Ile Gln Glu Lys Leu Glu Cys Tyr Phe Gly
                 20                  25                  30

Ser Leu Val Gly Ser Asn Val Tyr Ile Thr Pro Ala Gly Ser Gln Gly
                 35                  40                  45

Leu Pro Pro His Tyr Asp Asp Val Glu Val Phe Ile Leu Gln Leu Glu
             50                  55                  60

Gly Glu Lys His Trp Arg Leu Tyr His Pro Thr Val Pro Leu Ala Arg
 65                  70                  75                  80

Glu Tyr Ser Val Glu Ala Glu Glu Arg Ile Gly Arg Pro Val His Glu
                 85                  90                  95
```

```
<210> SEQ ID NO 63
<211> LENGTH: 106
<212> TYPE: PRT
<213> ORGANISM: Homo sapiens

<400> SEQUENCE: 63

Phe Met Leu Lys Pro
                100

Pro Thr Ser Leu Gly Asn Asp Thr Leu Tyr Phe Phe Gly Asp Asn Asn
1               5                   10                  15
Phe Ile Glu Trp Ala Ser Leu Phe Arg His Tyr Ser Pro Pro Pro Phe
            20                  25                  30
Gly Pro Leu Gly Thr Ala Pro Ala Tyr Ser Phe Gly Ile Ala Gly Ala
            35                  40                  45
Gly Ser Gly Val Pro Phe His Trp His Gly Pro Gly Tyr Ser Glu Val
            50                  55                  60
Ile Tyr Gly Arg Lys Arg Trp Phe Leu Tyr Pro Pro Glu Lys Thr Pro
65                  70                  75                  80
Glu Phe Arg Pro Asn Lys Thr Thr Leu Ala Trp Leu Arg Asp Thr Tyr
                85                  90                  95
Pro Ala Leu Pro Pro Ser Ala Arg Pro Leu
                100                 105

<210> SEQ ID NO 64
<211> LENGTH: 113
<212> TYPE: PRT
<213> ORGANISM: Homo sapiens

<400> SEQUENCE: 64

Pro Phe Ser Arg His Gly Trp Asn Leu Thr Val Leu Pro Asn Asn Thr
1               5                   10                  15
Gly Ser Ile Leu Arg His Leu Gly Ala Val Pro Gly Val Thr Ile Pro
            20                  25                  30
Trp Leu Asn Ile Gly Met Val Phe Ser Thr Ser Cys Trp Ser Arg Asp
            35                  40                  45
Gln Asn His Leu Pro Tyr Ile Asp Tyr Leu His Thr Gly Asp Cys Ile
            50                  55                  60
Trp Tyr Cys Ile Pro Ala Glu Glu Glu Asn Lys Leu Glu Asp Val Val
65                  70                  75                  80
His Thr Leu Leu Gln Ala Asn Gly Thr Pro Gly Leu Gln Met Leu Glu
                85                  90                  95
Ser Asn Val Met Ile Ser Pro Glu Val Leu Cys Lys Glu Gly Ile Lys
                100                 105                 110
Val
```